US007611866B2

(12) United States Patent
Georgiou et al.

(10) Patent No.: US 7,611,866 B2
(45) Date of Patent: *Nov. 3, 2009

(54) SELECTION OF BACTERIAL INNER-MEMBRANE ANCHOR POLYPEPTIDES

(75) Inventors: George Georgiou, Austin, TX (US); Ki Jun Jeong, Austin, TX (US); Barrett R. Harvey, Souderton, PA (US); Brent L. Iverson, Austin, TX (US)

(73) Assignee: Board of Regents, The University of Texas System, Austin, TX (US)

( * ) Notice: Subject to any disclaimer, the term of this patent is extended or adjusted under 35 U.S.C. 154(b) by 478 days.

This patent is subject to a terminal disclaimer.

(21) Appl. No.: 11/084,717

(22) Filed: Mar. 18, 2005

(65) Prior Publication Data

US 2005/0260736 A1 Nov. 24, 2005

Related U.S. Application Data

(63) Continuation-in-part of application No. 10/620,278, filed on Jul. 15, 2003, now Pat. No. 7,094,571.

(60) Provisional application No. 60/396,058, filed on Jul. 15, 2002, provisional application No. 60/554,324, filed on Mar. 18, 2004.

(51) Int. Cl.
| | |
|---|---|
| C12P 21/06 | (2006.01) |
| C12P 21/04 | (2006.01) |
| C12N 15/09 | (2006.01) |
| G01N 33/53 | (2006.01) |
| G01N 33/567 | (2006.01) |
| G01N 33/569 | (2006.01) |
| G01N 33/554 | (2006.01) |

(52) U.S. Cl. .................. 435/69.1; 435/69.2; 435/69.3; 435/69.7; 435/69.9; 435/7.1; 435/7.32; 435/71.1; 435/7.2

(58) Field of Classification Search .................. None
See application file for complete search history.

(56) References Cited

U.S. PATENT DOCUMENTS

| | | | |
|---|---|---|---|
| 5,160,974 A | 11/1992 | Siegel et al. | 356/246 |
| 5,223,409 A | 6/1993 | Ladner et al. | 435/69.7 |
| 5,348,867 A | 9/1994 | Georgiou et al. | 435/69.7 |
| 5,571,698 A | 11/1996 | Ladner et al. | 435/69.7 |
| 5,648,237 A | 7/1997 | Carter | 435/69.1 |
| 5,656,015 A | 8/1997 | Young | 601/2 |
| 5,744,314 A | 4/1998 | Menzel et al. | 435/7.2 |
| 5,759,810 A | 6/1998 | Honjo et al. | 435/69.1 |
| 5,780,279 A | 7/1998 | Matthews et al. | 435/172.3 |
| 5,824,520 A | 10/1998 | Mulligan-Kehoe | 435/91.41 |
| 5,837,500 A | 11/1998 | Ladner et al. | 435/69.7 |
| 5,866,344 A | 2/1999 | Georgiou | 435/7.21 |
| 5,922,545 A | 7/1999 | Mattheakis et al. | 435/6 |
| 6,001,823 A | 12/1999 | Hultgren et al. | 514/99 |
| 6,916,474 B2 | 7/2005 | Harvey et al. | 424/130.1 |
| 7,083,945 B1* | 8/2006 | Chen et al. | 435/69.1 |
| 7,094,571 B2* | 8/2006 | Harvey et al. | 435/69.1 |
| 2006/0029947 A1 | 2/2006 | Georgiou et al. | 435/6 |
| 2007/0065913 A1* | 3/2007 | Chen et al. | 435/69.1 |
| 2007/0099267 A1* | 5/2007 | Harvey et al. | 435/69.1 |

FOREIGN PATENT DOCUMENTS

| | | |
|---|---|---|
| EP | 177343 | 4/1986 |
| WO | WO 98/49286 | 11/1998 |
| WO | WO 99/60096 | 11/1999 |
| WO | WO 02/22861 | 3/2002 |
| WO | WO 02/34886 | 5/2002 |
| WO | WO 2005/019409 | 3/2005 |
| WO | WO 2005/095988 | 10/2005 |

OTHER PUBLICATIONS

Froshauer et al, J. Mol. Biol., 1988, 200:501-511.*
Georgiou et al, Tibtech, Jan. 1993, 11:6-10.*
Jung et al, Biotechnology and Bioengineering, Sep. 1, 2007, 98/1:39-47.*
Jeong et al, PNAS, May 15, 2007, 104/20:8247-8252.*
Harvey et al, PNAS, Jun. 22, 2004, 101/25:9193-9198.*
Dalbey et al, JBC, Dec. 15, 1985, 260/29:15925-15931.*
Francisco et al, PNAS, Nov. 1993, 90:10444-10448.*
Whitely et al, Advances in Cell and Molecular Biology of Membranes and Organelles, 1995, 4:1-16.*
Tullman-Ercek et al, JBC, Mar. 16, 2007, 282/11:8309-8316.*
Strauch et al, Protein Science, 2007, 16:1001-1008.*
Harvey et al, J. Immunological Methods, 2006, 308:43-52.*
Georgiou et al, Nature Biotechnology, Jan. 1997, 15:29-34.*
Thomas E. Creighton, Proteins: Structures and Molecular Properties, 1984, pp. 314-315.*
Thomas E. Creighton, Proteins Structure: A Practical Approach, 1989, pp. 184-186.*
Nosoh et al, Protein Stability and Stabilization through Protein Engineering, 1991, pp. 197-217.*

(Continued)

Primary Examiner—N. M Minnifield
(74) Attorney, Agent, or Firm—Fulbright & Jaworski L.L.P.

(57) ABSTRACT

The invention overcomes the deficiencies of the prior art by providing a rapid approach for isolating polypeptides capable of anchoring heterologous polypeptides to a bacterial inner membrane. In the technique, libraries of candidate anchor polypeptides are expressed as fusions with a heterologous polypeptide that is capable of being detected when bound to the inner membrane. In bacteria expressing a functional anchor sequence, the heterologous polypeptide becomes bound to outer face of the inner membrane. Bacteria with the functional anchor sequence can be identified by removing the outer membrane to remove non-anchored heterologous polypeptide followed by detection of anchored heterologous polypeptide. Such bacteria may be detected in numerous ways, including use of direct fluorescence or secondary antibodies that are fluorescently labeled, allowing use of efficient techniques such as fluorescence activated cell sorting (FACS).

23 Claims, 16 Drawing Sheets

OTHER PUBLICATIONS

Harvey et al., "Anchored periplasmic expression, a versatile technology for the isolation of high-affinity antibodies from *Escherichia coli*-expressed libraries", *Proc. Nat'l Acad. Sci.*, 101:9193-9198, 2004.

U.S. Appl. No. 10/288,269, filed Nov. 5, 2002, Georgiou et al.

Cirino et al., "Disruption of anthrax toxin binding with the use of human antibodies and competitive inhibitors," *Infect. Immunity*, 67:2957-2963, 1999.

Fuchs et al. "Seperation of *E. coli* expressing functional cell-wall bound antibody fragments by FACS," *Immunotechnology*, 2(2):97-102, 1996.

Harvey, "Anchored periplasmic expression (APEX) of protein libraries for flow cytometric selections," *American Chemical Society: Abstracts of paper at the national meeting of the American Chemical Society*, 224(1/2):BIOT-324, 2002.

Schier et al., "Isolation of high-affinity monomeric human anti-c-erbB-2 single chain Fv using affinity-driven selection," *J. Mol. Biol.*, 255:28-43, 1996.

Webster's Ninth New Collegiate Dictionary, p. 354, 1990.

U.S. Appl. No. 09/699,023, filed Oct. 27, 2000, Chen et al.

U.S. Appl. No. 10/620,278, filed Jul. 15, 2003, Harvey et al.

Ames, Journal of Bioenergetics and Biomembranes, 20:1-7, 1998.

Barbas et al., Proc. Natl. Acad. Sci. USA, 88:7978-7982, 1991.

Boder and Wittrup, "Yeast Surface Display for directed evolution of protein expression, affinity, and stability," *Methods Enzymol.*, 328:430-444, 2000.

Boder and Wittrup, "Yeast surface display for screening combinatorial polypeptide libraries," *Nature Biotechnology*, 15:553-557, 1997.

Boder et al., "Directed evolution of antibody fragments with monovalent femtomolar antigen-binding affinity," *Proc. Natl. Acad. Sci. USA*, 97(20):10701-10705, 2000.

Boeke et al., "Effects of Bacteriophage f1 Gene III Protein on the Host Cell Membrane," *Mol. Gen. Genet.*, 186:185-192, 1982.

Bradbury, "Selecting by microdialysis," *Nature Biotechnology*, 19:528-529, 2001.

Buchner and Rudolph, "Renaturation, purification, and characterization of recombinant Fab-fragments produced in *Escherichia coli*," *Bio/Technology*, 9(2):157-162, 1991.

Bukau et al., "Ca2+-induced permeabilization of the *Escherichia coli* outer membrane: comparison of transformation and reconstitution of binding-protein-dependent transport," *Journal of Bacteriology*, 163:61-68, 1985.

Burioni et al., "A new subtraction technique for molecular cloning of rare antiviral antibody specificities from phage display libraries," *Res. Virol.*, 149:327-330, 1998.

Burman et al., "Murein and the Outer Penetration Barrier of *Escherichia coli* K-12, *Proteus mirabilis*, and *Pseudomonas aeruginosa*," *J. Bacteriol.*, 112(3):1364-1374, 1972.

Chen et al., "In vitro scanning saturation mutagenesis of all the specificity determining residues in an antibody binding site," *Protein Eng.*, 12(4):349-356, 1999.

Chen et al., "Isolation of high-affinity ligand-binding proteins by periplasmic expression with cytometric screening (PECS)," *Nature Biotechnology*, 19:537-542, 2001.

Chen et al., "Selection and analysis of an optimized anti-VEGF antibody: crystal structure of an affinity-matured Fab in complex with antigen," *J. Mol. Biol.*, 293:865, 1999.

Chowdhury and Pastan, "Improving antibody affinity by mimicking somatic hypermutation in vitro," *Nat. Biotech.*, 17:568-572, 1999.

Coia et al., "Use of mutator cells as a means for increasing production levels of a recombinant antibody directed against Hepatitis B," *Gene* 201:203-209, 1997.

Corey et al., "Trypsin display on the surface of bacteriophage," *Gene*, 128:129, 1993.

Dall'Acqua and Carter, "Antibody engineering," *Curr. Opin. Struct. Biol.*, 8:443-450, 1998.

Danese and Silhavy, "Targeting and assembly of periplasmic and outer-membrane proteins in *Escherichia coli*," *Annu. Rev. Genet.*, 32:59-94, 1998.

Daugherty et al., "Development of an optimized expression system for the screening of antibody libraries displayed on the *Escherichia coli* surface," *Prot. Eng.*, 12:613-620, 1999.

Daugherty et al., "Flow cytometric screening of cell-based libraries," *J. Immunol. Methods.* 243:211-227, 2000.

Daugherty et al., "Quantitative analysis of the effects of the mutation frequency on the affinity maturation of single chain Fc antibodies," *PNAS*, 97:2029-2034, 2000.

De Haard et al., "A Large Non-immunized Human Fab Fragment Phage Library That Permits Rapid Isolation and Kinetic Analysis of High Affinity Antibodies," *J. Biol. Chem.*, 274(26):18218-18230, 1999.

De Haard et al., "Creating and engineering human antibodies for immunotherapy," *Advanced Drug Delivery Reviews*, 31:5-31, 1998.

De Wildt et al., "Antibody arrays for high-throughput screening of antibody—antigen interactions," *Nat. Biotechnol.* 18:989-994, 2000.

Decad and Nikaido, "Outer Membrane of Gram-Negative Bacteria, XII Molecular-Sieving Function of Cell Wall," *J. Bacteriol.*, 128(1):325-336, 1976.

Deng et al., "Basis for selection of improved carbohydrate-binding single-chain antibodies from synthetic gene libraries," *Proc. Natl. Acad. Sci. USA*. 92:4992-4996, 1995.

Deng et al., "Selection of Antibody Single-chain Variable Fragments with Improved Carbohydrate Binding by Phage Display," *J. Biol. Chem.*, 269:9533-9538, 1994.

Duenas and Borrebaeck, "Clonal selection and Amplification of Phage Displayed Antibodies by Linking Antigen Recognition and Phage Replication," *Biotechnology*, 12:999-1002, 1994.

Farmer et al., "Penetration of β-lactamase inhibitors into the periplasm of Gram-negative bacteria," *FEMS Microbiol. Lett.*, 176:11-15, 1999.

Feilmeier et al., "Green fluorescent protein functions as a reporter for protein localization in *Escherichia coli*," *J. Bacteriol.*, 182:4068-4076, 2000.

Fromant et al., "Direct random mutagenesis of gene-sized DNA fragments using polymerase chain reaction," *Anal. Biochem.*, 224:347-353, 1995.

Georgiou and Valax, "Expression of correctly folded proteins in *Esherichia coli*," *Curr. Opin. Biotechnol.*, 7(2):190-197, 1996.

Georgiou et al., "Display of heterologous proteins on the surface of microorganisms: From the screening of combinatorial libraries to live recombinant vaccines," *Nat. Biotechnol.* 15:29-34, 1997.

Georgiou, "Analysis of large libraries of protein mutants using flow cytometry," *Adv. Protein Chem.*, 55:293-315, 2000.

Giep et al., "pSKAP/S: an expression vector for the production of single-chain Fv alkaline phosphatase fusion proteins," *Prot. Exp. Purif.*, 16:63-69, 1999.

Gouffi, K., Santini, C. L. & Wu, L. F. (2002). Topology determination and functional analysis of the *Escherichia coli* TatC protein. *FEBS Lett* 525, 65-70.

Griep et al., "pSKAP/S: An Expression Vector for the Production of Single-Chain Fv Alkaline Phosphatase Fusion Proteins," *Prot. Exp. Purif.*, 16:63-69, 1999.

Griffiths et al., "Isolation of high affinity human antibodies directly from large synthetic repertoires," *EMBO J.*, 13:3245-3260, 1994.

Hancock and Wong, "Compounds which increase the permeability of the *Pseudomonas aeruginosa* outer membrane," *Antimicrobial Agents and Chemotherapy*, 26:48-52, 1984.

Harvey et al., "Anchored periplasmic expression, a versatile technology for the isolation of high-affinity antibodies from *Escherichia coli*-expressed libraries," *Proc. Natl. Acad. Sci.*, USA, 101(25):9193-9198, 2004.

Hawkins et al., "Selection of phage antibodies by binding affinity mimicking affinity maturation," *J. Mol. Biol.*, 226:889-896, 1992.

Hayhurst and Georgiou, "High-throughput antibody isolation," *Curr. Opin. Chem. Biol.*, 5:683-689, 2001.

Hayhurst and Harris, "*Escherichia coli* Skp chaperone coexpression inproves solubility and phage display of single-chain antibody fragments." *Protein Expr. Purif.*, 15:336-343, 1999.

Hayhurst et al., "Isolation and expression of recombinant antibody fragments to the biological warfare pathogen *Brucella melitensis*," *J. Immunol. Methods*, 276:185-196, 2003.

Hayhurst, "Improved expression characteristics of single-chain Fv fragments when downstream of the *Escherichia coli* maltose-binding protein or upstream of a single immunoglobulin-constant domain," *Protein Expr. Purif.*, 18:1-10, 2000.

Helander and Mattila-Sandholm, "Fluorometric assessment of gram-negative bacterial permeabilization," *J. of Applied Microbiology*, 88:213-219, 2000.

Higgins et al., Journal of Bioenergetics and Biomembranes, 22, 1990.

Hobot et al., "Periplasmic Gel: New Concept Resulting from the Reinvestigation of Bacterial Cell Envelope Ultrastructure by New Methods," *J. Bacteriol.*, 160(1):143-152, 1984.

Hoess, *Chem. Rev.*, "Protein design and phage display," *Chem. Rev.*, 101:3205-3218, 2001.

Hoischen et al., "Novel bacterial membrane surface display system using cell wall-less L-forms of *Proteus mirabilis* and *Escherichia coli*," *Applied and Environmental Microbiology*, 68:525-531, 2002.

Hoogenboom et al., "Creating and engineering human antibodies from immunotherapy," *Adv. Drug. Deliv. Rev.*, 31:5, 1998.

Hoogenboom, "Designing and optimizing library selection strategies for generating high-affinity antibodies," *Tibtech*, 15:62-70, 1997.

Hudson et al., "Recombinant antibody fragments," *Curr. Opin. Biotechnol.*, 9:395, 1998.

Hultgren et al., "Bacterial adhesins and their assembly," In: *Escherichia coli and Salmonella typhimurium. Cellular and Molecular Biology*, Frederick Neidhardt et al., eds. vol. 2:2730-2756, 1996.

Hultgren et al., "Pilus and nonpilus bacterial adhesins: assembly and function in cell recognition," *Cell*, 73:887-901, 1993.

Johns et al., "In vivo selection of sFv from phage display libraries," *J. Immunol. Methods*, 239:137-151, 2000.

Joo et al., "A high-throughput digital imaging screen for the discovery and directed evolution of oxygenases," *Chemistry & Biology*, 6:699-706, 1999.

Jouenne and Junter, "Do β-lactam antibiotics permeabilize the outer membrane of Gram-negative bacteria? An electochemical investigation," *FEMS Microbiol. Lett.*, 68:313-318, 1990.

Kipriyanov et al., "Rapid detection of recombinant antibody fragments directed against cell surface antigens by flow cytometry," *J. Immunol. Methods*, 196(1):51-62, 1996.

Kjaer et al., "Glycerol diversifies phage repertoire selections and lowers non-specific phage absorption," *FEBS Lett.*, 431:448-452, 1998.

Knappik et al., "Fully synthetic human combinatorial antibody libraries(HuCAL) based on modular consensus frameworks and CDRs randomized with trinucleotides," *J. Mol. Biol.*, 296:57-86, 2000.

Krebber et al., "Inclusion of an upstream transcriptional terminator in phage display vectors abolishes background expression of toxic fusions with coat protein g3p," *Gene*, 178:71-74, 1996.

Krebber et al., "Reliable cloning of functional antibody variable domains from hybridomas and spleen cell repertoires employing a reengineered phage display system," *J. Immunol. Methods*, 201:35-55, 1997.

Le and Trotta, "Purification of secreted recombinant proteins from *Escherichia coli*," *Bioprocess Technol.*, 12:163-181, 1991.

Levitan, "Stochastic Modeling and Optimization of Phage Display," *J. Mol. Biol.*, 277:893-916, 1998.

Li et al., "X-ray snapshots of the maturation of an antibody response to protein antigen," *Nat. Struct. Biol.*, 10:482-488, 2003.

Low et al., "Mimicking somatic hypermutation: affinity maturation of antibodies displayed on bacteriophage using a bacterial mutator strain," *J. Mol. Biol.*, 260: 359-368, 1996.

Lutz, S., Ostermeier, M. & Benkovic, S. J. (2001). Rapid generation of incremental truncation libraries for protein engineering using alpha-phosphothioate nucleotides. *Nucleic Acids Res* 29, E16.

MacKenzie and To, "The role of valency in the selection of anti-carbohydrate singl-chain Fvs from phage display libraries," *J. Immunol. Methods*, 220:39-49, 1998.

MacKenzie et al., "Analysis by surface plasmon resonance of the influence of valence on the ligand binding affinity and kinetics of an anti-carbohydrate antibody," *J. Biol. Chem.*, 271(3):1527-1533, 1996.

Maenaka et al., "A stable phage-display system using a phagemid vector: phage display of hen egg-white lysozyme (HEL), *Escherichia coli* alkaline, phosphatase, and anti-HEL monoclonal antibody, HyHEL10," *Biochem. Biophys. Res. Commun.*, 218:682, 1996.

Makrides, "Strategies for achieving high-level expression of genes in *Escherichia coli*," *Microbiol. Rev.*, 60(3):512-538, 1996.

Malmborg et al., "Selection of binders form phage displayed antibody libraries using the BIAcore biosensor," *J. Immunol. Methods*, 198:51-57, 1996.

Martinez et al., "Accurate Kinetic Modeling of Alkaline Phosphatase in the *Escherichia coli* Periplasm: Implications for Enzyme Properitres and Substrate Diffusion," *Biochemistry*, 35:1179-1186, 1996.

Martinez et al., "Steady-state enzyme kinetics in the *Escherichia coli* periplasm: a model of a whole cell biocatalyst," *J. Biotechnol.*, 71:59-66, 1999.

Maynard and Georgiou, "Antibody Engineering," *Annu. Rev. Biomed. Eng.*, 2:339-376, 2000.

Maynard et al., "Protection against anthrax toxin by recombinant antibody fragments correlates with antigen affinity," *Nat. Biotechnol.*, 20:597-601, 2002.

Mingarro et al., "Membrane-protein engineering," *Trends Biotechnol.*, 15:432-437, 1997.

Miroux and Walker, "Over-production of proteins in *Escherichia coli*: mutant hosts that allow synthesis of some membrane proteins and globular proteins at high levels," *J. Mol. Biol.*, 260:289-298, 1996.

Mutuberria et al., "Model systems to study the parameters determining the success of phage antibody selections on complex antigens," *J. Immunol. Methods*, 231:65-81, 1999.

Naglak and Wang, "Recovery of a foreign protein from the periplasm of *Escherichia coli* by chemical permeabilization," *Enzyme Microb. Technol.*, 12(8):603-611, 1990.

Nakae et al., The Journal of Biological Chemistry, 250, 1975.

Nikaido and Vaara, "Molecular Basis of Bacterial Outer Membrane Permeability," *Microbiol. Rev.*, 49(1):1-32, 1985.

Nikaido, "Multidrug efflux pumps of gram-negative bacteria," *Journal of Bacteriology*, 178(20):5853-5859, 1996.

Nosoh, Y. et al. in "Protein stability and stabilization through protein engineering, 1991," (Chapter 7, p. 197).

Oliver, "Periplasm," 88-103, 1996.

Olsen et al., "Function-based isolation of novel enzymes from a large library," *Nat. Biotechnol.*, 18:1071-1074, 2000.

Painbeni et al. *Proc. Nat. Acad. Sci.* U.S.A., 94:6712-, 1997.

Pini et al., "Design and Use of a Phage Display Library," *J. Biol. Chem.*, 273(34):21769-21776, 1998.

Pugsley, "The complete general secretary pathway in gram-negative bacteria," *Microbiol. Rev.*, 57(1):50-108, 1993.

Rodi and Makowski, "Phage-display technology-finding a needle in a vast molecular haystack," *Curr. Opin. Biotechnol.*, 10:87-93, 1999.

Sagt et al., "Impaired cutinase secretion in *Saccharomyces cerevisiae* induces irregular endoplasmic reticulum (ER) membran proliferation, oxidative stress, and ER-associated degradation," *Appl. Environ. Microbiol.*, 68(5):2155-2160, 2002.

Samuelson et al., "Multidrug efflux pumps of gram-negatice bacteria," *Nature*, 406:637-641, 2000.

Sawyer and Blattner, "Rapid detection of antigen binding by antibody fragments expressed in the periplasm of *Escherichia coli*," *Protein Engineering*, 4(8):947-953, 1991.

Sblattero and Bradbury, "Exploiting recombination in single bacteria to make large phage antibody libraries," *Nat. Biotechnol.*, 18:75-80, 2000.

Seydel et al., "Testing the '2+ rule' for lipoprotein sorting in the *Escherichia coli* cell envelope with a new genetic selection," *Mol. Microbiol.*, 34(4):810-821, 1999.

Sheets et al., "Efficient construction of a large nonimmune phage antibody library: The production of high-affinity human single-chain antibodies to protein antigens," *Proc. Natl. Acad. Sci. USA.*, 95:6157-6162, 1998.

Shusta et al., "Yeast Polypeptide Fusion Surface Display Levels Predict Thermal Stability and Soluble Secretion Efficiency," *J. Mol. Biol.*, 292:949-956, 1999.

Somerville et al., "Bacterial aspects assiciated with the expresion of a single-chain antibody fragment in *Escherichia coli*," *Appl. Microbiol. Biotechnol.*, 42:595-603, 1994.

Stathopoulos et al., "Characterization of *Escherichia coli* expressing an Lpp'OmpA(46-159)-PhoA fusion protein localized in the outer membrane," *Appl. Microbiol. Biotechnol.*, 45:112-119, 1996.

Staudenmaier et al. (*Journal of Bacteriology*, May 1989, p. 2626-2633).

Thomas E. Creighton, in his book "Protein Structure: A Practical Approach. 1989; pp. 184-186".

Thomas E. Creighton, in his book, "Proteins: Structures and Molecular Properties, 1984", (p. 315).

Thompson et al., "Affinity maturation of a high-affinity human monoclonal antibody agaisnt the third hypercvariable loop of human immunodeficiency virus: use of phage display to improve affinity and broaden strain reactivity," *J. Mol.Biol.*, 256:77-88, 1996.

Van Wielink and Duine, "How big is the periplasmic space?" *Trends Biochem Sci.*, 15:136-137, 1990.

Vaughan et al., "Human antibodies with sub-nanometer affinites isolated from a large non-immunized phage display library," *Nat. Biotechnol.*, 14:309-314, 1996.

Wittrup, "The single cell as a microplate well," *Nat. Biotechnol.*, 18:1039-1040, 2000.

Wulfing and Pluckthun, "Protein folding in the periplasm of *Escherichia coli*," 12(5):685-692, 1994.

Yakushi et al., "A new ABC transporter mediating the detachment of lipid-modified proteins from membranes," *Nat. Cell. Biol.*, 2:212-218, 2000.

Yakushi et al., "Lethality of the covalent linkage between mislocalized major outer membrane lipoprotein and the poptidoglycan of *Escherichia coli*," *Journal of Bacteriology*, 179(9):2857, 1997.

Yamaguchi, "A single amino acid determinant of the membrane localization of lipoproteins in *E. coli*," *Cell*, 53(3):423-432, 1988.

Yu et al., "Lipoprotein-28, a cytoplasmic membrane lipoprotein from *Escherichia coli*," *J. Biol. Chem.*, 261(5):2284-2288, 1986.

\* cited by examiner

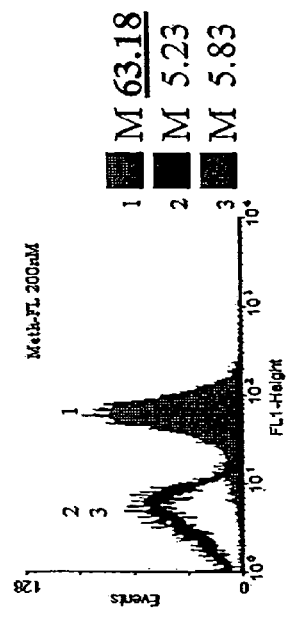
FIG. 1A
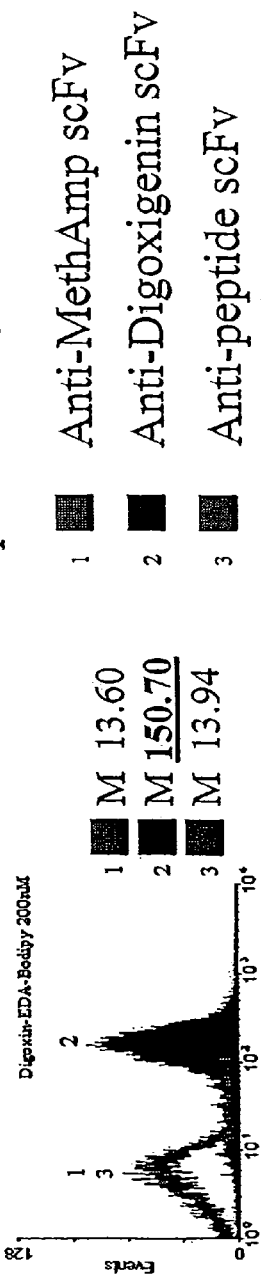
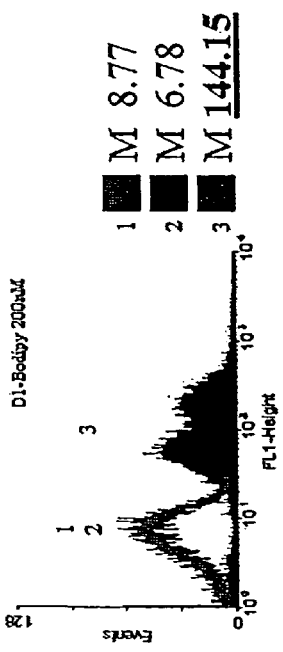
FIG. 1B
FIG. 1C

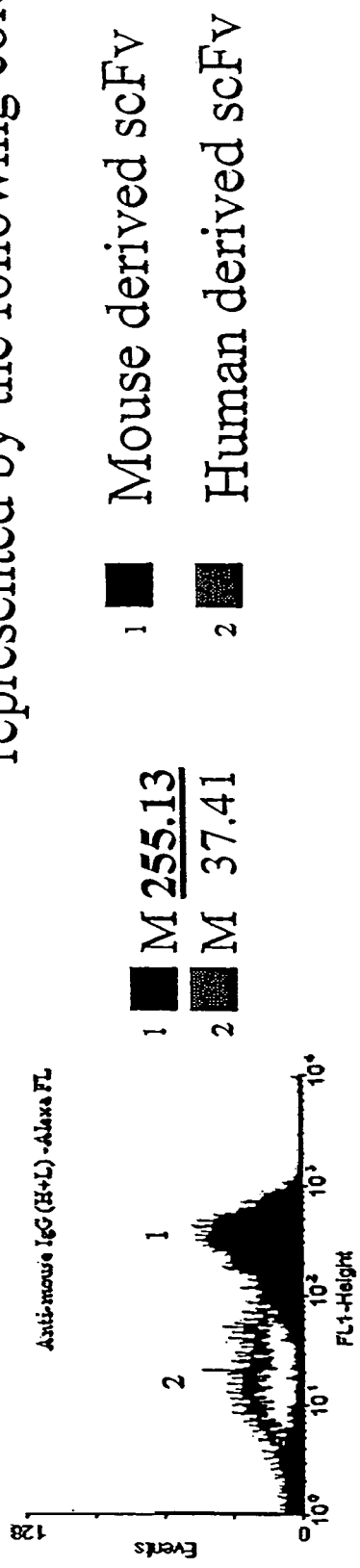
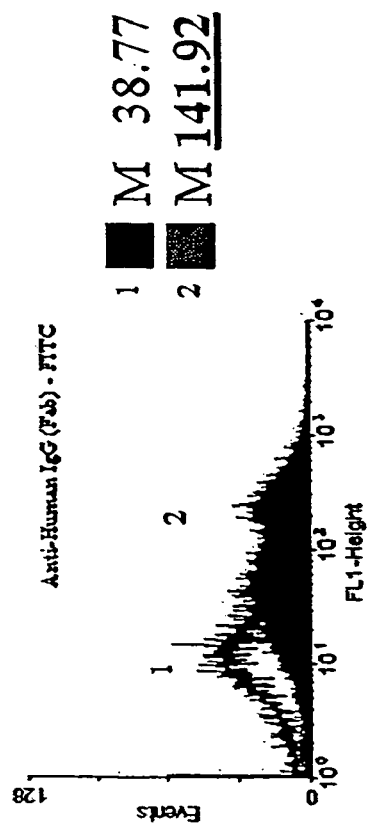
FIG. 2A
FIG. 2B

Variable Light

14B7scFV DIQMTQTTSSLSAS-GDRVTISCRASQDIRNYLNWYQQKPDGTVKLLIYYTSRLQSGVPSRFSGSGSGTDYSLTISNQEQEDIGTYFCQQGNTLPWTFGGGTKLEIKR
M18scFV  DIQMTQTTSSLSAS-GDRVTVSCRASQDIRNYLNWYQQKPDGTVKFLIYYTSRLQPGVPSRFSGSGSGTDYSLTINNLEQEDIGTYFCQQGNTPPWTFGGGTKLEIKR

Linker

14B7scFV GGGGSGGGGSGGGGSGGGGS
M18scFV  GGGGSDGGGSGGGGSGGGGS

Variable Heavy

14B7scFV EVQLQQSGPELVKPGASVKISCKDSGYAFSSSWMNWVKQRPGQGLEWIGRIYPGDGTNYNGKFKGKATLTADKSSSTAYMQLSSLTSVDSAVYFCARSGLLRYAMDYWGQGTSVTVSS
M18scFV  EVQLQQSGPELVKPGASVKISCKDSGYAFNSSWMNWVKQRPGQGLEWIGRIYPGDGSNYNGKFEGKAILTADKSSSTAYMQLSSLTSVDSAVYFQARSGLLRYAMDYWGQGTSVTVSS

*FIG. 11*

SEQUENCE LISTING

```
<160> NUMBER OF SEQ ID NOS: 61

<210> SEQ ID NO 1
<211> LENGTH: 17
<212> TYPE: DNA
<213> ORGANISM: Artificial Sequence
<220> FEATURE:
<223> OTHER INFORMATION: Description of Artificial Sequence:   Synthetic
      Primer

<400> SEQUENCE: 1
caggaaacag ctatgac                                                     17

<210> SEQ ID NO 2
<211> LENGTH: 17
<212> TYPE: DNA
<213> ORGANISM: Artificial Sequence
<220> FEATURE:
<223> OTHER INFORMATION: Description of Artificial Sequence:   Synthetic
      Primer

<400> SEQUENCE: 2
gaattttctg tatgagg                                                     17

<210> SEQ ID NO 3
<211> LENGTH: 18
<212> TYPE: DNA
<213> ORGANISM: Artificial Sequence
```

-continued

```
<220> FEATURE:
<223> OTHER INFORMATION: Description of Artificial Sequence:  Synthetic
      Primer

<400> SEQUENCE: 3
gccacctccg cctgaacc                                                    18

<210> SEQ ID NO 4
<211> LENGTH: 17
<212> TYPE: DNA
<213> ORGANISM: Artificial Sequence
<220> FEATURE:
<223> OTHER INFORMATION: Description of Artificial Sequence:  Synthetic
      Primer

<400> SEQUENCE: 4
ctatgcggcc ccattca                                                     17

<210> SEQ ID NO 5
<211> LENGTH: 5
<212> TYPE: DNA
<213> ORGANISM: Artificial Sequence
<220> FEATURE:
<223> OTHER INFORMATION: Description of Artificial Sequence:  Synthetic
      Primer

<400> SEQUENCE: 5 aaaaa                                                                   5

<210> SEQ ID NO 6
<211> LENGTH: 39
<212> TYPE: DNA
<213> ORGANISM: Artificial Sequence
<220> FEATURE:
<223> OTHER INFORMATION: Description of Artificial Sequence:  Synthetic
      Primer

<400> SEQUENCE: 6
gaaggagata tacatatgaa actgacaaca catcatcta                             39

<210> SEQ ID NO 7
<211> LENGTH: 45
<212> TYPE: DNA
<213> ORGANISM: Artificial Sequence
<220> FEATURE:
<223> OTHER INFORMATION: Description of Artificial Sequence:  Synthetic
      Primer

<400> SEQUENCE: 7
ctgggccatg gccggctggg cctcgctgct actctggtcg caacc                      45

<210> SEQ ID NO 8
<211> LENGTH: 7
<212> TYPE: PRT
<213> ORGANISM: Artificial Sequence
<220> FEATURE:
<223> OTHER INFORMATION: Description of Artificial Sequence:  Synthetic
      Peptide

<400> SEQUENCE: 8

Gln Thr Thr His Val Pro Pro
  1               5

<210> SEQ ID NO 9
<211> LENGTH: 7
<212> TYPE: PRT
<213> ORGANISM: Artificial Sequence
```

```
<220> FEATURE:
<223> OTHER INFORMATION: Description of Artificial Sequence:  Synthetic
      Peptide

<400> SEQUENCE: 9

Gln Thr Thr His Val Pro Pro
  1               5

<210> SEQ ID NO 10
<211> LENGTH: 7
<212> TYPE: PRT
<213> ORGANISM: Artificial Sequence
<220> FEATURE:
<223> OTHER INFORMATION: Description of Artificial Sequence:  Synthetic
      Peptide

<400> SEQUENCE: 10

Gln Thr Thr His Ser Pro Ala
  1               5

<210> SEQ ID NO 11
<211> LENGTH: 7
<212> TYPE: PRT
<213> ORGANISM: Artificial Sequence
<220> FEATURE:
<223> OTHER INFORMATION: Description of Artificial Sequence:  Synthetic
      Peptide

<400> SEQUENCE: 11

Gln Thr Thr His Leu Pro Thr
  1               5

<210> SEQ ID NO 12
<211> LENGTH: 7
<212> TYPE: PRT
<213> ORGANISM: Artificial Sequence
<220> FEATURE:
<223> OTHER INFORMATION: Description of Artificial Sequence:  Synthetic
      Peptide

<400> SEQUENCE: 12

Gln Thr Thr His Thr Pro Pro
  1               5

<210> SEQ ID NO 13
<211> LENGTH: 7
<212> TYPE: PRT
<213> ORGANISM: Artificial Sequence
<220> FEATURE:
<223> OTHER INFORMATION: Description of Artificial Sequence:  Synthetic
      Peptide

<400> SEQUENCE: 13

Gln Thr Thr His Thr Pro Pro
  1               5

<210> SEQ ID NO 14
<211> LENGTH: 7
<212> TYPE: PRT
<213> ORGANISM: Artificial Sequence
<220> FEATURE:
<223> OTHER INFORMATION: Description of Artificial Sequence:  Synthetic
      Peptide

<400> SEQUENCE: 14

Gln Thr Thr His Ile Pro Thr
  1               5
```

```
<210> SEQ ID NO 15
<211> LENGTH: 7
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 15

Gln Thr Thr His Val Pro Pro
  1               5

<210> SEQ ID NO 16
<211> LENGTH: 7
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 16

Gln Thr Thr His Val Pro Ala
  1               5

<210> SEQ ID NO 17
<211> LENGTH: 7
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 17

Gln Thr Thr His Ile Pro Ala
  1               5

<210> SEQ ID NO 18
<211> LENGTH: 7
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 18

Gln Thr Thr His Leu Pro Ala
  1               5

<210> SEQ ID NO 19
<211> LENGTH: 7
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 19

Gln Thr Thr His Val Pro Cys
  1               5

<210> SEQ ID NO 20
<211> LENGTH: 741
<212> TYPE: DNA
<213> ORGANISM: Artificial Sequence
<220> FEATURE:
<223> OTHER INFORMATION: Description of Artificial Sequence: Synthetic
      Primer
```

-continued

```
<400> SEQUENCE: 20
gatattcaga tgacacagac tacatcctcc ctgtctgcct ctctgggaga cagagtcacc      60
atcagttgca gggcaagtca ggacattagg aattatttaa actggtatca gcagaaacca     120
gatggaactg ttaaactcct gatctactac acatcaagat tacagtcagg agtcccatca     180
aggttcagtg gcagtgggtc tggaacagat tattctctca ccattagcaa ccaggagcaa     240
gaagatattg gcacttactt tgccaacag ggtaatacgc ttccgtggac gttcggtgga      300
ggcaccaagc tggaaataaa acgtggtggt ggtggttctg gtggtggtgg ttctggcggc     360
ggcggctccg gtggtggtgg atccgaggtc caactgcaac agtctggacc tgagctggtg     420
aagcctgggg cctcagtgaa gatttcctgc aaagattctg gctacgcatt cagtagctct     480
tggatgaact gggtgaagca gaggcctgga cagggtcttg agtggattgg acggatttat     540
cctggagatg gagatactaa ctacaatggg aagttcaagg gcaaggccac actgactgca     600
gacaaatcct ccagcacagc ctacatgcag ctcagcagcc tgacctctgt ggactctgcg     660
gtctatttct gtgcaagatc ggggttacta cgttatgcta tggactactg gggtcaagga     720
acctcagtca ccgtctcctc g                                               741
```

<210> SEQ ID NO 21
<211> LENGTH: 247
<212> TYPE: PRT
<213> ORGANISM: Artificial Sequence
<220> FEATURE:
<223> OTHER INFORMATION: Description of Artificial Sequence: Synthetic Peptide

<400> SEQUENCE: 21

Asp Ile Gln Met Thr Gln Thr Thr Ser Ser Leu Ser Ala Ser Leu Gly
1               5                   10                  15

Asp Arg Val Thr Ile Ser Cys Arg Ala Ser Gln Asp Ile Arg Asn Tyr
            20                  25                  30

Leu Asn Trp Tyr Gln Gln Lys Pro Asp Gly Thr Val Lys Leu Leu Ile
        35                  40                  45

Tyr Tyr Thr Ser Arg Leu Gln Ser Gly Val Pro Ser Arg Phe Ser Gly
    50                  55                  60

Ser Gly Ser Gly Thr Asp Tyr Ser Leu Thr Ile Ser Asn Gln Glu Gln
65                  70                  75                  80

Glu Asp Ile Gly Thr Tyr Phe Cys Gln Gln Gly Asn Thr Leu Pro Trp
                85                  90                  95

Thr Phe Gly Gly Gly Thr Lys Leu Glu Ile Lys Arg Gly Gly Gly Gly
            100                 105                 110

Ser Gly Gly Gly Gly Ser Gly Gly Gly Ser Gly Gly Gly Gly Ser
        115                 120                 125

Glu Val Gln Leu Gln Gln Ser Gly Pro Glu Leu Val Lys Pro Gly Ala
    130                 135                 140

Ser Val Lys Ile Ser Cys Lys Asp Ser Gly Tyr Ala Phe Ser Ser Ser
145                 150                 155                 160

Trp Met Asn Trp Val Lys Gln Arg Pro Gly Gln Gly Leu Glu Trp Ile
                165                 170                 175

Gly Arg Ile Tyr Pro Gly Asp Gly Asp Thr Asn Tyr Asn Gly Lys Phe
            180                 185                 190

Lys Gly Lys Ala Thr Leu Thr Ala Asp Lys Ser Ser Ser Thr Ala Tyr
        195                 200                 205

Met Gln Leu Ser Ser Leu Thr Ser Val Asp Ser Ala Val Tyr Phe Cys

```
                210              215              220
Ala Arg Ser Gly Leu Leu Arg Tyr Ala Met Asp Tyr Trp Gly Gln Gly
225                 230                 235                 240

Thr Ser Val Thr Val Ser Ser
                245

<210> SEQ ID NO 22
<211> LENGTH: 741
<212> TYPE: DNA
<213> ORGANISM: Artificial Sequence
<220> FEATURE:
<223> OTHER INFORMATION: Description of Artificial Sequence:  Synthetic
      Primer

<400> SEQUENCE: 22
gatattcaga tgacacagac tacatcctcc ctgtctgcct ctctgggaga cagagtcacc     60
gtcagttgca gggcaagtca ggacattagg aattatttaa actggtatca gcagaaacca    120
gacggaactg ttaaattcct gatctactac acatcaagat tacagccagg agtcccatca    180
aggttcagtg gcagtgggtc tggaacagat tattccctca ccattaacaa cctggagcag    240
gaagatattg cacttacttt tgccaacag ggcaatacgc ctccgtggac gttcggtgga    300
ggcaccaagc tggaaataaa acgtggtgga ggtggttctg atggtggtgg ttctggcggc    360
ggcggctccg gtggtggtgg atccgaggtc caactgcaac agtctggacc tgagctggtg    420
aagcctgggg cctcagtgaa gatttcctgc aaagattctg gctacgcatt caatagctct    480
tggatgaact gggtgaagca gaggcctgga cagggtcttg agtggattgg acggatttat    540
cctggagatg agattctaa ctacaatggg aaattcgagg caaggccat actgactgca    600 gacaaatcct ccagcacagc ctacatgcag ctcagcagcc tgacctctgt ggactctgcg    660
gtctatttct gtgcaagatc ggggttgcta cgttatgcta tggactactg ggtcaagga    720 acctcagtca ccgtctcctc g                                             741

<210> SEQ ID NO 23
<211> LENGTH: 247
<212> TYPE: PRT
<213> ORGANISM: Artificial Sequence
<220> FEATURE:
<223> OTHER INFORMATION: Description of Artificial Sequence:  Synthetic
      Peptide

<400> SEQUENCE: 23

Asp Ile Gln Met Thr Gln Thr Thr Ser Ser Leu Ser Ala Ser Leu Gly
1               5                   10                  15

Asp Arg Val Thr Val Ser Cys Arg Ala Ser Gln Asp Ile Arg Asn Tyr
            20                  25                  30

Leu Asn Trp Tyr Gln Gln Lys Pro Asp Gly Thr Val Lys Phe Leu Ile
        35                  40                  45

Tyr Tyr Thr Ser Arg Leu Gln Pro Gly Val Pro Ser Arg Phe Ser Gly
    50                  55                  60

Ser Gly Ser Gly Thr Asp Tyr Ser Leu Thr Ile Asn Asn Leu Glu Gln
65                  70                  75                  80

Glu Asp Ile Gly Thr Tyr Phe Cys Gln Gln Gly Asn Thr Pro Pro Trp
                85                  90                  95

Thr Phe Gly Gly Gly Thr Lys Leu Glu Ile Lys Arg Gly Gly Gly Gly
            100                 105                 110

Ser Asp Gly Gly Gly Ser Gly Gly Gly Gly Ser Gly Gly Gly Gly Ser
        115                 120                 125
```

```
Glu Val Gln Leu Gln Gln Ser Gly Pro Glu Leu Val Lys Pro Gly Ala
            130                 135                 140

Ser Val Lys Ile Ser Cys Lys Asp Ser Gly Tyr Ala Phe Asn Ser Ser
145                 150                 155                 160

Trp Met Asn Trp Val Lys Gln Arg Pro Gly Gln Gly Leu Glu Trp Ile
                165                 170                 175

Gly Arg Ile Tyr Pro Gly Asp Gly Asp Ser Asn Tyr Asn Gly Lys Phe
            180                 185                 190

Glu Gly Lys Ala Ile Leu Thr Ala Asp Lys Ser Ser Ser Thr Ala Tyr
        195                 200                 205

Met Gln Leu Ser Ser Leu Thr Ser Val Asp Ser Ala Val Tyr Phe Cys
    210                 215                 220

Ala Arg Ser Gly Leu Leu Arg Tyr Ala Met Asp Tyr Trp Gly Gln Gly
225                 230                 235                 240

Thr Ser Val Thr Val Ser Ser
                245

<210> SEQ ID NO 24
<211> LENGTH: 741
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 24
gatattcaga tgacacagac tacatcctcc ctgtctgcct ctctgggaga cagagtcacc      60
gtcagttgca gggcaagtca ggacattagg aattatttaa actggtatca gcagaaacca     120
gacggaactg ttaaattcct gatctactac acatcaagat tactgccagg agtcccatca     180
aggttcagtg gcagtgggtc tggaacagat tattccctca ccattaacaa cctggagcag     240
gaagatattg cacttacttt tgccaacagg gcaatacgc tccgtggac gttcggtgga      300 ggcaccaagc tggaaataaa acgtggtgga gtggttctg atggtggtgg ttctggcggc     360
ggcggctccg gtggtggtgg atccgaggtc caactgcaac agtctggacc tgagctggtg     420
aagcctgggg cctcagtgaa gatttcctgc aaagattctg gctacgcatt caatagctct     480
tggatgaact gggtgaagca gaggcctgga cagggtcttg agtggattgg acggatttat     540
cctggagatg gagattctaa ctacaatggg aaattcgagg gcaaggccat actgacagca     600
gacaaatcct ccagcacagc ctacatgcag ctcagcagcc tgacctctgt ggactctgcg     660
gtctatttct gtgcaagatc ggggttgcta cgttatgcta tggactactg ggtcaagga     720 acctcagtca ccgtctcctc g                                               741

<210> SEQ ID NO 25
<211> LENGTH: 247
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 25

Asp Ile Gln Met Thr Gln Thr Thr Ser Ser Leu Ser Ala Ser Leu Gly
  1               5                  10                  15

Asp Arg Val Thr Val Ser Cys Arg Ala Ser Gln Asp Ile Arg Asn Tyr
             20                  25                  30
```

```
Leu Asn Trp Tyr Gln Gln Lys Pro Asp Gly Thr Val Lys Phe Leu Ile
            35                  40                  45

Tyr Tyr Thr Ser Arg Leu Leu Pro Gly Val Pro Ser Arg Phe Ser Gly
        50                  55                  60

Ser Gly Ser Gly Thr Asp Tyr Ser Leu Thr Ile Asn Asn Leu Glu Gln
 65                  70                  75                  80

Glu Asp Ile Gly Thr Tyr Phe Cys Gln Gln Gly Asn Thr Pro Pro Trp
                85                  90                  95

Thr Phe Gly Gly Gly Thr Lys Leu Glu Ile Lys Arg Gly Gly Gly Gly
            100                 105                 110

Ser Asp Gly Gly Gly Ser Gly Gly Gly Ser Gly Gly Gly Gly Gly Ser
            115                 120                 125

Glu Val Gln Leu Gln Gln Ser Gly Pro Glu Leu Val Lys Pro Gly Ala
            130                 135                 140

Ser Val Lys Ile Ser Cys Lys Asp Ser Gly Tyr Ala Phe Asn Ser Ser
145                 150                 155                 160

Trp Met Asn Trp Val Lys Gln Arg Pro Gly Gln Gly Leu Glu Trp Ile
                165                 170                 175

Gly Arg Ile Tyr Pro Gly Asp Gly Asp Ser Asn Tyr Asn Gly Lys Phe
            180                 185                 190

Glu Gly Lys Ala Ile Leu Thr Ala Asp Lys Ser Ser Ser Thr Ala Tyr
            195                 200                 205

Met Gln Leu Ser Ser Leu Thr Ser Val Asp Ser Ala Val Tyr Phe Cys
        210                 215                 220

Ala Arg Ser Gly Leu Leu Arg Tyr Ala Met Asp Tyr Trp Gly Gln Gly
225                 230                 235                 240

Thr Ser Val Thr Val Ser Ser
                245

<210> SEQ ID NO 26
<211> LENGTH: 27
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 26
gctctagaat gaggaagaac cccatgg                                         27

<210> SEQ ID NO 27
<211> LENGTH: 28
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 27
ggcagatctg gctttacgat tggcgaaa                                        28

<210> SEQ ID NO 28
<211> LENGTH: 27
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 28
```

```
ggcagatctc acgcgcagat tcgcgtc                                         27

<210> SEQ ID NO 29
<211> LENGTH: 26
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 29
ggcagatctg ccgcgcaacg cttccc                                          26

<210> SEQ ID NO 30
<211> LENGTH: 27
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 30
ggcagatctc atgttgattt caccgaa                                         27

<210> SEQ ID NO 31
<211> LENGTH: 27
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 31
ggcagatctg ccatccattg ctgaggc                                         27

<210> SEQ ID NO 32
<211> LENGTH: 27
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 32
ggcagatctg gctggcgtgg tcgtgcc                                         27

<210> SEQ ID NO 33
<211> LENGTH: 34
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 33
ggcagatctg gaggtggaag cgaggcccag ccgg                                 34

<210> SEQ ID NO 34
<211> LENGTH: 32
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 34
ggaattcggc ccccgaggcc gatttgatct cg                                   32
```

```
<210> SEQ ID NO 35
<211> LENGTH: 33
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 35
cgaagcttag atctagtaaa ggagaagaac ttt                                33

<210> SEQ ID NO 36
<211> LENGTH: 28
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 36
ggaattcttt gtatagttca tccatgcc                                     28

<210> SEQ ID NO 37
<211> LENGTH: 43
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 37
gcactagtag atctcatatg gagcccgggc atccggggag ctc                    43

<210> SEQ ID NO 38
<211> LENGTH: 35
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 38
cgggcatccg gggagctcag gcccagccgg ccatg                             35

<210> SEQ ID NO 39
<211> LENGTH: 20
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 39
ggcgaattcg gcccccgagg                                              20

<210> SEQ ID NO 40
<211> LENGTH: 42
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 40
cgggcatccg gggagctcca atgagtaaag gagaagaact tt                     42
```

```
<210> SEQ ID NO 41
<211> LENGTH: 29
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 41
gcgaattctt tgtatagttc atccatgcc                                      29

<210> SEQ ID NO 42
<211> LENGTH: 51
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 42
ggcggtaccg aagatctgaa ggagatatac acatgtctgt agaagatact c             51

<210> SEQ ID NO 43
<211> LENGTH: 43
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 43
cctgacgggc ggttgaattt cttcttcagt tttttcgctt tct                      43

<210> SEQ ID NO 44
<211> LENGTH: 6
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 44

Cys Asp Gln Ser Ser Ser
 1               5

<210> SEQ ID NO 45
<211> LENGTH: 50
<212> TYPE: DNA
<213> ORGANISM: Artificial Sequence
<220> FEATURE:
<223> OTHER INFORMATION: Description of Artificial Sequence: Synthetic
      Primer
<220> FEATURE:
<221> NAME/KEY: modified_base
<222> LOCATION: (22)..(35)
<223> OTHER INFORMATION: n = a, c, g or t/u

<400> SEQUENCE: 45
cgaattctgc tggcaggttg cnnsnnsnns nnsnnsgagg cccagccggc               50

<210> SEQ ID NO 46
<211> LENGTH: 41
<212> TYPE: DNA
<213> ORGANISM: Artificial Sequence
<220> FEATURE:
<223> OTHER INFORMATION: Description of Artificial Sequence: Synthetic
      Primer
```

```
<400> SEQUENCE: 46
ggactgatgg atggctggcc ggaattctgc tggcaggttg c                          41

<210> SEQ ID NO 47
<211> LENGTH: 34
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 47
ggactgatgg atggtcgact gcggccgcga attc                                  34

<210> SEQ ID NO 48
<211> LENGTH: 34
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 48
ggactgatgg atgtacgaat tctagagaa ggag                                   34

<210> SEQ ID NO 49
<211> LENGTH: 32
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 49
ggactgatgg atggatttga tctcgagctt gg                                    32

<210> SEQ ID NO 50
<211> LENGTH: 6
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 50

Cys Asn Gly Glu Ser Ala
  1               5

<210> SEQ ID NO 51
<211> LENGTH: 6
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 51

Cys Thr His Leu Ser Gly
  1               5

<210> SEQ ID NO 52
<211> LENGTH: 6
<212> TYPE: PRT
<213> ORGANISM: Artificial Sequence
<220> FEATURE:
<223> OTHER INFORMATION: Description of Artificial Sequence: Synthetic
      Peptide
```

```
<400> SEQUENCE: 52

Cys Ser Arg Gly Ile Leu
 1               5

<210> SEQ ID NO 53
<211> LENGTH: 6
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 53

Cys Arg Glu Pro Met Ser
 1               5

<210> SEQ ID NO 54
<211> LENGTH: 6
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 54

Cys Ser Glu Leu Leu Arg
 1               5

<210> SEQ ID NO 55
<211> LENGTH: 6
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 55

Cys Glu Ser Leu Asn Ala
 1               5

<210> SEQ ID NO 56
<211> LENGTH: 6
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 56

Cys Gly Lys Leu Met Val
 1               5

<210> SEQ ID NO 57
<211> LENGTH: 6
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 57

Cys Gly Pro Gly Ser His
 1               5

<210> SEQ ID NO 58
<211> LENGTH: 6
```

```
-continued

<212> TYPE: PRT
<213> ORGANISM: Artificial Sequence
<220> FEATURE:
<223> OTHER INFORMATION: Description of Artificial Sequence:  Synthetic
      Peptide

<400> SEQUENCE: 58

Cys Tyr Lys Ser Thr Thr
 1               5

<210> SEQ ID NO 59
<211> LENGTH: 6
<212> TYPE: PRT
<213> ORGANISM: Artificial Sequence
<220> FEATURE:
<223> OTHER INFORMATION: Description of Artificial Sequence:  Synthetic
      Peptide

<400> SEQUENCE: 59

Cys Leu Ala Leu Val Gln
 1               5

<210> SEQ ID NO 60
<211> LENGTH: 6
<212> TYPE: PRT
<213> ORGANISM: Artificial Sequence
<220> FEATURE:
<223> OTHER INFORMATION: Description of Artificial Sequence:  Synthetic
      Peptide

<400> SEQUENCE: 60

Cys Met Leu Ser Ser Thr
 1               5

<210> SEQ ID NO 61
<211> LENGTH: 6
<212> TYPE: PRT
<213> ORGANISM: Artificial Sequence
<220> FEATURE:
<223> OTHER INFORMATION: Description of Artificial Sequence:  Synthetic
      Peptide

<400> SEQUENCE: 61

Cys Val Leu Leu Tyr Ser
 1               5
```

SELECTION OF BACTERIAL INNER-MEMBRANE ANCHOR POLYPEPTIDES

This application claims the priority of U.S. Provisional Patent App. No. 60/554,324, filed Mar. 18, 2004, and is a continuation-in-part of U.S. patent application Ser. No. 10/620,278, filed Jul. 15, 2003, now U.S. Pat. 7,094,571, which claims the priority of U.S. Provisional Patent App. No. 60/396,058, filed Jul. 15, 2002.

This invention was made with government support under TransTexas BW Defense Initiative Grant No. DAA21-93C-0101 awarded by the United States Department of Defense, contract number DADD17-01-D-0001 awarded by the United States Army Research Laboratory, the United States Army ARO MURI program, and the Texas Consortium for Development of Biological Sensors. The government has certain right in the invention.

BACKGROUND OF THE INVENTION

1. Field of the Invention

The present invention relates generally to the field of protein engineering. More particularly, it concerns methods for identification of bacterial inner membrane anchor sequences.

2. Description of Related Art

The isolation of polypeptides that either bind to ligands with high affinity and specificity or catalyze the enzymatic conversion of a reactant (substrate) into a desired product is a key process in biotechnology. Ligand-binding polypeptides, including proteins and enzymes with a desired substrate specificity can be isolated from large libraries of mutants, provided that a suitable screening method is available. Small protein libraries composed of $10^3$-$10^5$ distinct mutants can be screened by first growing each clone separately and then using a conventional assay for detecting clones that exhibit specific binding. For example, individual clones expressing different protein mutants can be grown in microtiter well plates or separate colonies on semisolid media such as agar plates. To detect binding the cells are lysed to release the proteins and the lysates are transferred to nylon filters, which are then probed using radiolabeled or fluorescently labeled ligands (DeWildt et al. 2000). However, even with robotic automation and digital image systems for detecting binding in high density arrays, it is not feasible to screen large libraries consisting of tens of millions or billions of clones. The screening of libraries of that size is required for the de novo isolation of enzymes or protein binders that have affinities in the sub-nanomolar range.

The screening of very large protein libraries has been accomplished by a variety of techniques that rely on the display of proteins on the surface of viruses or cells (Ladner et al. 1993). The underlying premise of display technologies is that proteins engineered to be anchored on the external surface of biological particles (i.e., cells or viruses) are directly accessible for binding to ligands without the need for lysing the cells. Viruses or cells displaying proteins with affinity for a ligand can be isolated in a variety of ways including sequential adsorption/desorption form immobilized ligand, by magnetic separations or by flow cytometry (Ladner et al. 1993, U.S. Pat. No. 5,223,409, Ladner et al. 1998, U.S. Pat. No. 5,837,500, Georgiou et al. 1997, Shusta et al. 1999).

The most widely used display technology for protein library screening applications is phage display. Phage display is a well-established and powerful technique for the discovery of proteins that bind to specific ligands and for the engineering of binding affinity and specificity (Rodi and Makowski, 1999). In phage display, a gene of interest is fused in-frame to phage genes encoding surface-exposed proteins, most commonly pIII. The gene fusions are translated into chimeric proteins in which the two domains fold independently. Phage displaying a protein with binding affinity for a ligand can be readily enriched by selective adsorption onto immobilized ligand, a process known as "panning". The bound phage is desorbed from the surface, usually by acid elution, and amplified through infection of E. coli cells. Usually, 4-6 rounds of panning and amplification are sufficient to select for phage displaying specific polypeptides, even from very large libraries with diversities up to $10^{10}$. Several variations of phage display for the rapid enrichment of clones displaying tightly binding polypeptides have been developed (Duenas and Borrebaeck, 1994; Malmborg et al., 1996; Kjaer et al., 1998; Burioni et al., 1998; Levitan, 1998; Mutuberria et al., 1999; Johns et al., 2000).

However, several spectacular successes notwithstanding, the screening of phage-displayed libraries can be complicated by a number of factors. First, phage display imposes minimal selection for proper expression in bacteria by virtue of the low expression levels of antibody fragment gene III fusion necessary to allow phage assembly and yet sustain cell growth (Krebber et al., 1996, 1997). As a result, the clones isolated after several rounds of panning are frequently difficult to produce on a preparative scale in E. coli. Second, although phage displayed proteins may bind a ligand, in some cases their un-fused soluble counterparts may not (Griep et al., 1999). Third, the isolation of ligand-binding proteins and more specifically antibodies having high binding affinities can be complicated by avidity effects by virtue of the need for gene III protein to be present at around 5 copies per virion to complete phage assembly. Even with systems that result in predominantly monovalent protein display, there is nearly always a small fraction of clones that contain multiple copies of the protein. Such clones bind to the immobilized surface more tightly and are enriched relative to monovalent phage with higher affinities (Deng et al., 1995; MacKenzie et al., 1996, 1998). Fourth, theoretical analysis aside (Levitan, 1998), panning is still a "black box" process in that the effects of experimental conditions, for example the stringency of washing steps to remove weakly or non-specifically bound phage, can only be determined by trial and error based on the final outcome of the experiment. Finally, even though pIII and to a lesser extent the other proteins of the phage coat are generally tolerant to the fusion of heterologous polypeptides, the need to be incorporated into the phage biogenesis process imposes biological constraints that can limit library diversity. Therefore, there is a great need in the art for techniques capable of overcoming these limitations.

The deficiencies of prior art library screening techniques may be overcome by use of novel methods for isolating binding polypeptides such as anchored periplasmic expression (APEx). With this technique, libraries of polypeptide (e.g., antibody or other binding polypeptides) mutants can be constructed and expressed on the outerface of the inner membrane of Gram negative bacteria and screened for the ability to bind to target ligands. By removal of the outer membrane, target ligands and/or detection reagents of nearly unlimited size may be used. While anchor sequences for use in such techniques have been known, methods have not generally been available for the efficient isolation of new anchor sequences for the bacterial inner membrane. There is, therefore, a great need in the art for efficient methods for the selection of new inner membrane anchor sequences.

SUMMARY OF THE INVENTION

In one aspect, the invention provides a method of obtaining a bacterium comprising a nucleic acid sequence encoding an inner membrane anchor polypeptide capable of anchoring a heterologous polypeptide to the outer side of the inner membrane of a Gram negative bacterium comprising the steps of: (a) providing a Gram negative bacterium comprising an inner membrane, an outer membrane and a periplasm; the bacterium comprising a nucleic acid sequence encoding a fusion between a heterologous polypeptide and a candidate inner membrane anchor sequence; (b) removing the outer membrane; and (c) selecting the bacterium based on the presence of the heterologous polypeptide anchored to the outer side of the inner membrane to identify an inner membrane anchor polypeptide capable of anchoring a heterologous polypeptide to the outer side of the inner membrane of the bacterium. In one embodiment, the method may be further defined as a method of obtaining a nucleic acid sequence encoding an inner membrane anchor sequence capable of anchoring a heterologous polypeptide to the outer side of the inner membrane, the method further comprising the step of: (d) cloning a nucleic acid sequence encoding the inner membrane anchor polypeptide. Selecting the bacterium may comprise detecting the heterologous polypeptide with a binding polypeptide having specific affinity for the heterologous polypeptide. This may further comprise use of at least a second binding polypeptide having affinity for the heterologous polypeptide and/or the binding polypeptide having specific affinity for the heterologous polypeptide. The second binding polypeptide may be an antibody or fragment thereof, which may be fluorescently or otherwise labeled. Selecting the bacterium may comprise use of at least a third binding polypeptide having specific affinity for the heterologous polypeptide and/or the second binding polypeptide to label the bacterium.

In one embodiment of the method, the heterologous polypeptide may comprise a detectable label. Examples of detectable labels include an antigen and GFP. The heterologous polypeptide may also comprise an antibody or fragment thereof. Selecting the bacterium may comprise detecting the antibody or fragment thereof with a labeled ligand having specific affinity for the antibody or fragment thereof. In one embodiment, the Gram negative bacterium is an *E. coli* bacterium.

In further embodiments of the invention, step (a) is further defined as comprising providing a population of Gram negative bacteria. The population of bacteria may be further defined as collectively expressing a plurality of candidate inner membrane anchor sequences. From about two to six rounds of selecting may be carried out to obtain the bacterium from the population. The bacterium may be viable or nonviable. Cloning may comprise amplification of the nucleic acid sequence. Selecting may be carried out by flow-cytometry or magnetic separation. The nucleic acid encoding a candidate inner membrane anchor polypeptide may be flanked by known PCR primer sites. The candidate inner membrane anchor polypeptide may be anchored to the outer side of the inner membrane with a transmembrane protein or fragment thereof. The transmembrane protein or fragment thereof may comprise a sequence selected from the group consisting of: the first two amino acids encoded by the *E. coli* NlpA gene, the first six amino acids encoded by the *E. coli* NlpA gene, the gene III protein of filamentous phage or a fragment thereof, an inner membrane lipoprotein or fragment thereof. The candidate inner membrane anchor polypeptide may be anchored via an N- or C-terminus of the polypeptide. In the method, the candidate inner membrane anchor polypeptide sequence may be anchored to the outer side of the inner membrane with an inner membrane lipoprotein or fragment thereof selected from the group consisting of: AraH, MglC, MalF, MalG, Mal C, MalD, RbsC, RbsC, ArtM, ArtQ, GlnP, ProW, HisM, HisQ, LivH, LivM, LivA, Liv E, Dpp B, DppC, OppB, AmiC, AmiD, BtuC, FhuB, FecC, FecD, FecR, FepD, NikB, NikC, CysT, CysW, UgpA, UgpE, PstA, PstC, PotB, PotC, PotH, PotI, ModB, NosY, PhnM, LacY, SecY, TolC, DsbB, DsbD, TonB, TatC, CheY, TraB, Exb D, ExbB and Aas.

In another aspect, the invention provides a method of obtaining a bacterium comprising a nucleic acid sequence encoding an inner membrane anchor polypeptide capable of anchoring a heterologous polypeptide to the outer side of the inner membrane of a Gram negative bacterium comprising the steps of: (a) providing a population of Gram negative bacteria the members of which comprise an inner membrane, an outer membrane and a periplasm; wherein the bacteria collectively comprise nucleic acid sequences encoding fusion polypeptides between a heterologous polypeptide and a plurality of candidate inner membrane anchor sequences; (b) removing the outer membrane; and (c) selecting the bacterium from the population based on the presence of the heterologous polypeptide anchored to the outer side of the inner membrane to identify an inner membrane anchor polypeptide capable of anchoring a heterologous polypeptide to the outer side of the inner membrane of the bacterium. In the method, step (c) may be further defined as selecting a subpopulation of bacteria comprising the heterologous polypeptide anchored to the outer side of the inner membrane. Step (c) may also comprise fluorescently labeling the heterologous polypeptide followed by fluorescence activated cell sorting (FACS).

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIG. 1A-C: Selective identification of Antigen targets with APEx. APEx expressed scFvs in *E. coli* represented as indicated. Shows scFvs expressed that bind small molecules, (FIG. 1A) digoxigenin-Bodipy FL, (FIG. 1B) methamphetamine-FL; or ScFvs expressed that bind peptides (FIG. 1C) e.g., peptide 18aa.

FIG. 2A-B: Detection of ScFvs on the Surface of Spheroplasts. APEx expressed scFvs in *E. coli* represented as indicated. ScFvs expressed were capable of binding large antigens, e.g., PA-Cy5 (83 kD), Phycoerythrin-digoxigenin (240 kD). Provides evidence that scFvs expressed via APEx are accessible to large proteins.

(FIG. 7A) Fluorescence distribution of ABLEC™ cells expressing PA specific (14B7) and digoxigenin specific (Dig) scFv and labeled with 200 nM Bodipy™ conjugated fluorescent antigens. Histograms represent the mean fluorescence intensity of 10,000 E. Coli events. (FIG. 7B) Histograms of cells expressing 14B7 or Dig scFv labeled with 200 nM of the 240 kDa digoxigenin-phycoerythrin conjugate.

(FIG. 8B) Table of affinity data acquired by SPR. (FIG. 8C) FC Histogram of anti-PA scFv in pAPEx1 expressed in E. coli and labeled with 200 nM PA-Bodipy™ conjugate as compared with anti-methamphetamine (Meth) scFv negative control.

(FIG. 9A) Anti-digoxigenin Dig scfv, anti-PA M18 scFv and anti-methamphetamine Meth scFv expressed as N-terminal fusions in the pAPEx1 vector in E. coli specifically label with 200 nM of their respective antigen. (FIG. 9B) C-terminal fusions of same scFv in pAK200 vector specifically labeled with 200 nM of their respective antigen.

FIG. 11: Alignment of 14B7 scFv (SEQ ID NO:21) and M18 scFv (SEQ ID NO:23) sequences showing variable heavy and variable light chains and mutations made to improve binding affinity.

DESCRIPTION OF ILLUSTRATIVE EMBODIMENTS

Figure 3A:
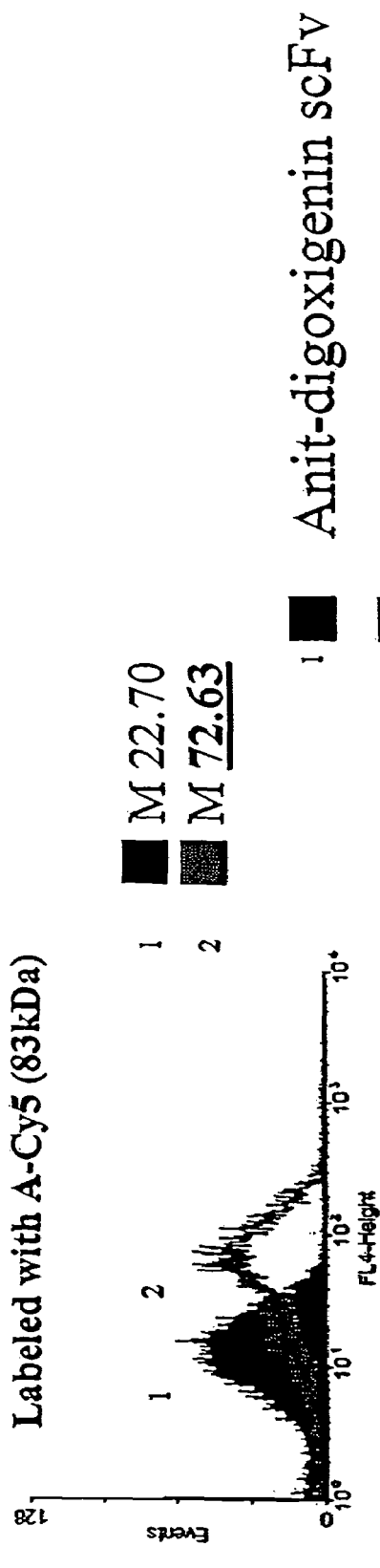
FIG. 3A-B: Detection of ScFvs for Larger Target Antigen conjugated fluorophores.

The invention overcomes the limitations of the prior art by providing a novel method for isolating polypeptides capable of anchoring heterologous polypeptides to the bacterial inner membrane. In one embodiment of the technique, libraries of candidate anchor polypeptides are expressed as fusions with heterologous polypeptides capable of being detected on the outer face of the bacterial inner membrane. In bacteria that express a functional anchor sequence, the heterologous polypeptide is bound to outer face of the inner membrane. Bacteria with the functional anchor sequence can subsequently be identified based on the presence of the heterologous polypeptide, for example, by removing the outer membrane to remove unanchored heterologous polypeptide followed by detection of the anchored polypeptide. Such bacteria may be detected in any suitable manner, including use of direct fluorescence or secondary antibodies. Fluorescent labeling allows implementation of efficient techniques such as fluorescence activated cell sorting (FACS). Identification of additional anchors is desirable in that particular anchors may function more efficiently with certain polypeptides being bound to the inner membrane due to, for example, stearic or other characteristics of the polypeptide relative to the anchor and inner membrane. The anchor may also affect the efficiency with which a target ligand bound to a candidate binding protein is detected. For example, the anchor may vary the degree to which an antigen on a bound target ligand is exposed for detection with a labeled antibody or other detection agent.

The display of heterologous proteins on microbial scaffolds has attractive applications in many different areas including vaccine development, bioremediation and protein engineering. In Gram negative bacteria there have been display systems designed such that, by virtue of a N or C terminal chimera fusion, proteins are displayed to the cell surface. Although there have been many different strategies used to direct protein localization, including fusions to outer membrane proteins, lipoproteins, surface structural proteins and leader peptides, many share the same limitations. One limitation is the size of the protein which can be displayed. Many display scaffolds can only tolerate a few hundred amino acids, which significantly limits the scope of proteins which can be displayed. Also, display implies that the protein of interest is situated such that it can interact with its environment, yet the major limitation of many of these systems is that the architecture of the outer surface of gram negative bacteria and in particular the presence of lipopolysaccharide (LPS) molecules having steric limitations that inhibit the binding of externally added ligands. Another limitation arises from the requirement that the displayed protein is localized on the external surface of the outer membrane. For this purpose the polypeptide must first be secreted across the cytoplasmic membrane must then transverse the periplasmic space and finally it must be assemble properly in the outer membrane. A heterologous polypeptide may be any type of detectable molecule.

In accordance with the invention, the limitations of the prior techniques can be overcome by the identification and use of anchor polypeptides to display proteins anchored to the outer surface of the inner membrane. It was demonstrated using the technique that, by utilizing conditions that permeabilize the outer membrane, E. coli expressing inner membrane anchored scFv antibodies (approx. 30 kDa in size) can be labeled with a target antigen conjugated, for example, to a fluorophore and can subsequently be used to sort protein libraries utilizing flow cytometry for isolation of gain of function mutants.

Following disruption of the outer bacterial membrane, which is well known to those of skill in the art and may comprise, for example, use of Tris-EDTA-lysozyme, labeled antigens with sizes up to at least 240 kDa can be used to detect anchored polypeptides. With fluorescent labeling, cells comprising functional anchors may be isolated by flow cytometry and the DNA of isolated clones rescued by PCR. In one embodiment of the invention, anchored molecules are labeled with fluorescent dyes. Thus, bacterial clones expressing polypeptides fused to a functional inner membrane anchor are labeled with a fluorescently labeled molecule having specific affinity for the polypeptide on the face of the bacterial inner membrane. The term "specific affinity" refers to an association that is specific to a particular set of molecules and not general to, for example, all proteins within a cell. An example of specific affinity is the relationship between an antibody or fragment thereof and a given antigen.

The polypeptide bound on the inner membrane may itself be a ligand and/or a binding protein. The fluorescent bacteria expressing functional anchors can then be enriched from the population using automated techniques such as flow cytometry, including FACS. Candidate anchor sequences screened in accordance with the invention may be selected for likely function as an inner membrane protein or may be random sequences. Benefit may be obtained by screening of transmembrane or polytropic membrane polypeptides and fragments thereof.

As used herein, an inner membrane anchor polypeptide refers to any peptide sequence that causes a polypeptide to associate with and become bound to the outer face of the inner membrane. The inner membrane anchor polypeptide need not permanently bind to the inner membrane, but the association should be sufficiently strong to allow removal of the outer membrane while maintaining anchoring on the outer face of the inner membrane.

The periplasm comprises the space defined by the inner and outer membranes of a Gram-negative bacterium. In wild-type E. coli and other Gram negative bacteria, the outer membrane serves as a permeability barrier that severely restricts the diffusion of molecules greater than 600 Da into the periplasmic space (Decad and Nikado, 1976). Conditions that increase the permeability of the outer membrane, allowing larger molecules to diffuse in the periplasm, have two deleterious effects in terms of the ability to screen libraries: (a) the cell viability is affected to a significant degree and (b) the diffusion of molecules into the cell is accompanied by the diffusion of proteins and other macromolecules.

The inventors have identified techniques that allow fluorescent conjugates of ligands and polypeptides to pass the outer membrane and bind to proteins and remain bound to the inner membrane. Therefore, in bacterial cells expressing functional anchors, the heterologous polypeptide can be detected, allowing the bacteria to be isolated from the rest of the library. By "heterologous", it is understood that a given polypeptide need not be from a source other than the host cell, but will be in a genetic arrangement other than that of the wild type host genome. Where fluorescent labeling of the target ligand is used, cells may efficiently be isolated by flow cytometry (fluorescence activated cell sorting (FACS)). With this approach, existing libraries of expressed fusion proteins in bacteria can be easily tested without the need for subcloning into a phage or outer cell surface display systems.

Periplasmic expression may also be carried out in accordance with the invention by expression in soluble form. Techniques for soluble expression in the periplasm and screening of candidate binding proteins that may be used in accordance with the invention are described in detail in U.S. patent application Ser. No. 09/699,023, filed Oct. 27, 2000, the entire disclosure of which is specifically incorporated herein by reference.

The periplasmic compartment is contained between the inner and outer membranes of Gram negative cells (see, e.g., Oliver, 1996). As a sub-cellular compartment, it is subject to variations in size, shape and content that accompany the growth and division of the cell. Within a framework of peptidoglycan heteropolymer is a dense milieu of periplasmic proteins and little water, lending a gel-like consistency to the compartment (Hobot et al., 1984; van Wielink and Duine, 1990). The peptidoglycan is polymerized to different extents depending on the proximity to the outer membrane, close-up it forms the murein sacculus that affords cell shape and resistance to osmotic lysis.

The outer membrane (see Nikaido, 1996) is composed of phospholipids, porin proteins and, extending into the medium, lipopolysaccharide (LPS). The molecular basis of outer membrane integrity resides with LPS ability to bind divalent cations (Mg2+ and Ca2+) and link each other electrostatically to form a highly ordered quasi-crystalline ordered "tiled roof" on the surface (Labischinski et al., 1985). The membrane forms a very strict permeability barrier of allowing passage of molecules no greater than around 650 Da (Burman et al., 1972; Decad and Nikaido, 1976) via the porins. The large water filled porin channels are primarily responsible for allowing free passage of mono and disaccharides, ions and amino acids in to the periplasm compartment (Naeke, 1976; Nikaido and Nakae, 1979; Nikaido and Vaara, 1985). However, detection agents can diffuse into the periplasm. Such diffusion can be aided by one or more treatments of a bacterial cell, thereby rendering the outer membrane more permeable as is described herein.

I. Anchored Periplasmic Expression

Prior art methods of both phage display and bacterial cell surface display suffer from a limitation in that the protein is required, by definition, to be physically displayed on the outer surface of the vehicle used, to allow unlimited access to the targets (immobilized for phage or fluorescently conjugated ligands for flow cytometry) (U.S. Pat. No. 5,223,409, the disclosure of which is specifically incorporated herein by reference in its entirety). However, certain proteins are known to be poorly displayed on phage (Maenaka et al., 1996; Corey et al., 1993) and the toxic effects of outer cell surface display have been treated at length (Daugherty et al., 1999). Further, there is no lipopolysaccharide to interfere with binding on the inner membrane.

Herein, the inventors have described a technique in which proteins can be expressed on the periplasmic face of the inner membrane as fusion proteins yet still be accessible to relatively large ligands. As used herein, the term "polypeptide" includes antibodies, fragments of antibodies, as well as any other peptides, including proteins potentially capable of binding a given target molecule. The antibody or other binding peptides may be expressed with the invention as fusion polypeptides with polypeptides capable of serving as anchors to the periplasmic face of the inner membrane. Such a technique may be termed "Anchored Periplasmic Expression" or "APEx".

The outer membrane forms a very strict permeability barrier allowing passage of molecules no greater than around 650 Da (Burman et al., 1972; Decad and Nikaido, 1976) via the porins. However, the inventors have shown that ligands greater than 2000 Da in size can diffuse into the periplasm without disruption of the periplasmic membrane. Such diffusion can be aided by one or more treatments of a bacterial cell, thereby rendering the outer membrane more permeable, or by removal of the outer membrane as described below.

A fusion polypeptide comprising a candidate anchor sequence may further comprise any second detectable polypeptide. It will be preferable that the second polypeptide is readily detectable when anchored to the outer face of the inner membrane. The polypeptide may comprise a label that is directly detectable, such as a fluorophore including GFP, or with secondarily detectable agents such as an antigen or binding protein that can be detected by contacting with labeled binding protein or antigen. The fusion may comprise a linker polypeptide serving to link the candidate anchor polypeptide and the second polypeptide. A general scheme behind the invention comprises the advantageous expression of a heterogeneous collection of candidate anchors to identify functional anchor polypeptides having desirable characteristics for the display of various molecules on the outer face of the inner membrane.

The candidate anchor may comprise a random sequence or may be selected for likely ability to serve as an anchor sequence. An example of potential sequences for use as candidate anchors include lipoproteins from *E. coli* and other Gram negative bacteria. Generally all that is required is a signal sequence and an arginine at amino acid 2 position to serve as an anchor. Such candidate anchor sequences may therefore comprise a periplasm sec signal sequence followed by the sec cleavage region and coding for cysteine as amino acid 1 and arginine as amino acid 2 of the mature protein. Such a sequence may further be attached to other candidate sequences for screening. Transmembrane proteins and fragments thereof could also potentially be used as candidate anchors, although this may require a larger fusion construct.

Examples of sequences for use as candidate anchors include fragments, mutants and full length sequences of lipoproteins such as Pullulanase of *K. pneumoniae*, phage encoded celB, and *E. coli* acrE (envC), as well as inner membrane proteins such as AraH, MglC, MalF, MalG, Mal C, MalD, RbsC, RbsC, ArtM, ArtQ, GlnP, ProW, HisM, HisQ, LivH, LivM, LivA, Liv E, Dpp B, DppC, OppB, AmiC, AmiD, BtuC, FhuB, FecC, FecD, FecR, FepD, NikB, NikC, CysT, CysW, UgpA, UgpE, PstA, PstC, PotB, PotC, PotH, PotI, ModB, NosY, PhnM, LacY, SecY, TolC, DsbB, DsbD, TonB, TatC, CheY, TraB, Exb D, ExbB and Aas. Single transmembrane loops of any cytoplasmic protein can also be used as a candidate membrane anchor.

The preparation of diverse populations of fusion proteins in the context of phage display is known (see, e.g., U.S. Pat. No. 5,571,698). Similar techniques may be employed with the instant invention to prepare candidate inner membrane anchor sequences. Such fusions can be mutated to form a library of structurally related fusion proteins that can be screened for function as an anchor in accordance with the invention. As such, techniques for the creation of heterogeneous collections of candidate molecules which are well known to those of skill in the art in conjunction with phage display, can be adapted for use with the invention. Those of skill in the art will recognize that such adaptations will include the use of bacterial elements for expression of fusion proteins comprising candidate anchor sequences, including promoters, enhancers and leader sequences. The current invention provides the advantage relative to phage display of not requiring the use of phage or expression of molecules on the outer cell surface, which may be poorly expressed or may be deleterious to the host cell.

Methods for creation of fusion proteins are well known to those of skill in the art (see, for example, U.S. Pat. No. 5,780,279). One means for doing so comprises constructing a gene fusion between a candidate anchor polypeptide and a second polypeptide by mutating a starting candidate anchor sequence, thereby generating a family of mutants. Those sequences having desired levels of function as an anchor can then be selected from large populations of bacteria expressing the family of mutants. Those bacteria in which a selected anchor polypeptide is expressed, can then be isolated and the corresponding nucleic acid encoding the anchor can be cloned.

II. Permeabilization and/or Removal of the Outer Membrane

In one embodiment of the invention, methods are employed for increasing the permeability of the outer membrane to one or more detection agent(s) and/or removing the outer membrane. This can be used to improve detection of polypeptides on the face of the inner membrane indicating function of a given inner membrane anchor sequence. Conditions have been identified that lead to the permeation of ligands into the periplasm without loss of viability or release of the expressed proteins from the cells, but the invention may be carried out without maintenance of the outer membrane. By serving as an anchor to the outer side of the inner (cytoplasmic) membrane in a fusion polypeptides, a candidate anchor will be detectable on the face of the inner membrane following removal of the outer membrane. As a result, only those cells expressing functional anchor sequences can be selected among a population of candidate anchor sequences.

The permeability of the outer membrane of different strains of bacterial hosts can vary widely. It has been shown previously that increased permeability due to OmpF overexpression was caused by the absence of a histone like protein resulting in a decrease in the amount of a negative regulatory mRNA for OmpF translation (Painbeni et al., 1997). Also, DNA replication and chromosomal segregation is known to rely on intimate contact of the replisome with the inner membrane, which itself contacts the outer membrane at numerous points. A preferred host for library screening applications is *E. coli* ABLE™C strain, which additionally has mutations that reduce plasmid copy number.

Treatments such as hyperosmotic shock can improve permeability significantly. It is known that many agents including, calcium ions (Bukau et al., 1985) and even Tris buffer (Irvin et al., 1981) alter the permeability of the outer-membrane. Further, phage infection also affects permeability. Both the filamentous phage inner membrane protein pIII and the large multimeric outer membrane protein pIV can alter membrane permeability (Boeke et al., 1982) with mutants in pIV known to improve access to maltodextrins normally excluded (Marciano et al., 1999). Using combinations of strain, salt and phage, a high degree of permeability can be achieved (Daugherty et al., 1999).

Cells comprising anchored polypeptides bound to fluorescently labeled ligands can then be easily isolated from cells that express binding proteins without affinity for the labeled ligand using flow cytometry or other related techniques. However, it will typically be desired to use less disruptive techniques in order to maintain the viability of cells. EDTA and Lysozyme treatments may be useful for removal of the outer membrane in particular.

III. Screening Candidate Molecules

Candidate anchor sequences may comprise large libraries of diverse candidate substances, or, alternatively, may comprise particular classes of sequences selected with an eye towards structural attributes that are believed to make them more likely to function as an inner membrane anchor. To identify a candidate molecule capable of serving as an anchor in accordance with the invention, one may carry out the steps of: providing a population of Gram negative bacterial cells comprising fusion proteins between candidate anchor sequences and a heterologous polypeptide and allowing the fusion protein to be expressed; removing the outer membrane to remove unanchored polypeptide; and detecting the presence of the heterologous polypeptide on the surface of the inner membrane of bacteria expressing a functional anchor sequence. The anchor can then be cloned from the bacteria.

In the aforementioned method, the function of an anchor will prevent diffusing out of the cell. Labeling may then be used to isolate the cell expressing a sequence serving as an inner membrane anchor, and in this way, the sequence encoding the anchor polypeptide isolated. The anchor may be used, for example, in techniques such as anchored periplasmic expression.

As used herein the term "candidate inner membrane anchor" refers to any polypeptide capable of functioning as a sequence capable of anchoring heterologous polypeptides to the outer face of the bacteria inner membrane. Such a sequences may be particularly designed for the likelihood that it will function as an inner membrane anchor.

A. Cloning of Anchor Sequences

After a bacterial cell is identified that produces an inner membrane anchor with the desired function, the corresponding coding sequence may be cloned. In this manner, DNA encoding the anchor can be isolated and sequenced using conventional procedures (e.g., by using oligonucleotide probes that are capable of binding specifically to genes encoding the anchor).

Once isolated, the anchor may be placed into expression vectors, which can then transfected into bacterial host cells for the display of polypeptides on the inner membrane. The DNA may be modified, for example, by substituting codons and adding linker or leader peptides as desired. In that manner, "chimeric" or "hybrid" anchor polypeptides are prepared that have the desired function.

It will be understood by those of skill in the art that nucleic acids may be cloned from viable or non-viable cells. In the case of nonviable cells, for example, it may be desired to use amplification of the cloned DNA, for example, using PCR. This may also be carried out using viable cells either with or without further growth of cells.

B. Labeled Ligands

In one embodiment of the invention, a candidate anchor sequence may be fused to a binding protein that is detected with a labeled ligand, or alternatively, may be fused to a ligand and detected with a labeled binding protein. By permeabilization and/or removal of the periplasmic membrane of a Gram negative bacterium in accordance with the invention, labeled ligands and binding proteins of potentially any size may be used. In the absence of removal of the periplasmic membrane, it will typically be preferable that reagents of less than 50,000 Da in size be used in order to allow efficient diffusion of the ligand across the bacterial periplasmic membrane.

Labeled ligands or antibodies used to detect a given polypeptide can be prepared, for example, by linking the ligand or binding protein to at least one detectable agent to form a conjugate. For example, it is conventional to link or covalently bind or complex at least one detectable molecule or moiety. A "label" or "detectable label" is a compound and/or element that can be detected due to specific functional properties, and/or chemical characteristics, the use of which allows the compound to which it is attached to be detected, and/or further quantified if desired. Examples of labels which could be used with the invention include, but are not limited to, enzymes, radiolabels, haptens, fluorescent labels, phosphorescent molecules, chemiluminescent molecules, chromophores, luminescent molecules, photoaffinity molecules, colored particles or ligands, such as biotin.

In one embodiment of the invention, a visually-detectable marker is used such that automated screening of cells for the label can be carried out. In particular, fluorescent labels are beneficial in that they allow use of flow cytometry for isolation of cells expressing a desired binding protein or antibody.

Examples of agents that may be detected by visualization with an appropriate instrument are known in the art, as are methods for their attachment to a desired ligand (see, e.g., U.S. Pat. Nos. 5,021,236; 4,938,948; and 4,472,509, each incorporated herein by reference). Such agents can include paramagnetic ions; radioactive isotopes; fluorochromes; NMR-detectable substances and substances for X-ray imaging. Types of fluorescent labels that may be used with the invention will be well known to those of skill in the art and include, for example, Alexa 350, Alexa 430, AMCA, BODIPY 630/650, BODIPY 650/665, BODIPY-FL, BODIPY-R6G, BODIPY-TMR, BODIPY-TRX, Cascade Blue, Cy3, Cy5,6-FAM, Fluorescein Isothiocyanate, HEX, 6-JOE, Oregon Green 488, Oregon Green 500, Oregon Green 514, Pacific Blue, REG, Rhodamine Green, Rhodamine Red, Renographin, ROX, TAMRA, TET, Tetramethylrhodamine, and/or Texas Red.

Magnetic screening techniques are well known to those of skill in the art (see, for example, U.S. Pat. No. 4,988,618, U.S. Pat. No. 5,567,326 and U.S. Pat. No. 5,779,907). Examples of paramagnetic ions that could be used as labels in accordance with such techniques include ions such as chromium (III), manganese (II), iron (III), iron (II), cobalt (II), nickel (II), copper (II), neodymium (III), samarium (III), ytterbium (III), gadolinium (III), vanadium (II), terbium (III), dysprosium (III), holmium (III) and/or erbium (III). Ions useful in other contexts include but are not limited to lanthanum (III), gold (III), lead (II), and especially bismuth (III).

Another type of detection reagent contemplated in the present invention are those linked to a secondary binding molecule and/or to an enzyme (an enzyme tag) that will generate a colored product upon contact with a chromogenic substrate. Examples of such enzymes include urease, alkaline phosphatase, (horseradish) hydrogen peroxidase or glucose oxidase. In such instances, it will be desired that cells selected remain viable. Preferred secondary binding agents are biotin and/or avidin and streptavidin compounds. The use of such labels is well known to those of skill in the art and are described, for example, in U.S. Pat. Nos. 3,817,837; 3,850, 752; 3,939,350; 3,996,345; 4,277,437; 4,275,149 and 4,366, 241; each incorporated herein by reference.

Molecules containing azido groups also may be used to form covalent bonds to proteins through reactive nitrene intermediates that are generated by low intensity ultraviolet light (Potter & Haley, 1983). In particular, 2- and 8-azido analogues of purine nucleotides have been used as site-directed photoprobes to identify nucleotide-binding proteins in crude cell extracts (Owens & Haley, 1987; Atherton et al., 1985). The 2- and 8-azido nucleotides have also been used to map nucleotide-binding domains of purified proteins (Khatoon et al., 1989; King et al., 1989; and Dholakia et al., 1989) and may be used as binding agents.

Labeling can be carried out by any of the techniques well known to those of skill in the art. For instance, ligands and binding proteins can be labeled by contacting with the desired label and a chemical oxidizing agent such as sodium hypochlorite, or an enzymatic oxidizing agent, such as lactoperoxidase. Similarly, an exchange process could be used. Alternatively, direct labeling techniques may be used, e.g., by incubating with the label, a reducing agent such as $SNCl_2$, a buffer solution such as sodium-potassium phthalate solution, and the agent to be labeled. Intermediary functional groups could also be used, for example, to bind labels to the detection reagent in the presence of diethylenetriaminepentaacetic acid (DTPA) or ethylene diaminetetracetic acid (EDTA).

Other methods are also known in the art for the attachment or conjugation of a reagent to its conjugate moiety. Some attachment methods involve the use of an organic chelating agent such as diethylenetriaminepentaacetic acid anhydride (DTPA); ethylenetriaminetetraacetic acid; N-chloro-p-toluenesulfonamide; and/or tetrachloro-3α-6α-diphenylglycouril-3 attached to the ligand (U.S. Pat. Nos. 4,472,509 and 4,938,948, each incorporated herein by reference). Compounds also may be reacted with an enzyme in the presence of a coupling agent such as glutaraldehyde or periodate. Conjugates with fluorescein markers can be prepared in the presence of these coupling agents or by reaction with an isothiocyanate. In U.S. Pat. No. 4,938,948, imaging of breast tumors is achieved using monoclonal antibodies and the detectable imaging moieties are bound to the antibody using linkers such as methyl-p-hydroxybenzimidate or N-succinimidyl-3-(4-hydroxyphenyl)propionate.

IV. Automated Screening with Flow Cytometry

In one embodiment of the invention, fluorescence activated cell sorting (FACS) screening or other automated flow cytometric techniques may be used for the efficient isolation of a bacterial cell comprising a heterologous polypeptide anchored to the outer face of the cytoplasmic membrane of the bacteria. Instruments for carrying out flow cytometry are known to those of skill in the art and are commercially available to the public. Examples of such instruments include FACS Star Plus, FACScan and FACSort instruments from Becton Dickinson (Foster City, Calif.) Epics C from Coulter Epics Division (Hialeah, Fla.) and MoFlo from Cytomation (Colorado Springs, Colo.).

Flow cytometric techniques in general involve the separation of cells or other particles in a liquid sample. Typically, the purpose of flow cytometry is to analyze the separated particles for one or more characteristics thereof, for example, presence of a labeled ligand or other molecule. The basis steps of flow cytometry involve the direction of a fluid sample through an apparatus such that a liquid stream passes through a sensing region. The particles should pass one at a time by the sensor and are categorized base on size, refraction, light scattering, opacity, roughness, shape, fluorescence, etc.

Rapid quantitative analysis of cells proves useful in biomedical research and medicine. Apparati permit quantitative multiparameter analysis of cellular properties at rates of several thousand cells per second. These instruments provide the ability to differentiate among cell types. Data are often displayed in one-dimensional (histogram) or two-dimensional (contour plot, scatter plot) frequency distributions of measured variables. The partitioning of multiparameter data files involves consecutive use of the interactive one- or two-dimensional graphics programs.

Quantitative analysis of multiparameter flow cytometric data for rapid cell detection consists of two stages: cell class characterization and sample processing. In general, the process of cell class characterization partitions the cell feature into cells of interest and not of interest. Then, in sample processing, each cell is classified in one of the two categories according to the region in which it falls. Analysis of the class of cells is very important, as high detection performance may be expected only if an appropriate characteristic of the cells is obtained.

Not only is cell analysis performed by flow cytometry, but so too is sorting of cells. In U.S. Pat. No. 3,826,364, an apparatus is disclosed which physically separates particles, such as functionally different cell types. In this machine, a laser provides illumination which is focused on the stream of particles by a suitable lens or lens system so that there is highly localized scatter from the particles therein. In addition, high intensity source illumination is directed onto the stream of particles for the excitation of fluorescent particles in the stream. Certain particles in the stream may be selectively charged and then separated by deflecting them into designated receptacles. A classic form of this separation is via fluorescent-tagged antibodies, which are used to mark one or more cell types for separation.

Other examples of methods for flow cytometry that could include, but are not limited to, those described in U.S. Pat. Nos. 4,284,412; 4,989,977; 4,498,766; 5,478,722; 4,857,451; 4,774,189; 4,767,206; 4,714,682; 5,160,974; and 4,661,913, each of the disclosures of which are specifically incorporated herein by reference.

For the present invention, an important aspect of flow cytometry is that multiple rounds of screening can be carried out sequentially. Cells may be isolated from an initial round of sorting and immediately reintroduced into the flow cytometer and screened again to improve the stringency of the screen. Another advantage known to those of skill in the art is that nonviable cells can be recovered using flow cytometry. Since flow cytometry is essentially a particle sorting technology, the ability of a cell to grow or propagate is not necessary. Techniques for the recovery of nucleic acids from such nonviable cells are well known in the art and may include, for example, use of template-dependent amplification techniques including PCR.

V. Nucleic Acid-Based Expression Systems

Nucleic acid-based expression systems may find use, in certain embodiments of the invention, for the expression of recombinant proteins. For example, one embodiment of the invention involves transformation of Gram negative bacteria with the coding sequences of fusion polypeptides comprising a detectable heterologous polypeptide fused to a plurality of candidate inner membrane anchor polypeptides.

Certain aspects of the invention may therefore comprise delivery of nucleic acids to target cells. For example, bacterial host cells may be transformed with nucleic acids encoding candidate anchor sequences targeted to the inner membrane of the bacteria. Suitable methods for nucleic acid delivery for transformation of a cell are believed to include virtually any method by which a nucleic acid (e.g., DNA) can be introduced into such a cell. Such methods include, but are not limited to, direct delivery of DNA such as by injection (U.S. Pat. Nos. 5,994,624, 5,981,274, 5,945,100, 5,780,448, 5,736, 524, 5,702,932, 5,656,610, 5,589,466 and 5,580,859, each incorporated herein by reference), including microinjection (Harlan and Weintraub, 1985; U.S. Pat. No. 5,789,215, incorporated herein by reference); by electroporation (U.S. Pat. No. 5,384,253, incorporated herein by reference); by calcium phosphate precipitation (Graham and Van Der Eb, 1973; Chen and Okayama, 1987; Rippe et al., 1990); by using DEAE-dextran followed by polyethylene glycol (Gopal, 1985); by direct sonic loading (Fechheimer et al., 1987); by liposome mediated transfection (Nicolau and Sene, 1982; Fraley et al., 1979; Nicolau et al., 1987; Wong et al., 1980; Kaneda et al., 1989; Kato et al., 1991); by microprojectile bombardment (PCT Application Nos. WO 94/09699 and 95/06128; U.S. Pat. Nos. 5,610,042; 5,322,783 5,563,055, 5,550,318, 5,538,877 and 5,538,880, and each incorporated herein by reference); by agitation with silicon carbide fibers (Kaeppler et al., 1990; U.S. Pat. Nos. 5,302,523 and 5,464, 765, each incorporated herein by reference); by *Agrobacterium*-mediated transformation (U.S. Pat. Nos. 5,591,616 and 5,563,055, each incorporated herein by reference); or by PEG-mediated transformation of protoplasts (Omirulleh et al., 1993; U.S. Pat. Nos. 4,684,611 and 4,952,500, each incorporated herein by reference); by desiccation/inhibition-mediated DNA uptake (Potrykus et al., 1985). Through the application of techniques such as these, organelle(s), cell(s), tissue(s) or organism(s) may be stably or transiently transformed.

In certain embodiments of the present invention, a nucleic acid is introduced into a cell via electroporation. Electroporation involves the exposure of a suspension of cells and DNA to a high-voltage electric discharge. In some variants of this method, certain cell wall-degrading enzymes, such as pectin-degrading enzymes, are employed to render the target recipient cells more susceptible to transformation by electroporation than untreated cells (U.S. Pat. No. 5,384,253, incorporated herein by reference). Alternatively, recipient cells can be made more susceptible to transformation by mechanical wounding.

In other embodiments of the present invention, a nucleic acid is introduced to the cells using calcium phosphate precipitation. Human KB cells have been transfected with adenovirus 5 DNA (Graham and Van Der Eb, 1973) using this technique. Also in this manner, mouse L(A9), mouse C127, CHO, CV-1, BHK, NIH3T3 and HeLa cells were transfected with a neomycin marker gene (Chen and Okayama, 1987), and rat hepatocytes were transfected with a variety of marker genes (Rippe et al., 1990).

A. Vectors

Vectors may find use with the current invention, for example, in the transformation of a Gram negative bacterium with a nucleic acid sequence encoding a candidate anchor polypeptide which one wishes to screen for ability to anchor a given polypeptide to the inner membrane. In one embodiment of the invention, an entire heterogeneous "library" of nucleic acid sequences encoding candidate anchor sequences may be introduced into a population of bacteria, thereby allowing screening of the entire library. The term "vector" is used to refer to a carrier nucleic acid molecule into which a nucleic acid sequence can be inserted for introduction into a cell where it can be replicated. A nucleic acid or polypeptide sequence can be "exogenous," or "heterologous", which means that it is foreign to the cell into which the vector is being introduced or that the sequence is homologous to a sequence in the cell but in a position within the host cell nucleic acid in which the sequence is ordinarily not found. A heterologous polypeptide may therefore be isolated from the same cell in which it is expressed, but positioned at a different location. Vectors include plasmids, cosmids, viruses (bacteriophage, animal viruses, and plant viruses), and artificial chromosomes (e.g., YACs). One of skill in the art may construct a vector through standard recombinant techniques, which are described in Maniatis et al., 1988 and Ausubel et al., 1994, both of which references are incorporated herein by reference.

The term "expression vector" refers to a vector containing a nucleic acid sequence coding for at least part of a gene product capable of being transcribed. In some cases, RNA molecules are then translated into a protein, polypeptide, or peptide. In other cases, these sequences are not translated, for example, in the production of antisense molecules or ribozymes. Expression vectors can contain a variety of "control sequences," which refer to nucleic acid sequences necessary for the transcription and possibly translation of an operably linked coding sequence in a particular host organism. In addition to control sequences that govern transcription and translation, vectors and expression vectors may contain nucleic acid sequences that serve other functions as well and are described infra.

1. Promoters and Enhancers

A "promoter" is a control sequence that is a region of a nucleic acid sequence at which initiation and rate of transcription are controlled. It may contain genetic elements at which regulatory proteins and molecules may bind such as RNA polymerase and other transcription factors. The phrases "operatively positioned," "operatively linked," "under control," and "under transcriptional control" mean that a promoter is in a correct functional location and/or orientation in relation to a nucleic acid sequence to control transcriptional initiation and/or expression of that sequence. A promoter may or may not be used in conjunction with an "enhancer," which refers to a cis-acting regulatory sequence involved in the transcriptional activation of a nucleic acid sequence.

A promoter may be one naturally associated with a gene or sequence, as may be obtained by isolating the 5' non-coding sequences located upstream of the coding segment and/or exon. Such a promoter can be referred to as "endogenous." Similarly, an enhancer may be one naturally associated with a nucleic acid sequence, located either downstream or upstream of that sequence. Alternatively, certain advantages will be gained by positioning the coding nucleic acid segment under the control of a recombinant or heterologous promoter, which refers to a promoter that is not normally associated with a nucleic acid sequence in its natural environment. A recombinant or heterologous enhancer refers also to an enhancer not normally associated with a nucleic acid sequence in its natural environment. Such promoters or enhancers may include promoters or enhancers of other genes, and promoters or enhancers isolated from any other prokaryotic, viral, or eukaryotic cell, and promoters or enhancers not "naturally occurring," i.e., containing different elements of different transcriptional regulatory regions, and/or mutations that alter expression.

In addition to producing nucleic acid sequences of promoters and enhancers synthetically, sequences may be produced using recombinant cloning and/or nucleic acid amplification technology, including PCR, in connection with the compositions disclosed herein (see U.S. Pat. No. 4,683,202, U.S. Pat. No. 5,928,906, each incorporated herein by reference). Furthermore, it is contemplated that the control sequences that direct transcription and/or expression of sequences within non-nuclear organelles such as mitochondria, chloroplasts, and the like, can be employed as well.

Naturally, it will be important to employ a promoter and/or enhancer that effectively directs the expression of the DNA segment in the cell type, organelle, and organism chosen for expression. One example of such promoter that may be used with the invention is the *E. coli* arabinose promoter. Those of skill in the art of molecular biology generally are familiar with the use of promoters, enhancers, and cell type combinations for protein expression, for example, see Sambrook et al. (1989), incorporated herein by reference. The promoters employed may be constitutive, tissue-specific, inducible, and/or useful under the appropriate conditions to direct high level expression of the introduced DNA segment, such as is advantageous in the large-scale production of recombinant proteins and/or peptides. The promoter may be heterologous or endogenous.

2. Initiation Signals and Internal Ribosome Binding Sites

A specific initiation signal also may be required for efficient translation of coding sequences. These signals include the ATG initiation codon or adjacent sequences. Exogenous translational control signals, including the ATG initiation codon, may need to be provided. One of ordinary skill in the art would readily be capable of determining this and providing the necessary signals. It is well known that the initiation codon must be "in-frame" with the reading frame of the desired coding sequence to ensure translation of the entire insert. The exogenous translational control signals and initiation codons can be either natural or synthetic. The efficiency of expression may be enhanced by the inclusion of appropriate transcription enhancer elements.

3. Multiple Cloning Sites

Vectors can include a multiple cloning site (MCS), which is a nucleic acid region that contains multiple restriction enzyme sites, any of which can be used in conjunction with standard recombinant technology to digest the vector (see Carbonelli et al., 1999, Levenson et al., 1998, and Cocea, 1997, incorporated herein by reference). "Restriction enzyme digestion" refers to catalytic cleavage of a nucleic acid molecule with an enzyme that functions only at specific locations in a nucleic acid molecule. Many of these restriction enzymes are commercially available. Use of such enzymes is understood by those of skill in the art. Frequently, a vector is linearized or fragmented using a restriction enzyme that cuts within the MCS to enable exogenous sequences to be ligated to the vector. "Ligation" refers to the process of forming phosphodiester bonds between two nucleic acid fragments, which may or may not be contiguous with each other. Techniques involving restriction enzymes and ligation reactions are well known to those of skill in the art of recombinant technology.

4. Termination Signals

The vectors or constructs prepared in accordance with the present invention will generally comprise at least one termination signal. A "termination signal" or "terminator" is comprised of the DNA sequences involved in specific termination of an RNA transcript by an RNA polymerase. Thus, in certain embodiments, a termination signal that ends the production of an RNA transcript is contemplated. A terminator may be necessary in vivo to achieve desirable message levels.

Terminators contemplated for use in the invention include any known terminator of transcription described herein or known to one of ordinary skill in the art, including but not limited to, for example, rhp dependent or rho independent terminators. In certain embodiments, the termination signal may be a lack of transcribable or translatable sequence, such as due to a sequence truncation.

5. Origins of Replication

In order to propagate a vector in a host cell, it may contain one or more origins of replication sites (often termed "ori"), which is a specific nucleic acid sequence at which replication is initiated. Alternatively an autonomously replicating sequence (ARS) can be employed if the host cell is yeast.

6. Selectable and Screenable Markers

In certain embodiments of the invention, cells containing a nucleic acid construct of the present invention may be identified in vitro or in vivo by including a marker in the expression vector. Such markers would confer an identifiable change to the cell permitting easy identification of cells containing the expression vector. Generally, a selectable marker is one that confers a property that allows for selection. A positive selectable marker is one in which the presence of the marker allows for its selection, while a negative selectable marker is one in which its presence prevents its selection. An example of a positive selectable marker is a drug resistance marker.

Usually the inclusion of a drug selection marker aids in the cloning and identification of transformants, for example, genes that confer resistance to neomycin, puromycin, hygromycin, DHFR, GPT, zeocin and histidinol are useful selectable markers. In addition to markers conferring a phenotype that allows for the discrimination of transformants based on the implementation of conditions, other types of markers including screenable markers such as GFP, whose basis is calorimetric analysis, are also contemplated. Alternatively, screenable enzymes such as herpes simplex virus thymidine kinase (tk) or chloramphenicol acetyltransferase (CAT) may be utilized. One of skill in the art would also know how to employ immunologic markers, possibly in conjunction with FACS analysis. The marker used is not believed to be important, so long as it is capable of being expressed simultaneously with the nucleic acid encoding a gene product. Further examples of selectable and screenable markers are well known to one of skill in the art.

B. Host Cells

As used herein, the terms "cell," "cell line," and "cell culture" may be used interchangeably. All of these terms also include their progeny, which is any and all subsequent generations. It is understood that all progeny may not be identical due to deliberate or inadvertent mutations. In the context of expressing a heterologous nucleic acid sequence, "host cell" refers to a prokaryotic cell, and it includes any transformable organism that is capable of replicating a vector and/or expressing a heterologous gene encoded by a vector. A host cell can, and has been, used as a recipient for vectors. A host cell may be "transfected" or "transformed," which refers to a process by which exogenous nucleic acid is transferred or introduced into the host cell. A transformed cell includes the primary subject cell and its progeny.

In particular embodiments of the invention, a host cell is a Gram negative bacterial cell. These bacteria are suited for use with the invention in that they posses a periplasmic space between the inner and outer membrane and, particularly, the aforementioned inner membrane between the periplasm and cytoplasm, which is also known as the cytoplasmic membrane. As such, any other cell with such a periplasmic space could be used in accordance with the invention. Examples of Gram negative bacteria that may find use with the invention may include, but are not limited to, *E. coli, Pseudomonas aeruginosa, Vibrio cholera, Salmonella typhimurium, Shigella flexneri, Haemophilus influenza, Bordotella pertussi, Erwinia amylovora, Rhizobium* sp. The Gram negative bacterial cell may be still further defined as bacterial cell which has been transformed with the coding sequence of a fusion polypeptide comprising a candidate binding polypeptide capable of binding a selected ligand. The polypeptide is anchored to the outer face of the cytoplasmic membrane, facing the periplasmic space, and may comprise an antibody coding sequence or another sequence. One means for expression of the polypeptide is by attaching a leader sequence to the polypeptide capable of causing such directing.

Numerous prokaryotic cell lines and cultures are available for use as a host cell, and they can be obtained through the American Type Culture Collection (ATCC), which is an organization that serves as an archive for living cultures and genetic materials (www.atcc.org). An appropriate host can be determined by one of skill in the art based on the vector backbone and the desired result. A plasmid or cosmid, for example, can be introduced into a prokaryote host cell for replication of many vectors. Bacterial cells used as host cells for vector replication and/or expression include DH5α, JM109, and KC8, as well as a number of commercially available bacterial hosts such as SURE® Competent Cells and SOLOPACK™ Gold Cells (STRATAGENE®, La Jolla). Alternatively, bacterial cells such as *E. coli* LE392 could be used as host cells for bacteriophage.

Many host cells from various cell types and organisms are available and would be known to one of skill in the art. Similarly, a viral vector may be used in conjunction with a prokaryotic host cell, particularly one that is permissive for replication or expression of the vector. Some vectors may employ control sequences that allow it to be replicated and/or expressed in both prokaryotic and eukaryotic cells. One of skill in the art would further understand the conditions under which to incubate all of the above described host cells to maintain them and to permit replication of a vector. Also understood and known are techniques and conditions that would allow large-scale production of vectors, as well as production of the nucleic acids encoded by vectors and their cognate polypeptides, proteins, or peptides.

C. Expression Systems

Numerous expression systems exist that comprise at least a part or all of the compositions discussed above. Such systems could be used, for example, for the production of a polypeptide product identified in accordance with the invention as capable of anchoring a particular polypeptide on the inner membrane. Prokaryote-based systems can be employed for use with the present invention to produce nucleic acid sequences, or their cognate polypeptides, proteins and peptides. Many such systems are commercially and widely available. Other examples of expression systems comprise of vectors containing a strong prokaryotic promoter such as T7, Tac, Trc, BAD, lambda pL, Tetracycline or Lac promoters, the pET Expression System and an *E. Coli* expression system.

VI. Manipulation and Detection of Nucleic Acids

In certain embodiments of the invention, it may be desired to employ one or more techniques for the manipulation, isolation and/or detection of nucleic acids. Such techniques may include, for example, the preparation of vectors for transformation of host cells as well as methods for cloning selected nucleic acid segments from a transgenic cell. Methodology for carrying out such manipulations will be well known to those of skill in the art in light of the instant disclosure.

Nucleic acids used as a template for amplification may be isolated from cells, tissues or other samples according to standard methodologies (Sambrook et al., 1989). In certain embodiments, analysis may be performed on whole cell or tissue homogenates or biological fluid samples without substantial purification of the template nucleic acid. The nucleic acid may be genomic DNA or fractionated or whole cell RNA. Where RNA is used, it may be desired to first convert the RNA to a complementary DNA.

The term "primer," as used herein, is meant to encompass any nucleic acid that is capable of priming the synthesis of a nascent nucleic acid in a template-dependent process. Typically, primers are oligonucleotides from ten to twenty and/or thirty base pairs in length, but longer sequences can be employed. Primers may be provided in double-stranded and/or single-stranded form, although the single-stranded form is preferred.

Pairs of primers designed to selectively hybridize to nucleic acids corresponding to a selected nucleic acid sequence are contacted with the template nucleic acid under conditions that permit selective hybridization. Depending upon the desired application, high stringency hybridization conditions may be selected that will only allow hybridization to sequences that are completely complementary to the primers. In other embodiments, hybridization may occur under reduced stringency to allow for amplification of nucleic acids contain one or more mismatches with the primer sequences. Once hybridized, the template-primer complex is contacted with one or more enzymes that facilitate template-dependent nucleic acid synthesis. Multiple rounds of amplification, also referred to as "cycles," are conducted until a sufficient amount of amplification product is produced.

The amplification product may be detected or quantified. In certain applications, the detection may be performed by visual means. Alternatively, the detection may involve indirect identification of the product via chemiluminescence, radioactive scintigraphy of incorporated radiolabel or fluorescent label or even via a system using electrical and/or thermal impulse signals (Affymax technology; Bellus, 1994).

A number of template dependent processes are available to amplify the oligonucleotide sequences present in a given template sample. One of the best known amplification methods is the polymerase chain reaction (referred to as PCR) which is described in detail in U.S. Pat. Nos. 4,683,195, 4,683,202 and 4,800,159, and in Innis et al., 1988, each of which is incorporated herein by reference in their entirety.

A reverse transcriptase PCR amplification procedure may be performed to quantify the amount of mRNA amplified. Methods of reverse transcribing RNA into cDNA are well known (see Sambrook et al., 1989). Alternative methods for reverse transcription utilize thermostable DNA polymerases. These methods are described in WO 90/07641. Polymerase chain reaction methodologies are well known in the art. Representative methods of RT-PCR are described in U.S. Pat. No. 5,882,864.

Another method for amplification is ligase chain reaction ("LCR"), disclosed in European Application 320 308, incorporated herein by reference in its entirety. U.S. Pat. No. 4,883,750 describes a method similar to LCR for binding probe pairs to a target sequence. A method based on PCR and oligonucleotide ligase assay (OLA), disclosed in U.S. Pat. No. 5,912,148, may also be used.

Alternative methods for amplification of target nucleic acid sequences that may be used in the practice of the present invention are disclosed in U.S. Pat. Nos. 5,843,650, 5,846,709, 5,846,783, 5,849,546, 5,849,497, 5,849,547, 5,858,652, 5,866,366, 5,916,776, 5,922,574, 5,928,905, 5,928,906, 5,932,451, 5,935,825, 5,939,291 and 5,942,391, GB Application No. 2 202 328, and in PCT Application No. PCT/US89/01025, each of which is incorporated herein by reference in its entirety.

Qbeta Replicase, described in PCT Application No. PCT/US87/00880, may also be used as an amplification method in the present invention. In this method, a replicative sequence of RNA that has a region complementary to that of a target is added to a sample in the presence of an RNA polymerase. The polymerase will copy the replicative sequence which may then be detected.

An isothermal amplification method, in which restriction endonucleases and ligases are used to achieve the amplification of target molecules that contain nucleotide 5'-[alpha-thio]-triphosphates in one strand of a restriction site may also be useful in the amplification of nucleic acids in the present invention (Walker et al., 1992). Strand Displacement Amplification (SDA), disclosed in U.S. Pat. No. 5,916,779, is another method of carrying out isothermal amplification of nucleic acids which involves multiple rounds of strand displacement and synthesis, i.e., nick translation.

Other nucleic acid amplification procedures include transcription-based amplification systems (TAS), including nucleic acid sequence based amplification (NASBA) and 3SR (Kwoh et al., 1989; Gingeras et al., PCT Application WO 88/10315, incorporated herein by reference in their entirety). European Application No. 329 822 disclose a nucleic acid amplification process involving cyclically synthesizing single-stranded RNA ("ssRNA"), ssDNA, and double-stranded DNA (dsDNA), which may be used in accordance with the present invention.

PCT Application WO 89/06700 (incorporated herein by reference in its entirety) discloses a nucleic acid sequence amplification scheme based on the hybridization of a promoter region/primer sequence to a target single-stranded DNA ("ssDNA") followed by transcription of many RNA copies of the sequence. This scheme is not cyclic, i.e., new templates are not produced from the resultant RNA transcripts. Other amplification methods include "race" and "one-sided PCR" (Frohman, 1990; Ohara et al., 1989).

VII. EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Demonstration of Anchored Periplasmic Expression to Target Small Molecules and Peptides The ability of scFvs displayed by APEx to target small molecules and peptides is shown in FIGS. 1A-1B and in FIG. 1C, respectively. Three cultures of *Escherichia coli* containing fusions of the first six amino acids of NlpA (to serve as a inner membrane targeting sequence for APEx analysis) to either an anti-methamphetamine, anti-digoxin, or anti-peptide scfv were grown up and induced for protein expression as described below. Cells of each construct were then labeled in 5×PBS buffer with 200 nM concentrations of methamphetamine-FL (FIG. 1A), digoxigenin-bodipy (FIG. 1B), or 200 nM peptide(18mer)-BodipyFL (FIG. 1C). The data presented shows a histogram representation of 10,000 events from each of the labeled cell cultures. The results demonstrate the ability of scfvs displayed by APEx to bind to their specific antigen conjugated fluorophore, with minimal crossreactivity to non-specific ligands.

Example 2

Demonstration of Recognition of Ab Fragments by Anchored Periplasmic Expression To demonstrate that the scFv is accessible to larger proteins, it was first demonstrated that polyclonal antibody serum against human Ab fragments or mouse Ab fragments would recognize scFvs derived from each displayed on the *E. coli* inner membrane by anchored periplasmic expression. *Escherichia coli* expressing a mouse derived scFv via anchored periplasmic expression (FIG. 2A) or expressing a human derived scFv via anchored periplasmic expression (FIG. 2B) were labeled as described below with either anti-mouse polyclonal IgG (H+ L)-Alexa-FL or anti-human polyclonal IgG (Fab)-FITC. Results (FIG. 2A, 2B) in the form of histogram representations of 10000 events of each demonstrated that the anti-human polyclonal (approximately 150 kDa in size) recognized the human derived scFv specifically while the anti-mouse polyclonal (150 kDa) recognized the mouse derived scFv.

Example 3

Figure 3B:
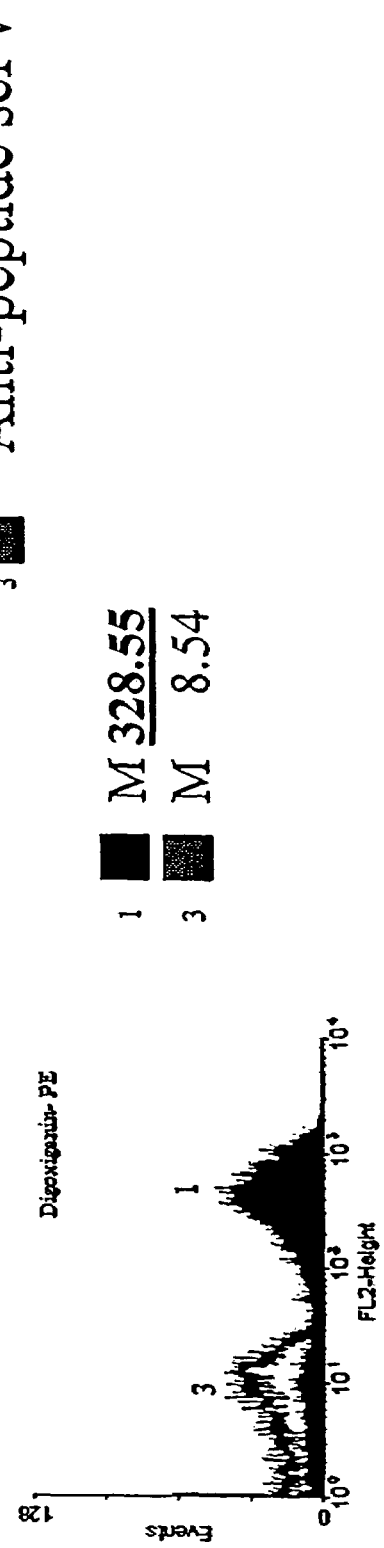

Demonstration of the Ability of scFvs Displayed by Anchored Periplasmic Expression to Specifically Bind Large Antigen Conjugated Fluorophores To demonstrate the ability of scFvs displayed via anchored periplasmic expression to specifically bind to large antigen conjugated fluorophores, *E. coli* were induced and labeled as described below expressing, via anchored periplasmic expression, an anti-protective antigen(PA) scFv (PA is one component of the anthrax toxin: a 83 kDa protein) or an anti-digoxigenin scFv. Histogram data of 10,000 events demonstrated specific binding to a PA-Cy5 antigen conjugated fluorophore as compared to the cells expressing the an anti-digoxigenin scFv (FIG. 3A). To further illustrate this point, digoxigenin was coupled to phycoerythrin(PE), a 240 kDa fluorescent protein. Cells were labeled with this conjugate as described below. It was found that *E. coli* (10,000 events) expressing the anti-digoxigenin scFv via anchored periplasmic expression were labeled with the large PE-digoxigenin conjugate while those expressing a non-specific scFv via anchored periplasmic expression show little fluorescence (FIG. 3B).

Example 4

Figure 4:
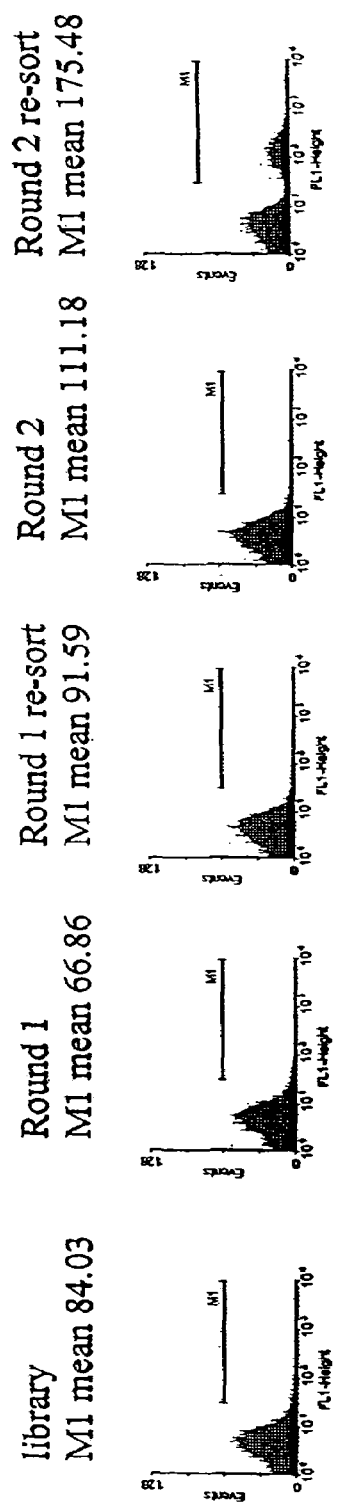
FIG. 4: Maturation of methamphetamine binding scFv for Meth-FL probe.

Demonstration of Selecting for Improved scFv Variants from a Library of scFvs by Flow Cytometric Selection Scans were carried out of polyclonal *Escherichia coli* expressing, via anchored periplasmic expression, a mutagenic library of an scFv with affinity to methamphetamine. Through two rounds of sorting and re-sorting using a Methamphetamine conjugated fluorophore, a sub-population of the library was isolated. (FIG. 4)

Figure 5:
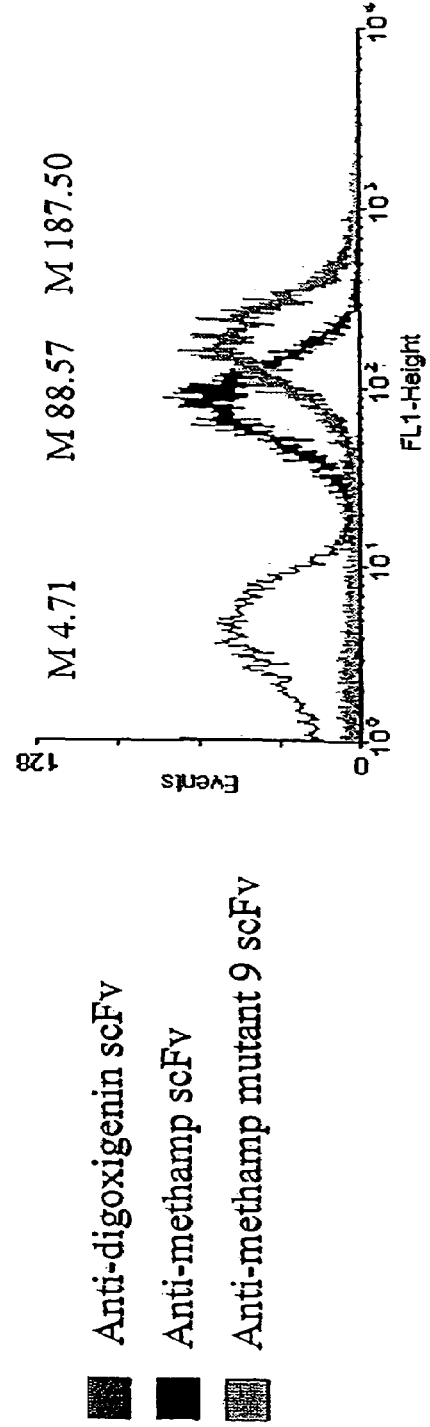
FIG. 5: Analysis of clone designated mutant 9 with higher mean FL signal than the parent anti-methamphetamine scFv. The scFvs expressed via anchored periplasmic expression are as indicated.
Figure 6:
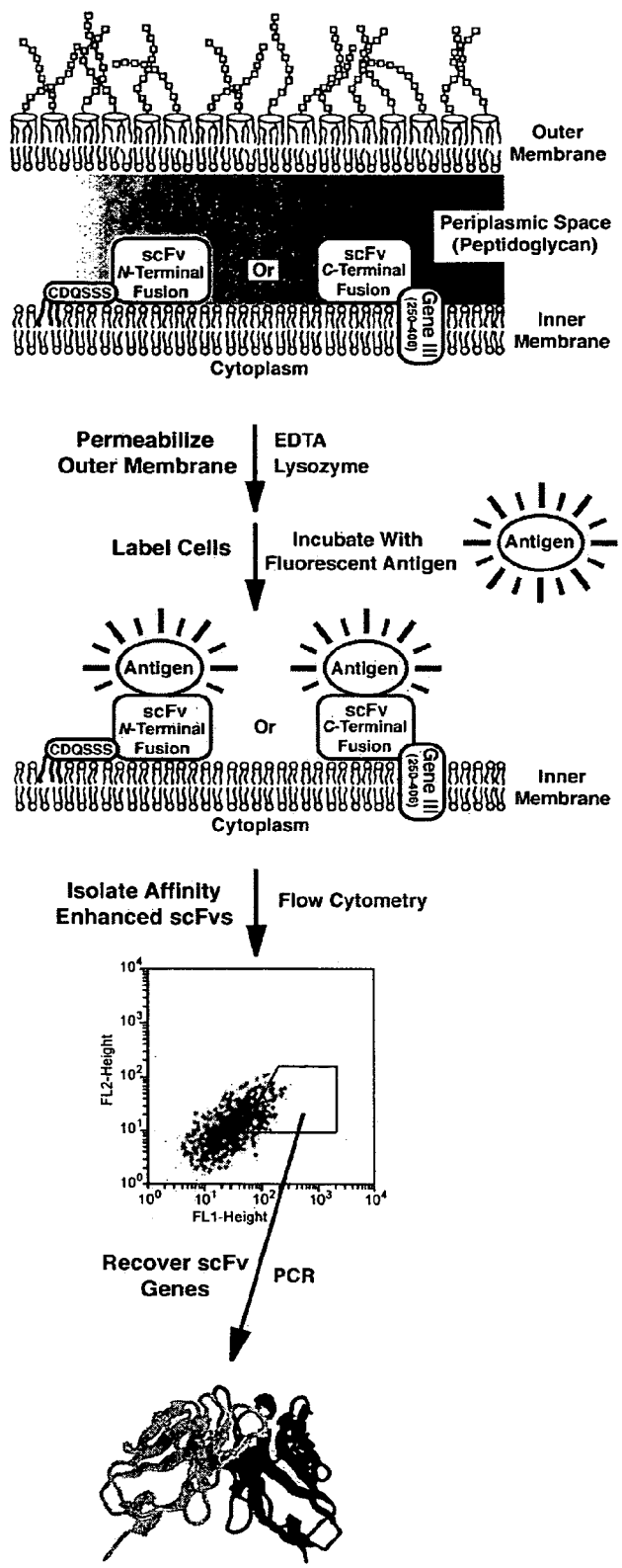
FIG. 6: A schematic diagram showing the principle of Anchored Periplasmic Expression (APEx) for the flow cytometry based isolation of high affinity antibody fragments.

Individual clones from this library were labeled with the same Methamphetamine flourophore and analyzed as described below. Shown in FIG. 5 is an example of a clone, designated mutant 9, that had a higher mean FL signal than the parent anti-methamphetamine scFv.

Example 5

Materials and Methods

A. Vector Construction

The leader peptide and first six amino acids of the mature NlpA protein were generated by whole cell PCR (Perken Elmer) on XL1-blue *Escherichia coli*, (Stratagene) using primers BRH#08 5' GAAGGAGATATACATATGAAACT-GACAACACATCATCTA 3' (SEQ IDNO:6) and BRH#9 5' CTGGGCCATGGCCGGCTGGGCCTCGCT-GCTACTCTGGTCGAACC 3', (SEQ ID NO:7) VENT Polymerase™(New England Biolabs) and dNTPs (Roche). This was then cut with NdeI and SfiI restriction endonucleases and cloned between a lac promoter and a multiple cloning site (MCS) in a *E. coil* expression vector with the following elements down stream of the MCS: myc and his tag, Cm resistance marker, colE1 origin and lac I. ScFvs of interest were then cloned into the MCS and the vector was transformed into ABLE™C *E. coil*(Stratagene).

B. Expression

*E. coli* cells are inoculated in TB media+2% glucose and 30 mg/l chloramphenicol to an OD600 of 0.1. Cells are grown for 2 hours at 37C and then cooled to 25C for 30 minutes. They are then induced at 25C with 1 mM IPTG for 4 hrs.

Mutagenic libraries of scFv sequences were constructed using mutagenic PCR methods as described by Fromant M, et al. (1995) utilizing the original scFv sequence as a template. These mutagenic products were then cloned into the above mentioned APEx expression vector, transformed into ABLE™C E. coil and plated on agar plates with SOC media containing 2% glucose and 30 μg/ml chloramphenicol. Following overnight incubation at 30C., the E. coil were scraped from the plates, frozen in 15% glycerol aliquots and stored at −80C. for future flow cytometric sorting.

C. Labeling Strategies

Following induction, cells are either incubated in 5×PBS with 200 nM probe for 45 minutes or are resuspended in 350 μl of 0.75M sucrose, 100 mM Tris. 35 μl of lysozyme at 10 mg/ml is then added followed by 700 μl of 1 mM EDTA added dropwise with gentle shaking. This is allowed to sit on ice for 10 min followed by the addition of 50 μl of 0.5M $MgCl_2$. After an additional 10 minutes on ice the suspension is centrifuged at 13,200 g for 1 minute, decanted and resuspended in 500% 1×PBS. The cells are then labeled with 200 nM of probe for 45 minutes, and are then analyzed by flow cytometry and selected for improved fluorescence.

D. Strains and Plasmids

Strain ABLE™C (Stratagene) was used for screening with APEx. E. Coli strains TG1 and HB2151 were provided with the Griffin library. ABLE™C and ABLE™K were purchased from Stratagene and helper phage M13K07 from Pharmacia. A positive control for FACS analysis of a phage display vehicle was constructed by replacing a pre-existing scFv in pHEN2 with the 26.10 scFv to create pHEN2.dig. The negative control was pHEN2.thy bearing the anti-thyroglobulin scFv provided with the Griffin.1 library. The $P_{tac}$ vector was a derivative of pIMS120 (Hayhurst, 2000).

E. Phage Panning

The Griffin. 1 library is a semi-synthetic scFv library derived from a large repertoire of human heavy and light chains with part or all of the CDR3 loops randomly mutated and recombined in vivo (Griffiths et al., 1994). The library represents one potential source of candidate binding polypeptides for screening by anchored periplasmic expression in accordance with the invention. The library was rescued and subjected to five rounds of panning according to the web-site instruction manual, available on the world wide web at mrc-cpe.cam.ac.uk/~phage/glp, summarized in Example 9, below. Immunotubes were coated with 10 μgml⁻digoxin-BSA conjugate and the neutralized eluates were halved and used to infect either TG-1 for the next round of phage panning, or ABLE™C for FACS analysis.

Eluate titers were monitored to indicate enrichment of antigen binding phage. To confirm reactivity, a polyclonal phage ELISA of purified, titer normalized phage stocks arising from each round was performed on digoxin-ovalbumin conjugate. The percentage of positive clones arising in rounds 3, 4 and 5 was established by monoclonal phage ELISA of 96 isolates after each round. A positive was arbitrarily defined as an absorbance greater than 0.5 with a background signal rarely above 0.01. MvaI fingerprinting was applied to 24 positive clones from rounds 3, 4 and 5.

F. FACS Screening

For scanning with APEx expression, glycerol stocks of E. coli carrying the APEx construct were grown and labeled as described in section B and C. Following labeling cells were washed once in PBS and scanned. In the aforementioned studies using bodipy or FL labeled antigen, a 488 nm laser for excitation was used, while with Cy5 a 633 nm laser was used. Scanning was accomplished on a FACSCalibur (BD) using the following instrument settings: Sidescatter trigger V 400, Threshold 250, Forward scatter E01, FL1 V 400 FL2 V 400 (488 nm ex), FL4 V 700 (633 nm ex).

Sorting with APEx expression was as follows: all sorts were performed using a MoFlo FC (Cytomation). Previously described libraries were grown and labeled as described in section B and C, washed once with PBS and sorted for increased FL intensity. Subsequent rounds of sorting were applied until polyclonal scans of the population demonstrate enrichment. (See FIG. 4) Individual clones were then picked and analyzed for FL activity.

For other studies, an aliquot of phagemid containing, ABLE™C glycerol stock was scraped into 1 ml of 2×TY (2% glucose, 100 μgml⁻¹ ampicillin) to give an OD at 600 nm of approximately 0.1 cm⁻¹. After shaking vigorously at 37° C. for 2 h, IPTG was added to 1 mM and the culture shaken at 25° C. for 4 h. 50 μl of culture was labeled with 100 nM BODIPY™-digoxigenin (Daugherty et al., 1999) in 1 ml of 5×PBS for 1 h at room temperature with moderate agitation. For the last 10 min of labeling, propidium iodide was added to 2 μg/ml⁻¹. Cells were pelleted and resuspended in 100 μl of labeling mix. Scanning was performed with Becton-Dickinson FACSort, collecting $10^4$ events at 1500 s⁻¹.

For FACS library sorting, the cells were grown in Difcou Terrific Broth and induced with 0.1 mMIPTG. Sorting was performed on 106 events (107 for round 2) in exclusion mode at 1000⁻¹. Collected sort liquor was passed through 0.7 μm membrane filters and colonies allowed to grow after placing the filter on top of SOC agar plus appropriate antibiotics at 30° C. for 24 h.

G. Analysis of Phage Clones

Screening phage particles by ELISA is summarized as follows. Binding of phage in ELISA is detected by primary sheep anti-M13 antisera (CP laboratories or 5 prime-3 prime) followed by a horseradish peroxidase (HRP) conjugated anti-sheep antibody (Sigma). Alternatively, a HRP-anti-M13 conjugate can be used (Pharmacia). Plates can be blocked with 2% MPBS or 3% BSA-PBS. For the polyclonal phage ELISA, the technique is generally as follows: coat MicroTest III flexible assay plates (Falcon) with 100 μl per well of protein antigen. Antigen is normally coated overnight at 4° C. at a concentration of 10-100 μg/ml in either PBS or 50 mM sodium hydrogen carbonate, pH 9.6. Rinse wells 3 times with PBS, by flipping over the ELISA plates to discard excess liquid, and fill well with 2% MPBS or 3% BSA-PBS for 2 hr at 37° C. Rinse wells 3 times with PBS. Add 10 μl PEG precipitated phage from the stored aliquot of phage from the end of each round of selection (about $10^{10}$ tfu.). Make up to 100 μl with 2% MPBS or 3% BSA-PBS. Incubate for 90 min at rt. Discard the test solution and wash three times with PBS-0.05% Tween 20, then 3 times with PBS. Add appropriate dilution of HRP-anti-M13 or sheep anti-M13 antisera in 2% MPBS or 3% BSA-PBS. Incubate for 90 min at rt, and wash three times with PBS-0.05% Tween 20, then 3 times with PBS. If sheep anti-M13 antisera is used, incubate for 90 min at rt, with a suitable dilution of HRP-anti-sheep antisera in 2% MPBS or 3% BSA and wash three times with PBS-0.05% Tween 20, then 3 times with PBS. Develop with substrate solution (100 μg/ml TMB in 100 mM sodium acetate, pH 6.0, add 10 μl of 30% hydrogen peroxide per 50 ml of this solution directly before use). Add 100 μl to each well and leave at rt for 10 min. A blue color should develop. Stop the reaction by adding 50 μl 1 M sulfuric acid. The color should turn yellow. Read the OD at 450 nm and at 405 nm. Subtract OD 405 from OD 450.

Monoclonal phage ELISA can be summarized as follows. To identify monoclonal phage antibodies the pHEN phage particles need to be rescued: Inoculate individual colonies from the plates in C10 (after each round of selection) into 100 µl 2×TY containing 100 µg/ml ampicillin and 1% glucose in 96-well plates (Corning 'Cell Wells') and grow with shaking (300 rpm.) overnight at 30° C. Use a 96-well transfer device to transfer a small inoculum (about 2 µl) from this plate to a second 96-well plate containing 200 µl of 2×TY containing 100 µg/ml ampicillin and 1% glucose per well. Grow shaking at 37° C. for 1 hr. Make glycerol stocks of the original 96-well plate, by adding glycerol to a final concentration of 15%, and then storing the plates at −70° C. To each well (of the second plate) add VCS-M13 or M13KO7 helper phage to an moi of 10. Stand for 30 min at 37° C. Centrifuge at 1,800 g for 10 min, then aspirate off the supernatant. Resuspend pellet in 200 µl 2×TY containing 100 µg/ml ampicillin and 50 µg/ml kanamycin. Grow shaking overnight at 30° C. Spin at 1,800 g for 10 min and use 100 µl of the supernatant in phage ELISA as detailed above.

Production of antibody fragments is summarized as follows: the selected pHEN needs to be infected into HB2151 and then induced to give soluble expression of antibody fragments for ELISA. From each selection take 10 µl of eluted phage (about $10^5$ t.u.) and infect 200 µl exponentially growing HB2151 bacteria for 30 min at 37° C. (waterbath). Plate 1, 10, 100 µl, and 1:10 dilution on TYE containing 100 µg/ml ampicillin and 1% glucose. Incubate these plates overnight at 37° C. Pick individual colonies into 100 µl 2×TY containing 100 µg/ml ampicillin and 1% glucose in 96-well plates (Corning 'Cell Wells'), and grow with shaking (300 rpm.) overnight at 37° C. A glycerol stock can be made of this plate, once it has been used to inoculate another plate, by adding glycerol to a final concentration of 15% and storing at −70° C. Use a 96-well transfer device to transfer a small inocula (about 2 µl) from this plate to a second 96-well plate containing 200 µl fresh 2×TY containing 100 µg/ml ampicillin and 0.1% glucose per well. Grow at 37° C., shaking until the OD at 600 nm is approximately 0.9 (about 3 hr). Once the required OD is reached add 25 µl 2×TY containing 100 µg/ml ampicillin and 9 mM IPTG (final concentration 1 mM IPTG). Continue shaking at 30° C. for a further 16 to 24 hr. Coat MicroTest III flexible assay plates (Falcon) with 100 µl per well of protein antigen.

Antigen is normally coated overnight at rt at a concentration of 10-100 µg/ml in either PBS or 50 mM sodium hydrogen carbonate, pH 9.6. The next day rinse wells 3 times with PBS, by flipping over the ELISA plates to discard excess liquid, and block with 200 µl per well of 3% BSA-PBS for 2 hr at 37° C. Spin the bacterial plate at 1,800 g for 10 min and add 100 µl of the supernatant (containing the soluble scFv) to the ELISA plate for 1 hr at rt. Discard the test solution and wash three times with PBS. Add 50 µl purified 9E10 antibody (which detects myc-tagged antibody fragments) at a concentration of 4 µg/ml in 1% BSA-PBS and 50 µl of a 1:500 dilution of HRP-anti-mouse antibody in 1% BSA-PBS. Incubate for 60 min at rt, and wash three times with PBS-0.05% Tween 20, then 3 times with PBS. Develop with substrate solution (100 µg/ml TMB in 100 mM sodium acetate, pH 6.0. Add 10 µl of 30% hydrogen peroxide per 50 ml of this solution directly before use). Add 100 µl to each well and leave at rt for 10 min. A blue color should develop. Stop the reaction by adding 50 µl 1 M sulfuric acid. The color should turn yellow. Read the OD at 450 nm and at 405 nm. Subtract OD 405 from OD 450.

Inserts in the library can be screened by PCR screening using the primers designated LMB3: CAG GAA ACA GCT ATG AC (SEQ ID NO:1) and Fd seq1: GAA TTT TCT GTA TGA GG (SEQ ID NO:2). For sequencing of the VH and VL, use is recommend of the primers FOR_LinkSeq: GCC ACC TCC GCC TGA ACC (SEQ ID NO:3) and pHEN-SEQ: CTA TGC GGC CCC ATT CA (SEQ ID NO:4).

Example 6

Use of Anchored Periplasmic Expression to Isolate Antibodies with Over a 120-Fold Improvement in Affinity for the *Bacillus anthracis* Protective Antigen The screening of large libraries requires a physical link between a gene, the protein it encodes, and the desired function. Such a link can be established using a variety of in vivo display technologies that have proven invaluable for mechanistic studies, for biotechnological purposes and for proteomics research (Hoess, 2001; Hayhurst and Georgiou, 2001; Wittrup, 2000).

APEx is an alternative approach that allows screening by flow cytometry (FC). FC combines high throughput with real-time, quantitative, multi-parameter analysis of each library member. With sorting rates on the order of more than 400 million cells per hour, commercial FC machines can be employed to screen libraries of the size accessible within the constraints of microbial transformation efficiencies. Furthermore, multi-parameter FC can provide valuable information regarding the function of each and every clone in the library in real time, thus helping to guide the library construction process and optimize sorting conditions (Boder and Wittrup, 2000; Daugherty et al., 2000).

Bacterial and yeast protein display in combination with FC has been employed for the engineering of high affinity antibodies to a variety of ligands (Daugherty et al., 1999; Boder et al., 2000). However, the requirement for the display of proteins on cell surfaces imposes a number of biological constraints that can impact library screening applications. Processes such as the unfolded protein response in eucaryotes or the stringency of protein sorting to the outer membrane of Gram-negative bacteria limit the diversity of the polypeptides that are actually compatible with surface display (Sagt et al., 2002; Sathopoulos et al., 1996). In addition, microbial surfaces are chemically complex structures whose macromolecular composition can interfere with protein:ligand recognition. This problem is particularly manifest in Gram-negative bacteria because the presence of lipopolysaccharides on the outer membrane presents a steric barrier to protein:ligand recognition, a fact that likely contributed to the evolution of specialized appendages, such as pili or fimbriae (Hultgren et al., 1996).

APEx overcomes the biological constraints and antigen access limitations of previous display strategies, enabling the efficient isolation of antibodies to virtually any size antigen. In APEx, proteins are tethered to the external (periplasmic) side of the *E. coli* cytoplasmic membrane as either N- or C-terminal fusions, thus eliminating biological constraints associated with the display of proteins on the cell surface. Following chemical/enzymatic permeabilization of the bacterial outer membrane, *E. coli* cells expressing anchored scFv antibodies can be specifically labeled with fluorescent antigens, of at least 240 kDa, and analyzed by FC. By using APEx the inventors have demonstrated the efficient isolation of antibodies with markedly improved ligand affinities, including an antibody fragment to the protective antigen of *Bacillus anthracis* with an affinity that was increased over 120-fold.

A. Anchored Periplasmic Expression and Detection of Ligand Binding

For screening applications, an ideal expression system should minimize cell toxicity or growth abnormalities that can arise from the synthesis of heterologous polypeptides (Daugherty et al., 2000). Use of APEx avoids the complications that are associated with transmembrane protein fusions (Miroux and Walker, 1996; Mingarro et al., 1997). Unlike membrane proteins, bacterial lipoproteins are not known to require the SRP or YidC pathways for membrane anchoring (Samuelson et al., 2000). Lipoproteins are secreted across the membrane via the Sec pathway and once in the periplasm, a diacylglyceride group is attached through a thioether bond to a cysteine residue on the C-terminal side of the signal sequence. The signal peptide is then cleaved by signal peptidase II, the protein is fatty acylated at the modified cysteine residue, and finally the lipophilic fatty acid inserts into the membrane, thereby anchoring the protein (Pugsley, 1993; Seydel et al., 1999; Yajushi et al., 2000).

Figure 7:
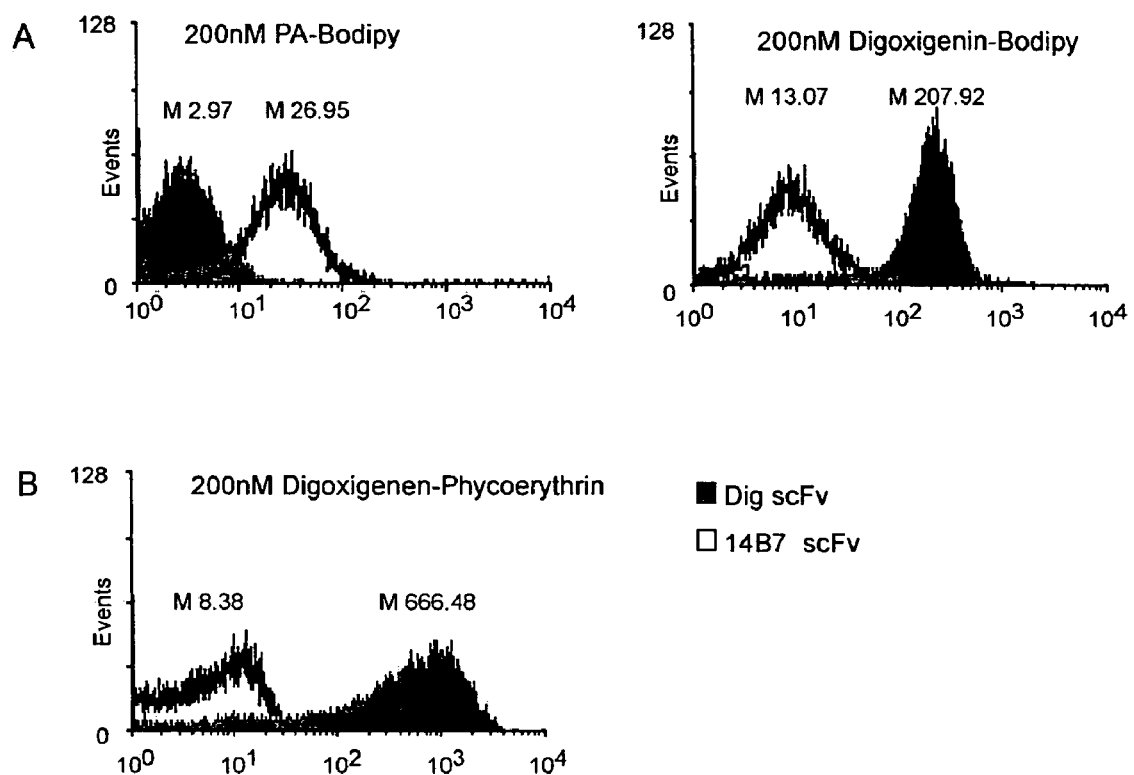
FIG. 7: Examples of targets visualized by APEx.

A sequence encoding the leader peptide and first six amino acids of the mature NlpA (containing the putative fatty acylation and inner membrane targeting sites) was employed for anchoring scFv antibodies to the periplasmic face of the inner membrane. NlpA is a non-essential *E. coli* lipoprotein that exclusively localizes to the inner membrane (Yu et al., 1986; Yamaguchi et al., 1988). Of particular note is the aspartate residue adjacent to the fatty acylated cysteine residue that is thought to be a consensus residue for inner membrane targeting (Yamaguchi et al., 1988). NlpA fusions to the 26-10 anti-digoxin/digoxigenin (Dig) scFv and to the anti-*B. anthracis* protective antigen (PA) 14B7 scFv were constructed and expressed from a lac promoter in *E. coli*. Following induction of the NlpA-[scFv] synthesis using IPTG, the cells were incubated with EDTA and lysozyme to disrupt the outer membrane and the cell wall. The permeabilized cells were mixed with the respective antigens conjugated to the fluorescent dye BODIPY™ (200 nM) and the cell fluorescence was determined by flow cytometry. Treated cells expressing the NlpA-[14B7 scFv] and the NlpA-[Dig scFv] exhibited an approximate 9-fold and 16-fold higher mean fluorescence intensity, respectively, compared to controls (FIG. 7A). Only background fluorescence was detected when the cells were mixed with unrelated fluorescent antigen, indicating negligible background binding under the conditions of the study.

To further evaluate the ability of antibody fragments anchored on the cytoplasmic membrane to bind bulky antigens, the inventors examined the ability of the NlpA-[Dig scFv] to recognize digoxigenin conjugated to the 240 kDa fluorescent protein phycoerythrin (PE). The conjugate was mixed with cells expressing NlpA-[Dig scFv] and treated with EDTA-lysozyme. A high cell fluorescence was observed indicating binding of digoxigenin-PE conjugate by the membrane anchored antibody (FIG. 7B). Overall, the accumulated data demonstrated that in cells treated with Tris-EDTA-lysozyme, scFvs anchored on the cytoplasmic membrane can readily bind to ligands ranging from small molecules to proteins of at least up to 240 kDa in molecular weight. Importantly, labeling with digoxigenin-PE followed by one round of flow cytometry resulted in an over 500-fold enrichment of bacteria expressing NlpA-[Dig scFv] from cells expressing a similar fusion with a scFv having unrelated antigen specificity.

B. Library Screening by APEx

A library of $1\times10^7$ members was constructed by error-prone PCR of the gene for the anti-PA 14B7 scFv and was fused to the NlpA membrane anchoring sequence. DNA sequencing of 12 library clones selected at random revealed an average of 2% nucleotide substitutions per gene. Following induction of NlpA-[14B7 mutant scFv] synthesis with IPTG, the cells were treated with Tris-EDTA-lysozyme, washed, and labeled with 200 nM PA-BODIPY™. Inner membrane integrity was monitored by staining with propidium iodide (PI). A total of $2\times10^8$ bacteria were sorted using an ultra-high throughput Cytomation Inc. MoFlo droplet deflection flow cytometer selectively gating for low PI fluorescence (630 nm emission) and high BODIPY™ fluorescence. Approximately 5% of the cells sorted with the highest 530 nm fluorescence (FL1) were collected, immediately restained with PI alone and resorted as above. Since no antigen was added during this second sorting cycle, only cells expressing antibodies that have slow dissociation kinetics remain fluorescent. The plating efficiency of this population was low, presumably due to a combination of potential scFv toxicity (Somerville et al., 1994; Hayhurst and Harris, 1999), Tris-EDTA-lysozyme treatment and exposure to the high shear flow cytometry environment. Therefore, to avoid loss of potentially high affinity clones, DNA encoding scFvs was rescued by PCR amplification of the approximately $1\times10^4$ fluorescent events recovered by sorting. It should be noted that the conditions used for PCR amplification result in the quantitative release of cellular DNA from the cells which have partially hydrolyzed cell walls due to the Tris-EDTA-lysozyme treatment during labeling. Following 30 rounds of PCR amplification, the DNA was ligated into pAPEx1 and transformed into fresh *E. coli*. A second round of sorting was performed exactly as above, except that in this case only the most fluorescent 2% of the population was collected and then immediately resorted to yield approximately 5,000 fluorescent events.

Figure 8:
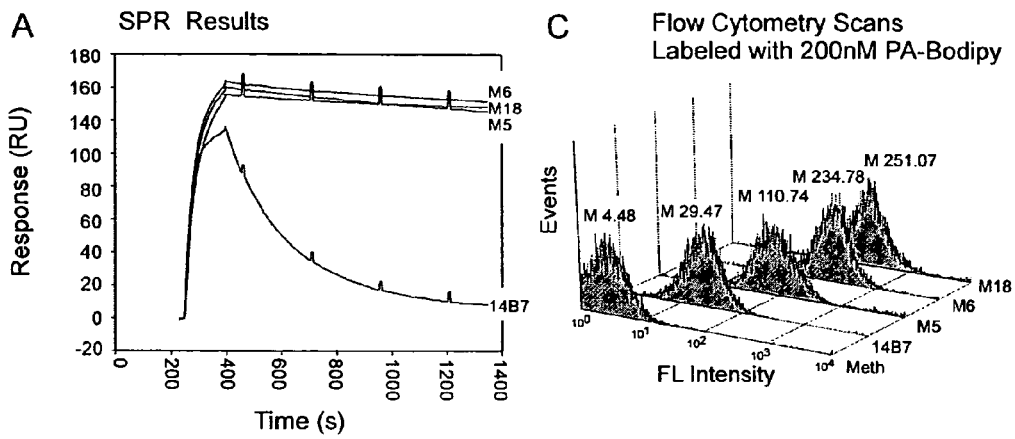
FIG. 8: Analysis of anti-PA antibody fragments selected using APEx (FIG. 8A) Signal Plasmon Resonance (SPR) analysis of anti-PA scAb binding to PA.
Figure 10:
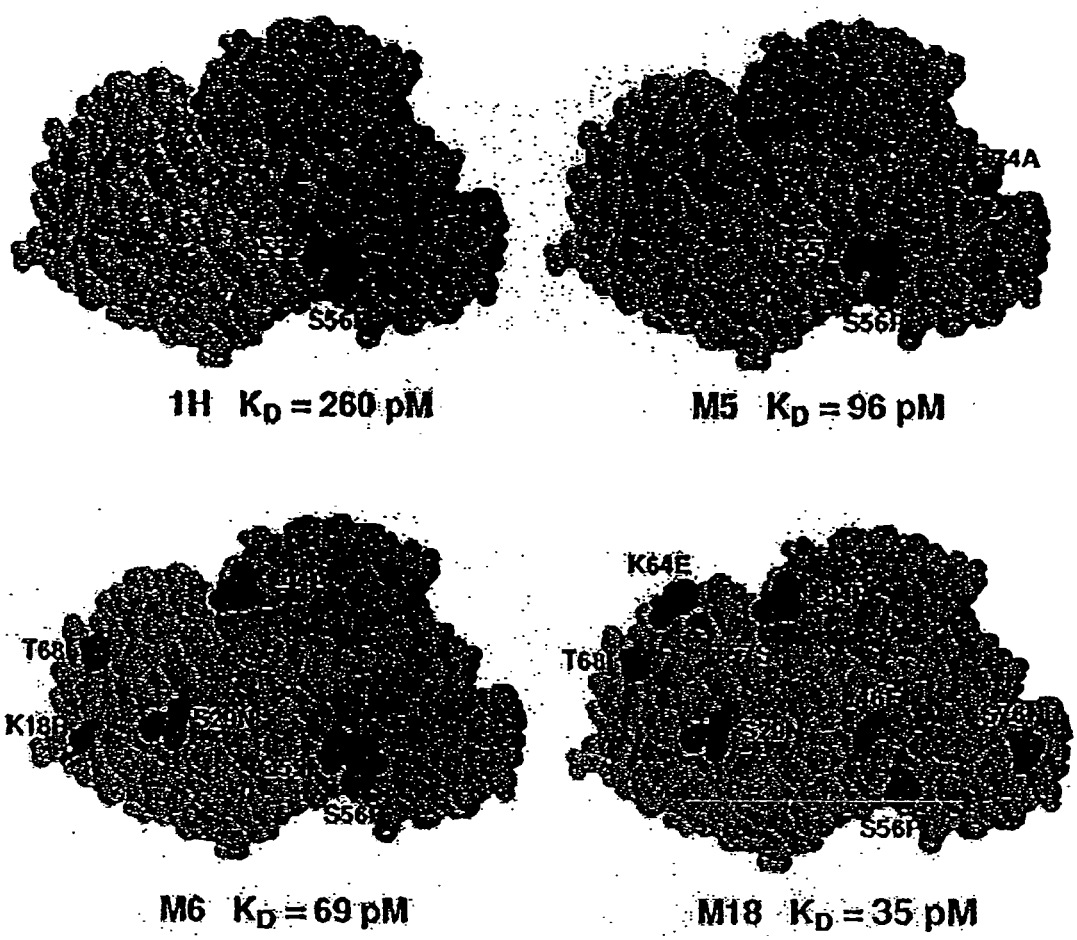
FIG. 10: View from the top of the antibody binding pocket showing the conformation and amino acid substitutions in the 1H, M5, M6 and M18 sequences.

The scFv DNA from the second round was amplified by PCR and ligated into pMoPac16 (Hayhurst et al., 2003) for expression of the antibody fragments in soluble form in the scAb format. A scAb antibody fragment is comprised of an scFv in which the light chain is fused to a human kappa constant region. This antibody fragment format exhibits better periplasmic solubility compared to scFvs (Maynard et al., 2002; Hayhurst, 2000). 20 clones in the scAb format were picked at random and grown in liquid cultures. Following induction with IPTG, periplasmic proteins were isolated and the scAb proteins were rank-ordered with respect to their relative antigen dissociation kinetics, using surface plasmon resonance (SPR) analysis. 11 of the 20 clones exhibited slower antigen dissociation kinetics compared to the 14B7 parental antibody. The 3 scAbs with the slowest antigen dissociation kinetics were produced in large scale and purified by Ni chromatography followed by gel filtration FPLC. Interestingly, all the library-selected clones exhibited excellent expression characteristics and resulted in yields of between 4-8 mg of purified protein per L in shake flask culture. Detailed BIACore analysis indicated that all 3 clones exhibit a substantially lower $K_D$ for PA compared to the parental 14B7 antibody (FIGS. 8A and 8B). The improved $K_D$ resulted primarily from slower antigen dissociation, (i.e. slower $k_{off}$). The highest affinity clone, M18, exhibited $K_D$ of 35 pM, with a $k_{off}$ of $4.2\times10^{-5}$ $M^{-1}sec^{-1}$ which corresponds to a M18-PA half life of 6.6 hours. This represents over 120-fold affinity improvement compared to the parental antibody 14B7 ($K_D$=4.3 nM as determined by BIACore 3000). The mutations identified are given in FIG. 8B and a schematic showing the conformation of the 1H, M5, M6 and M18 antibodies is given in FIG. 10. The mutations for M5 were as follows: in the light chain, Q38R, Q55L, S56P, T74A, Q78L and in the heavy chain, K62R. For M6, the mutations were as follows: S22G, L33S, Q55L, S56P, Q78L AND L94 P, and in the heavy chain, S7P, K19R, S30N, T68I and M80L. For M18, the mutations were as follows: in the light chain, I21V, L46F, S56P, S76N, Q78L and L94P, and in the heavy chain, S30N, T57S, K64E and T68. FIG. 11 shows an alignment of 14B7 scFv (SEQ ID NO:21) and M18 scFv (SEQ ID NO:23) sequences indicating the variable heavy and variable light chains and mutations made. The nucleic acids encoding these sequences are given in SEQ ID NO:20 and SEQ ID NO:22, respectively.

The fluorescence intensity of Tris-EDTA-lysozyme permeabilized cells expressing NlpA fusions to the mutant antibodies varied in proportion to the antigen binding affinity. (FIG. 8C) For example, cells expressing the NlpA-[M18 scFv] protein displayed a mean fluorescence of 250 whereas the cells that expressed the parental 14B7 scFv exhibited a mean fluorescence of 30, compared to a background fluorescence of around 5 (FIG. 8B). Antibodies with intermediate affinities displayed intermediate fluorescence intensities in line with their relative affinity rank. The ability to resolve cells expressing antibodies exhibiting dissociation constants as low as 35 pM provides a reasonable explanation for why three unique very high affinity variants could be isolated and is indicative of the fine resolution that can be obtained with flow cytometric analysis.

The 3 clones analyzed in detail, M5, M6 and M18, contained 7, 12, and 11 amino acid substitutions, respectively. In earlier studies using phage display (Maynard et al., 2002), the inventors isolated a variant of the 14B7 scFv by three cycles, each consisting of 1) mutagenic error prone PCR, 2) five rounds of phage panning and 3) DNA shuffling of the post-panning clones. The best clone isolated in that study, 1H, contained Q55L and S56P substitutions and exhibited a $K_D$ of 150 pM (as determined by a BIACore3000). These two mutations likely increase the hydrophobicity of the binding pocket adding to the mounting evidence that an increase in hydrophobic interactions is a dominant effect in antibody affinity maturation (Li et al., 2003). The same amino acid substitutions are also found in the M5 and M6 clones isolated by APEx. However, the presence of the additional mutations in these two clones conferred a further increase in affinity. It is noteworthy that the M5, M6 and M18 were isolated following a single round of asexual PCR yet they all had higher affinity relative to the best antibody that could be isolated by phage display, even following multiple rounds of sexual mutagenesis and selection.

M18, the highest affinity clone isolated by APEx, contained the S56P mutation but lacked the Q55L substitution found in 1H, M5, and M6. When the Q55L substitution was introduced into M18 by site specific mutagenesis, the resultant ScAb exhibited a further improvement in antigen binding ($K_D$=21 pM) with a $k_{on}$ of $1.1 \times 10^6$ M$^{-1}$ sec$^{-1}$ and a $k_{off}$ of $2.4 \times 10^{-5}$ sec$^{-1}$, corresponding to a complex half life of 11.6 hours. However, the introduction of this mutation reduced the yield of purified protein more than 5-fold to 1.2 mg/L in shake flask culture. The modified M18 sequence is given in SEQ ID NO:25 and the nucleic acid encoding this sequence is given in SEQ ID NO:24.

C. APEx of Phage Displayed scFv Antibodies

Figure 9:
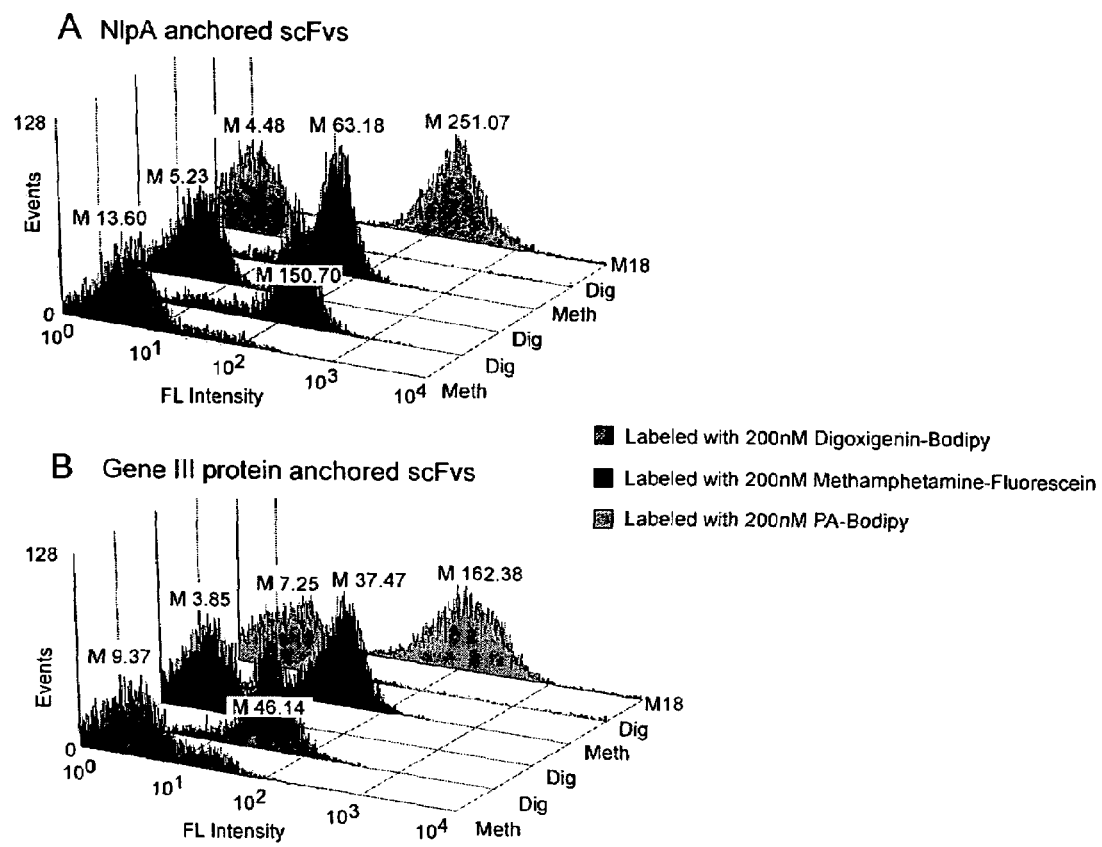
FIG. 9: N-Terminal vs. C-Terminal anchoring strategy comparison.

Numerous antibody fragments to important therapeutic and diagnostic targets have been isolated from repertoire libraries screened by phage display. It is desirable to develop a means for rapid antigen binding analysis and affinity maturation of such antibodies without the need for time consuming subcloning steps. Antibodies are most commonly displayed on filamentous phage via fusion to the N-terminus of the phage gene 3 minor coat protein (g3p) (Barbas et al., 1991). During phage morphogenesis, g3p becomes transiently attached to the inner membrane via its extreme C-terminus, before it can be incorporated onto the growing virion (Boeke and Model, 1982). The antibody fragments are thus both anchored and displayed in the periplasmic compartment. Therefore, the inventors evaluated whether g3p fusion proteins can be exploited for antibody library screening purposes using the APEx format. The high affinity anti-PA M18 scFv discussed above, the anti-digoxin/digoxigenin 26-10 scFv, and an anti-methamphetamine scFv (Meth) were cloned in frame to the N-terminus of g3p downstream from a lac promoter in phagemid pAK200, which is widely used for phage display purposes and utilizes a short variant of gene III for g3p display (Krebber et al., 1997). Following induction with IPTG, cells expressing scFv-g3p fusions were permeabilized by Tris-EDTA-lysozyme and labeled with the respective fluorescent antigens (FIG. 9). High fluorescence was obtained for all three scFvs only when incubated with their respective antigens. Significantly, the mean fluorescence intensity of the scFvs fused to the N-terminus of g3p was comparable to that obtained by fusion to the C-terminus of the NlpA anchor. The results in FIG. 9 demonstrate that: (i) large soluble domains can be tethered N-terminally to a membrane anchor; (ii) antibody fragments cloned into phagemids for display on filamentous phage can be readily analyzed by flow cytometry using the APEx format, and (iii) scFv antibodies can be anchored on the cytoplasmic membrane either as N- or C-terminal fusions without loss of antigen binding.

D. Discussion

The inventors have developed a allowing efficient selection of high affinity ligand-binding proteins, and particularly scFv antibodies, from combinatorial libraries. In one aspect, APEx is based on the anchoring of proteins to the outer side of the inner membrane, followed by disruption of the outer membrane prior to incubation with fluorescently labeled antigen and FC sorting. This strategy offers several advantages over previous bacterial periplasmic and surface display approaches: 1) by utilizing a fatty acylated anchor to retain the protein in the inner membrane, a fusion as short as 6 amino acids is all that was required for the successful display, potentially decreasing deleterious effects that larger fusions may impose; 2) the inner membrane lacks molecules such as LPS or other complex carbohydrates that can sterically interfere with large antigen binding to displayed antibody fragments; 3) the fusion must only traverse one membrane before it is displayed; 4) both N- and C-terminal fusion strategies can be employed; and 5) APEx can be used directly for proteins expressed from popular phage display vectors. This latter point is particularly important because it enables hybrid library screening strategies, in which clones from a phage panning experiment can be quantitatively analyzed or sorted further by flow cytometry without the need for any subcloning steps.

APEx can be employed for the detection of antigens ranging from small molecules (e.g. digoxigenin and methamphetamine<1 kDa) to phycoerythrin conjugates (240 kDa). In fact, the phycoerythrin conjugate employed in FIG. 3B is not meant to define an upper limit for antigen detection, as it is contemplated that larger proteins may be used as well.

In the example, genes encoding scFvs that bind the fluorescently labeled antigen, were rescued from the sorted cells by PCR. An advantage of this approach is that it enables the isolation of clones that are no longer viable due to the combination of potential scFv toxicity, Tris-EDTA-lysozyme disruption, and FC shear forces. In this way, diversity of isolated clones is maximized. Yet another advantage of PCR rescue is that the amplification of DNA from pooled cells can be carried out under mutagenic conditions prior to subcloning.

Thus, following each round of selection random mutations can be introduced into the isolated genes, simplifying further rounds of directed evolution (Hanes and Pluckthun, 1997). Further, PCR conditions that favor template switching among the protein encoding genes in the pool may be employed during the amplification step to allow recombination among the selected clones. It is likely that PCR rescue would be advantageous in other library screening formats as well.

An important issue with any library screening technology is the ability to express isolated clones at a high level. Existing display formats involve fusion to large anchoring sequences which can influence the expression characteristics of the displayed proteins. For this reason, scFvs that display well may not necessarily be amenable to high expression in soluble form as non-fusion proteins (Hayhurst et al., 2003). In contrast, the short (6 amino acid) tail that may be used for N-terminal tethering of proteins onto the cytoplasmic membrane in the current invention is unlikely to affect the expression characteristics of the fusion. Consistent with this hypothesis, all three affinity enhanced clones to the anthrax PA toxin isolated by APEx exhibited excellent soluble expression characteristics despite having numerous amino acid substitutions. Similarly, well-expressing clones have been obtained in the affinity maturation of a methamphetamine antibody, suggesting that the isolation of clones that can readily be produced in soluble form in bacteria at a large scale might be an intrinsic feature of selections with the invention.

In this example, the inventors employed APEx for affinity maturation purposes and have engineered scFvs to the *B. anthracis* protective antigen exhibiting $K_D$ values as low as 21 pM. The scFv binding site exhibiting the highest affinity for PA has been humanized, converted to full length IgG and its neutralizing potential to anthrax intoxication is being evaluated in preclinical studies. In addition to affinity maturation, APEx can be exploited for several other protein engineering applications including the analysis of membrane protein topology, whereby a scFv antibody anchored in a periplasmic loop is able to bind fluorescent antigen and serves as a fluorescent reporter, and also, the selection of enzyme variants with enhanced function. Notably, APEx can be readily adapted to enzyme library sorting, as the cell envelope provides sites for retention of enzymatic catalytic products, thereby enabling selection based directly on catalytic turnover (Olsen et al., 2000). The inventors are also evaluating the utilization of APEx for the screening of ligands to membrane proteins. In conclusion, it has been demonstrated that anchored periplasmic expression has the potential to facilitate combinatorial library screening and other protein engineering applications.

E. Materials and Methods

1. Recombinant DNA Techniques

The leader peptide and first six amino acids of the mature NlpA protein flanked by NdeI and SfiI sites was amplified by whole cell PCR of XL1-Blue (Stratagene, CA) using primers BRH#08 5'-GAAGGAGATATACATATGAAACTGACAA-CACATCATCTA-3' (SEQ ID NO:6) and BRH#09 5'-CTGGGCCATGGCCGGCTGGGCCTCGCT-GCTACTCTGGTCGCAACC-3' (SEQ ID NO:7). The resulting NlpA fragment was used to replace the pelB leader sequence of pMoPac1 (Hayhurst et al., 2003) via NdeI and SfiI to generate pAPEx1, scFv specific for digoxin (Chen et al., 1999), *Bacillus anthracis* protective antigen PA (Maynard et al., 2002) and methamphetamine were inserted downstream of the NlpA fragment in pAPEx1 via the non-compatible SfiI sites. Corresponding g3p fusions of the scFv were made by cloning the same genes into phage display vector pAK200 (Krebber et al., 1997).

2. Growth Conditions

*E. coli* ABLE C™ (Stratagene) was the host strain used throughout. *E. coli* transformed with the pAPEx1 or pAK200 derivatives were inoculated in Difco™ Terrific Broth (TB) supplemented with 2% glucose and chloramphenicol at 30 µg/ml to an OD600 of 0.1. Cell growth and induction were performed as described previously (Chen et al., 2001). Following induction, the cellular outer membrane was permeabilized as described (Neu and Heppel, 1965). Briefly, cells (equivalent to approx 1 ml of 20 OD600) were pelleted and resuspended in 350 µl of ice-cold solution of 0.75M sucrose, 0.1M Tris-HCl pH8.0, 100 µg/ml hen egg lysozyme. 700 µl of ice-cold 1 mM EDTA was gently added and the suspension left on ice for 10 min. 50 µl of 0.5 M MgCl2 was added and the mix left on ice for a further 10 min. The resulting cells were gently pelleted and resuspended in phosphate buffered saline (1×PBS) with 200 nM probe at room temperature for 45 min, before evaluation by FC.

3. Fluorescent Probe

The synthesis of digoxigenin-BODIPY has been described previously (Daugherty et al., 1999). Methamphetamine-fluorescein conjugate was a gift from Roche Diagnostics. Purified PA protein kindly provided by S. Leppla NIH, was conjugated to BODIPY™ at a 1 to 7 molar ratio with bodipy FL SE D-2184 according to the manufacturers instructions. Unconjugated BODIPY™ was removed by dialysis.

To synthesize digoxigenin-phycoerythrin, R-phycoerythrin and 3-amino-3-dioxydigxigenin hemisuccinamide, succinimidyl ester (Molecular Probes) were conjugated at a 1 to 5 molar ratio according to the manufacturers instructions. Free digoxigenin was removed by dialysis in excess PBS.

4. Affinity Maturation of scFv Libraries with FC

Libraries were made from the 14B7 parental scFv using error prone PCR using standard techniques (Fromant et al., 1995) and cloned into the pAPEx1 expression vector. Upon transformation, induction and labeling the cells were then stained with propidium iodide (PI emission 617 nm) to monitor inner membrane integrity. Cells were analyzed on a MoFlo (Cytomation) droplet deflection flow cytometer using 488 nm Argon laser for excitation. Cells were selected based on improved fluorescence in the Fluorescein/Bodipy FL emission spectrum detecting through a 530/40 band pass filter and for the absence of labeling in PI emission detecting through a 630/40 band pass filter.

*E. coli* captured after the first sort were immediately resorted through the flow cytometer. Subsequently, the scFv genes in the sorted cell suspension were amplified by PCR. Once amplified, the mutant scFv genes were then recloned into pAPEx1 vector, retransformed into cells and then grown overnight on agar plates at 30° C. The resulting clones were subjected to a second round of sorting plus resorting as above, before scFv genes were subcloned into pMoPac16 (Hayhurst et al., 2003) for expression of scAb protein.

5. Surface Plasmon Resonance Analysis

Monomeric scAb proteins were purified by IMAC/size-exclusion FPLC as described previously (Hayhurst et al., 2003). Affinity measurements were obtained via SPR using a BIACore3000 instrument. Approximately 500 RUs of PA was coupled to a CM5 chip using EDC/NHS chemistry. BSA was similarly coupled and used for in line subtraction. Kinetic analysis was performed at 25° C. in BIA HBS-EP buffer at a flow rate 100 μl/min. Five two fold dilutions of each antibody beginning at 20 nM were analyzed in triplicate.

Example 7

MalF Topology Prediction

A method was sought for confirming the accuracy of a fluorescent probe-based screening system using *E. coli* MalF as a model protein, of which intrinsic topology (8 TMHs) has been fully elucidated (Ehrmann et al., 1990). The six representative positions were arbitrarily chosen from MalF polypeptide sequence as follows: Y62, G313 and G407 (the positions located in the known cytoplasmic loops), and V175, M350 and A461 (the positions located in periplasmic loops). A series of expression plasmids were constructed bearing the truncated MalF fused with either of the two topology-reporter candidates at the defined positions. To construct these MalF-fused expression series, several primers were synthesized. These sequences are described in Table 1.

Figure 12A:
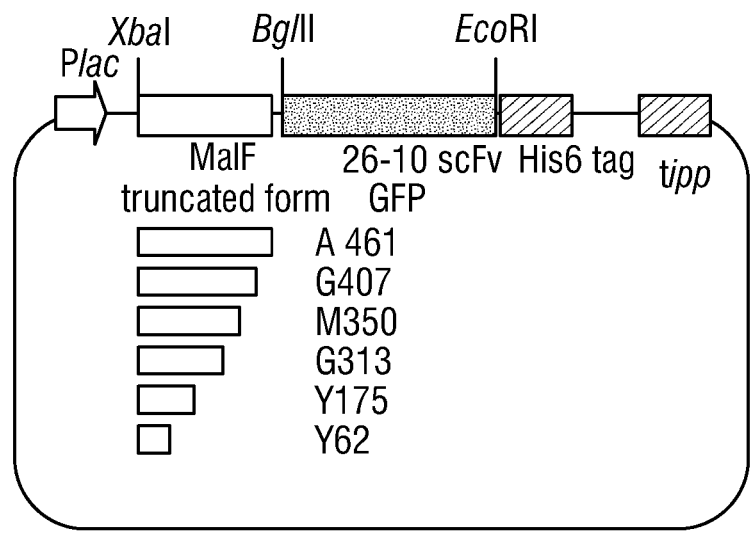
(FIG. 12A) Simple structure of MalF-fused expression system and (FIG. 12B) fusion points in MalF protein.
Figure 12B:
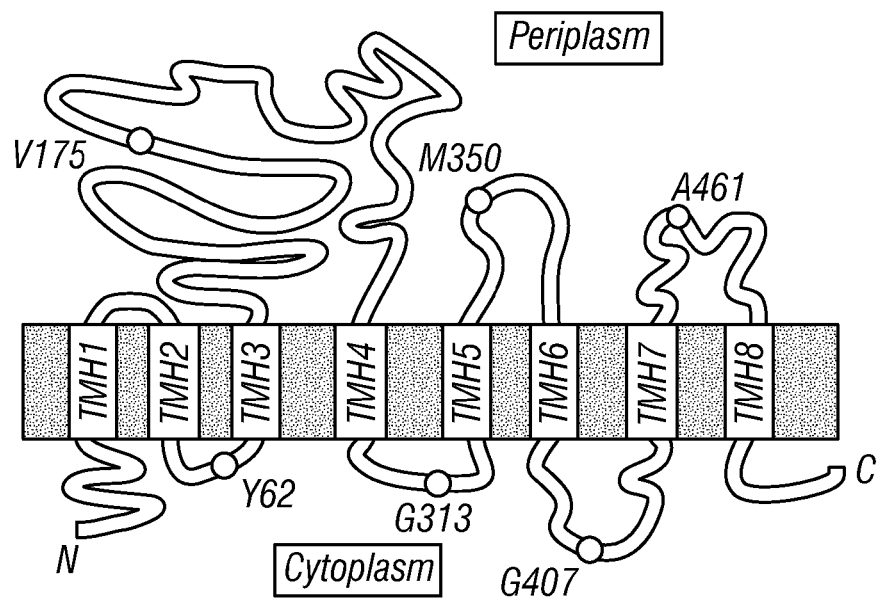
FIG. 12.

For the PCR amplification of MalF truncated forms (Y62, V175, G313, M350, G407 and A461), primers MalF-R1, MalF-R2, MalF-R3, MalF-R4, MalF-R5 and MalF-R6 were used as reverse primers, respectively. Primer MalF-F1 was used as a forward primer in all PCR reactions. Each PCR product was digested by two restriction enzymes (BglII and XbaI). For the amplification of 26-10 scFv, primers 2610-F1 and 2610-R1 were used and pHEN2.dig26-10 containing 26-10 scFv gene (Chen et al., 2001) was used as a template DNA. For the amplification of GFP, primers GFP-F1 and GFP-R1 were used. pGFPmut2 containing a GFP variant gene (Drew et al., 2001) was used as a template DNA. Each PCR product was digested by two restriction enzymes (BglII and EcoRI). MalF truncated forms and reporter genes (26-10 scFv or GFP) were ligated and then cloned into pMoPac1 digested with XbaI and EcoRI. FIG. 12 shows the simple structure of MalF-fused expression system and fusion points in MalF protein.

Each expression vector was transformed into *E. coli* MC4100, and overnight cultures of the cells with the respective MalF-topology reporters were subcultured (1:100 dilution) into fresh Difco™ Terrific Broth (TB, Difco Co. USA) containing 35 μg/ml chloramphenicol, and allowed to grow at 37° C. with vigorous shaking to $OD_{600}$=0.6-0.7. The cultures were then transferred to a 25° C. shaker and allowed to a equilibrate for 30 min. Subsequently, isopropyl β-D-thiogalactoside (IPTG, Sigma Co. USA) was added to a final concentration of 0.1 mM, and the cultures were incubated for an additional 4 h prior harvesting. For flow cytometric analysis of 26-10 scFv fusion clones, 0.1 mL of cells from the flask culture were mixed with 100 nM of digoxin-BODIPY probe in 0.9 mL of 5xPBS (phosphate buffered saline) and after 1 hr of incubation at room temperature with shaking, the cells were collected by centrifugation.

Figure 13:
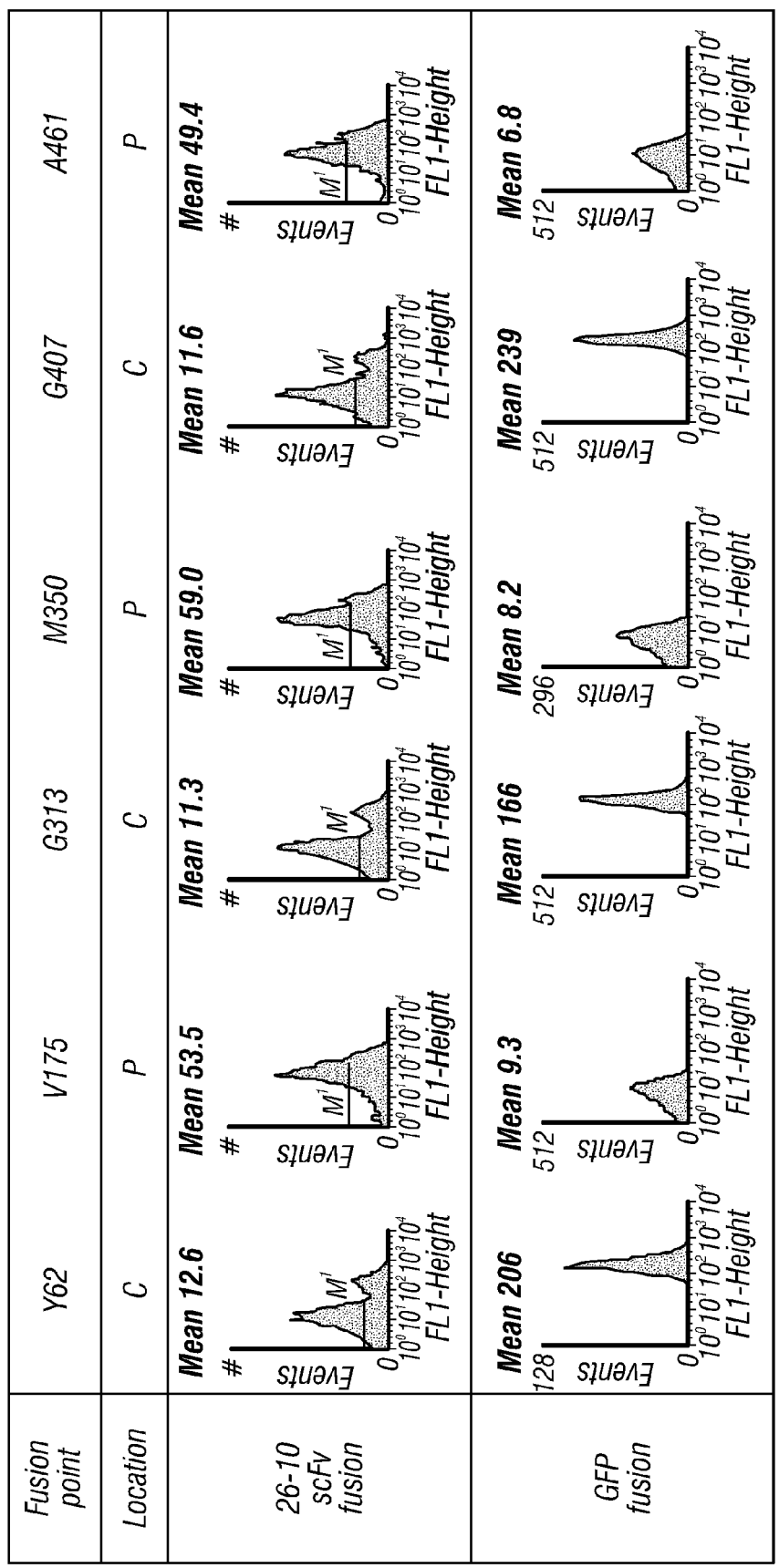
FIG. 13: Flow cytometric analysis of MalF-fused clones (C, cytoplasmic location; P, periplasmic location of fusion points).

The cells were resuspended in 1 mL of 1xPBS and a 5 μL aliquot was diluted into 2 mL of 1xPBS and labeled with propidium iodine (PI) for flow cytometric detection of non-viable cells. For flow cytometric analysis of GFP fusion clones, 2 μL of cells from the flask culture were diluted directly into 2 mL of 1xPBS and labeled with PI. Flow cytometric analysis was performed with a Becton-Dickinson FACS caliber. The results of the flow-cytometric evaluation of the two topological-reporter candidates are summarized in FIG. 13.

In each fusion case, the topological reporter gave the host cell appropriate signal intensity corresponding to its expected location. For example, the clones with the cytoplasmic reporter (GFP) fused at MalF cytoplasmic loops (Y62, G313 or G407) showed nearly 20 fold higher fluorescence-mean values than those fused at the periplasmic loops (V175, M350, or A461). Similarly, the 26-10 scFv conferred distinguishable fluorescent signals to the host cells only when it was fused at either of the known periplasmic loops. Although the clones with the periplasmic reporter fused at the cytoplasmic loop (at Y62, G313 or G407) had a minor population that shows a higher fluorescent intensity, such clones with noise fraction could be eliminated by the repetitive sorting of the selected clones.

TABLE 1

List of primers and their sequences used for construction of MalF-fused expression series.

| Primer Name | Sequences (5' → 3') | |
|---|---|---|
| MalF-F1 | GCTCTAGAATGAGGAAGAACCCCATGG | (SEQ ID NO:26) |
| MalF-R1 | GGCAGATCTGGCTTTACGATTGGCGAAA | (SEQ ID NO:27) |
| MalF-R2 | GGCAGATCTCACGCGCAGATTCGCGTC | (SEQ ID NO:28) |
| MalF-R3 | GGCAGATCTGCCGCGCAACGCTTCCC | (SEQ ID NO:29) |
| MalF-R4 | GGCAGATCTCATGTTGATTTCACCGAA | (SEQ ID NO:30) |
| MalF-R5 | GGCAGATCTGCCATCCATTGCTGAGGC | (SEQ ID NO:31) |
| MalF-R6 | GGCAGATCTGGCTGGCGTGGTCGTGCC | (SEQ ID NO:32) |
| 2610-F1 | GGCAGATCTGGAGGTGGAAGCGAGGCCCAGCCGG | (SEQ ID NO:33) |
| 2610-R1 | GGAATTCGGCCCCCGAGGCCGATTTGATCTCG | (SEQ ID NO:34) |
| GFP-F1 | CGAAGCTTAGATCTAGTAAAGGAGAAGAACTTT | (SEQ ID NO:35) |
| GFP-R1 | GGAATTCTTTGTATAGTTCATCCATGCC | (SEQ ID NO:36) |

Example 8

TatC Topology Prediction

TatC (259 amino acids in length) is a conserved inner membrane protein (IMP) that plays a pivotal role in the TAT (Twin-Arginine Translocation) system (Berks, 1996). In *E. coli*, four integral membrane proteins, TatA, TatB, TatC, and TatE are involved in the system. Structural prediction of the components indicates that TatA and TatB share a similar and simple overall structure with single-span TMH and an amphipathic α-helix at their C-terminal region, whereas TatC is predicted to be a polytopic membrane protein with 6 TMHs, of which N- and C-termini are exposed to the cytoplasmic face (Buchanan et al., 2002; Drew et al., 2001). An alternative, conflicting model for TatC topology has been reported by Gouffi et al. (Gouffi et al., 2002). The alternative 4 TMHs model has been deduced from experimental results obtained by the analysis of the truncated TatC protein fused with a conventional topology marker including PhoA (as a periplasmic reporter) or β-glucuronidase (as a cytoplasmic reporter). The second putative cytoplasmic loop between the 4th and 5th TMH in the 6 TMHs model is allocated to the periplasmic space together with the both TMHs in their 4 TMHs model.

For the exhaustive and quantitative analysis of every possible fusion point, a set of complementary fusion (26-10 scFv and GFP) libraries of TatC was constructed with various C-terminal endpoints using Thio-ITCHY. First, plasmid pTOPO-2610 was constructed by cloning the 26-10 scFv gene (Chen et al., 2001) using the primers Topo-F (5'-GC ACTAGTAGATCTCATATGGAGCCCGGGCATCCGGG GAGCTC-3' (SEQ ID NO:37)), Topo-2610-F (5'-CGGGCATCCGGGGAGCTCAGGCCCAGC-CGGCCATG-3' (SEQ ID NO:38)) and Topo-2610-R (5'-GGCGAATTCGGCCCCCGAGG-3' (SEQ ID NO:39)), which introduced the unique restriction sites of SpeI and EcoRI (underlined) at the 5' and 3'-ends of the 26-10 scFv gene, respectively, and enabled cloning of this sequence into XbaI-EcoRI digested pMoPac1. Plasmid pTOPO-GFP was constructed by cloning the GFPmut2 variant (Cormack et al., 1996) using the primers Topo-F, Topo-GFP-F (5'-CGGGCATCCGGGGAGCTCCAATGAG-TAAAGGAGAAGAACTTT-3'(SEQ ID NO:40)) and Topo-GFP-R (5'-GCGAATTCTTTGTATAGTTCATCCA TGCC-3'(SEQ ID NO:41)). The SpeI-EcoRI digested PCR product was then cloned into XbaI-EcoRI digested pMoPac1.

Figure 14:
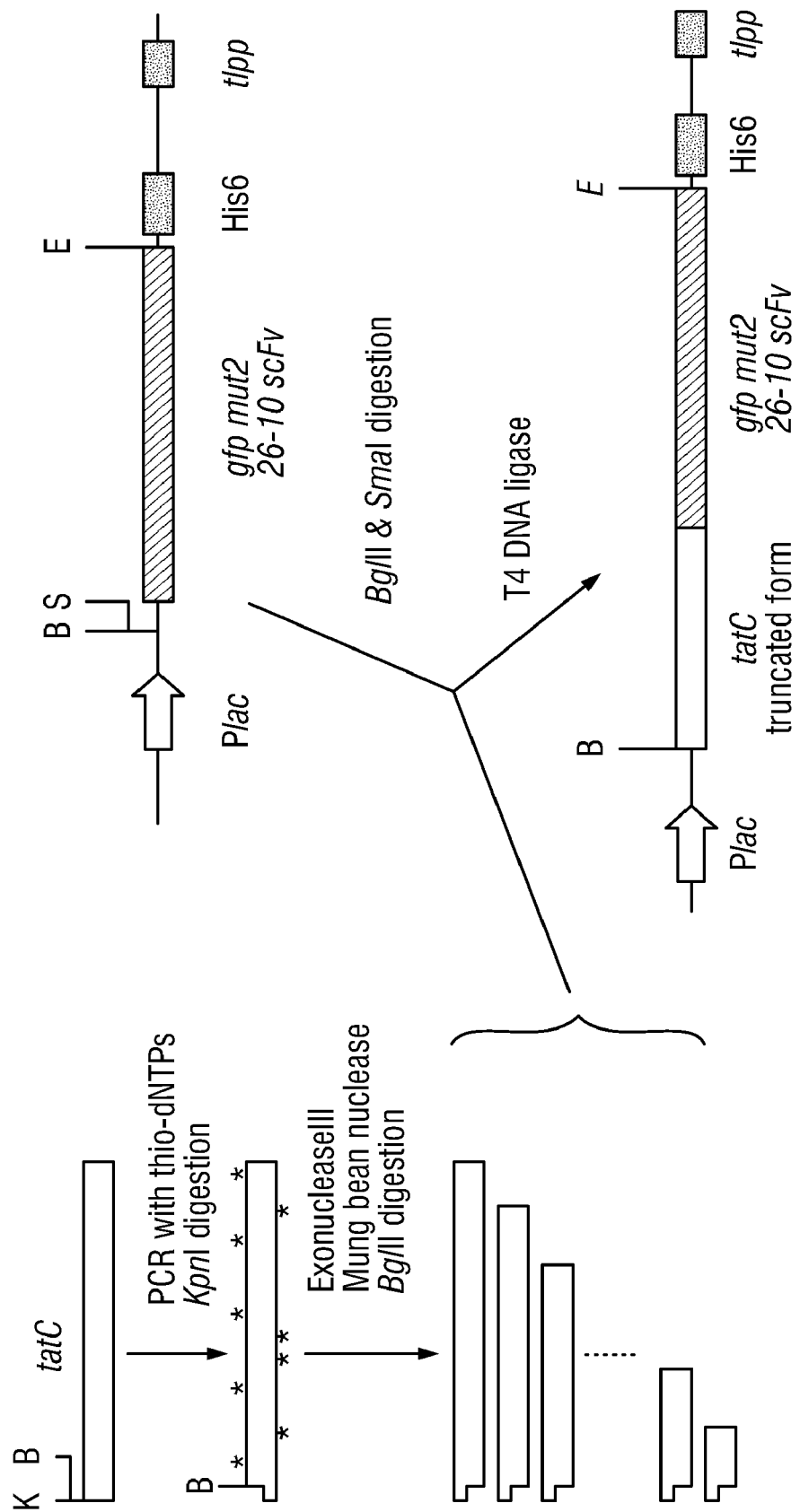
FIG. 14: Library construction of truncated TatC fused 26-10 scFv/GFP by THIO-ITCHY method (K, KpnI; B, BglII; E, EcoRI; S, SmaI; His6, histidine hexamer tag; tlpp, lpp terminator)

Preparation of randomly truncated tatC fused with reporter gene (gfp or 26-10 scFv) was carried out based on the method termed THIO-ITCHY (Lutz et al., 2001) with some modifications. The entire sequence for the tatC coding region was amplified using gene-specific primers TatC-F (5'-GGC GGTACCGAAGATCTGAAGGAGATATACACATGTCTG TAGAAGATACTC-3'(SEQ ID NO:42)) and TatC-R (5'-CCTGACGGGCGGTTGAATTTCTTCTTCAGTTT TTTCGCTTTCT-3'(SEQ ID NO:43)), where the underlined sequences indicate KpnI and BglII restriction sites, with the existence of appropriate concentration (20 μM) of α-phosphothioate dNTPs. After the digestion by KpnI, the amplified thio-tatC fragments were subjected to treatment with exonuclease III, followed by mungbean nuclease trimming to give blunt-ended DNA fragments with various C-terminal endpoints. The blunt-ended fragments were digested by BglII, then ligated with the BglII-SmaI fragment of pTOPO-GFP or that of pTOPO-26.10, followed by transformation of *E. coli* Jude1 (DH10B derivative that harbors the F' factor derived from XL1-blue) to make the fusion libraries ($2.0 \times 10^4$ and $3.0 \times 10^4$ independent colonies for 26-10 scFv and GFP fusion libraries, respectively). The size variation of the truncated TatC was analyzed by colony-directed PCR of individual clones using TatC N-terminal region-specific and the reporter gene-specific primers. The amplified fragments showed a considerable diversity in sizes, suggesting that the random truncation of TatC had been successfully performed. The size diversity also suggested that the constructed libraries consisted of a series of clones with every possible fusion point. FIG. 14 shows the simple diagram of library construction.

The plasmids were then purified from the *E. coli* Jude1 library and transformed into *E. coli* MC4100, which was used as a host cell for screening the library. Cell cultures and sample preparations were accomplished using the methods described in the previous example. Sorting by flow cytometry was performed with a Becton-Dickinson FACS caliber, and the desired cell population was gated by setting appropriate SSC (side-scattered light), FSC (Forward-scattered light), FL1, and FL2 windows (FL1 is used to monitor GFP fluorescence and FL2 is used to monitor PI fluorescence) and cells were sorted in exclusion mode. Typically, ca. $2 \times 10^6$ cells were examined in 30 min and 10,000 to 15,000 events were sorted. The sorted cells were recovered as 20 mL fractions and were diluted into an equal volume of 2 times concentrated TB medium. The collected solution was sterilely filtered (0.2 μm pore size), and the filters were placed on TB medium plates containing chloramphenicol. For the second round of sorting, the cells grown on the plate were collected and inoculated into new TB medium, and then sorted using the methods described above. After the second round of sorting and incubation on agar plates, forty-eight clones out of the resulting ca. 3,000 colonies were randomly chosen. The 48 clones were then subjected to the analysis of monoclonal fluorescent intensity using the same induction and sorting conditions that were used in the selection rounds. Every clone among the selected 48 clones showed significantly higher (from 15 to 100 times) fluorescent mean-values than that of the negative control (host cell without plasmid). Sequences of the sorted cells were determined by using API Prism 3700 (Applied Biosystems, Foster city, Calif.).

Figure 15:
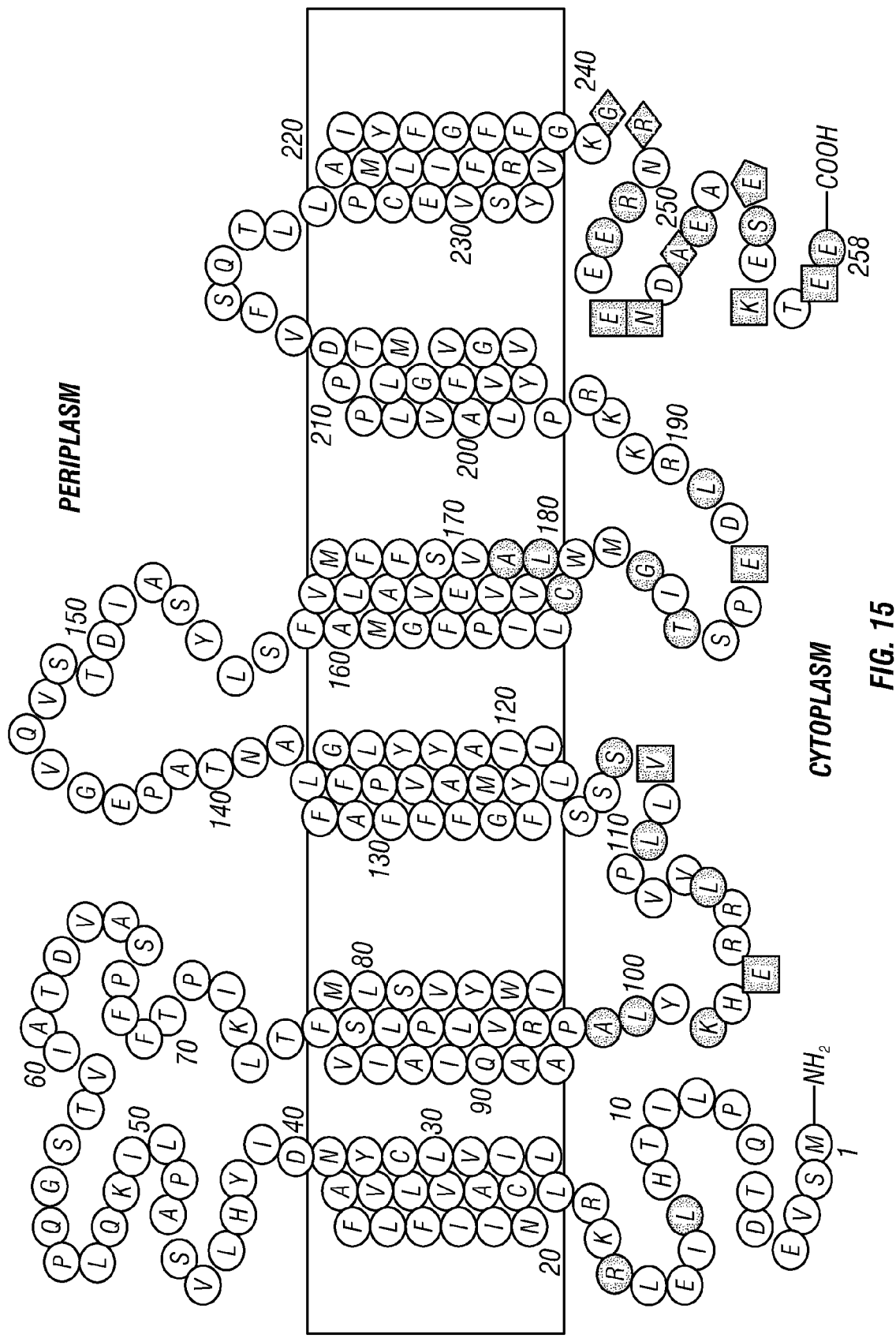
FIG. 15: TatC-topology prediction based on the GFP fusion clones. Dark background symbols represent the fusion points identified by sequencing. Among these, square-shaped symbols designate the fusion points of clones represented twice, diamond-shaped symbols designate clones represented three times, and pentagonal shaped symbol designate clones represented four times.

DNA sequencing analysis of the 48 clones allowed identification of 31 distinctive fusion points on the primary amino-acid sequence of TatC. The identified fusion points were present in (i) N- and C-terminal regions, (ii) a stretch between the putative 2nd and 3rd TMHs, or (iii) another stretch between the putative 4th and 5th TMHs without any exceptions. Based on the identified fusion points and the putative TMHs predicted by the hydropathy analysis, the deduced topology model of TatC was delineated as shown in FIG. 15. The information for the positions and frequencies of the identified fusion points are also embedded in FIG. 15. The deduced structure was perfectly consistent with the originally predicted 6 TMHs model, rather than the 4 TMHs model (Gouffi et al., 2002). In addition, the selected clones of which fusion points locates at L177, C179, G182, E187 or L189, whose positions are in the controversial loop between 4th and 5th TMHs, showed significant fluorescent intensities when they were individually tested, strongly supporting the 6 TMHs model. The results confirmed the ability to delineate functional anchor sequences from among a population of poorly or non-functional candidate anchor sequences.

Flow-cytometric sorting of the clones with the periplasmic reporter 26-10 scFv was similarly performed using *E. coli* D21F2 as a host strain. From the *E. coli* Jude1 library, plasmids were purified and then transformed into *E. coli* D21F2. The cultured cells expressing TatC fused 26-10 scFv were labeled with the digoxin-BODIPY probe (100 nM) in 1×PBS buffer. After labeling for 45 min at room temperature, sorting by flow cytometry was performed with a Becton-Dickinson FACS caliber, and the desired cell population was gated by setting appropriate SSC, FSC, FL1, and FL2 windows (FL1 is used to monitor digoxin-BODIPY fluorescence and FL2 is used to monitor PI fluorescence) and cells were sorted in exclusion mode. After the second round of sorting and incubation on agar plates containing 35 μg/mL of chloramphenicol at 30° C., forty clones out of the resulting ca. 1,200 colonies were randomly chosen, then subjected to the analysis of monoclonal fluorescent intensity using the same induction and sorting conditions that were used in the selection rounds. All forty clones showed up to 10 times higher fluorescence mean values than that of the negative control (the host cells without plasmid), indicating that the sorting and selection of clones had been performed with accuracy.

Figure 16:
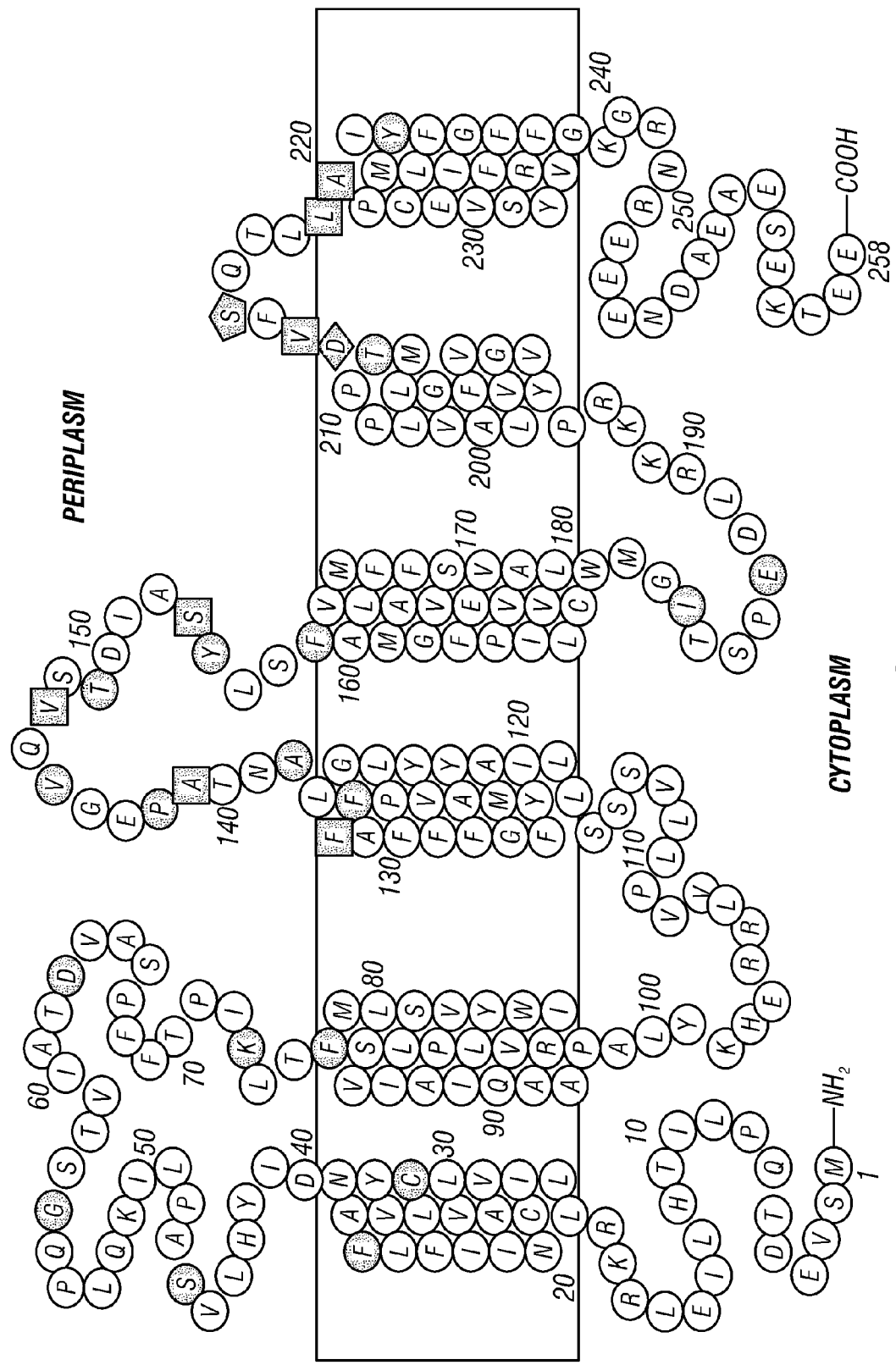
FIG. 16: TatC-topology prediction based on the 26-10 scFv fusion clones. Dark background symbols represent the fusion points identified by sequencing. Among these, square-shaped symbols designate the fusion points of clones represented twice, diamond-shaped symbols designate clones represented three times, and pentagonal-shaped symbol designate clones represented four times.

As a result of DNA sequencing analysis of the 40 clones, 28 distinctive fusion points were identified. The locations and frequencies of the identified fusion points are depicted on the previously deduced 6 TMHs model (FIG. 16). It was found that more than 97% of the selected clones (38 out of the tested 40 clones) had their fusion points with the periplasmic reporter on the regions deduced as periplasmic loops, or the borders of the putative TMHs with the periplasmic loops in the 6TMHs model.

In the study, two exceptional fusion points were found at I183 and E187, the region responsible for the confliction between the 4- and 6-TMHs models. It indicates that the clones with the periplasmic reporter at these positions were able to display the active scFv to the periplasm. Nevertheless, the frequency of those clones was low in the selected clones compared with those in the adjacent loops. In addition, although their fluorescent intensities were approximately 2 times higher than that of the negative control, the results of the flow-cytometric analysis of these two clones showed 3 to 5 fold lower fluorescent intensities than those of the other selected clones. Together with the topological map obtained in the GFP-fusion library analysis (FIG. 15), it was concluded that these two clones were false-positive clones, potentially due to the misallocation of the scFv to the periplasm. While this indicates the potential for some false positives, these can be easily distinguished from the true-positive clones by their frequencies in the selected library. As demonstrated, even a semi-statistic (n<50) sampling and fusion points identification is likely sufficient to spot false-positive clones, since the populations of true-positive clones have been highly enriched in the selected pool compared with the false-positive clones with ambiguous signals.

To verify the 6TMH model of TatC, several positions were chosen around the controversial loop, such as G56, A98, S153, E187, L189, A200, and V212, as pre-defined fusion points. A set of topological reporter fusions was prepared connected at those defined positions. The fluorescent intensities of the respective clones were analyzed using flow-cytometry. The obtained mean-fluorescent value of each clone was summarized in Table 2. At positions G56, A98, S153 and V212, both fusion clones showed the clear differences in their fluorescent intensities, which were well matched to the 6 TMH topology model. GFP fusion clones at E187 and L189 positions exhibited higher fluoresecent intensities than the other clones. However, 26-10 scFv fusion clones at the same fusion positions showed much lower fluorescent intensities even though their intensities were still higher than that of negative control (A98). Interestingly, at the A200 position, GFP fusion showed some intermediate intensities and 26-10 scFv fusions showed lower signal similar to negative control (A98). This data indicated that the A200 position is placed inside the membrane, which is in agreement with the 6 TMHs model.

TABLE 2

Fluorescent Intensities of 26-10 scFv and GFP Fusion Clones

| Fusion points | Location | Fluorescent intensity[a] | |
|---|---|---|---|
| | | 26-10 scFv fusion | GFP fusion |
| G56 | 1st periplasmic loop | 115 | 10.4 |
| A98 | 1st cytoplasmic loop | 10.9 | 488.5 |
| S153 | 2nd periplasmic loop | 120 | 7.1 |
| E187 | 2nd cytoplasmic loop | 23.6 | 563.4 |
| L189 | 2nd cytoplasmic loop | 37.9 | 717.1 |
| A200 | 5th TMH | 12.6 | 116.6 |
| V212 | 3rd periplasmic loop | 102 | 7.9 |

[a]Mean value of fluorescence determined by flow cytometry

Example 9

Library Construction for Discovery of Sequences for Tethering Proteins on the Membrane In order to screen for sequences useful for tethering proteins onto the inner membrane, a library was constructed by the randomization of the sequences encoding NlpA (CDQSSS) (SEQ ID NO:44). As discussed in the previous example, NlpA is a lipoprotein that localizes to the inner membrane. Since the first amino acid (Cys) of NlpA is necessary for lipidation with lipid of the inner membrane, only the next five amino acids (DQSSS) were randomized. In this library, some protein may be localized in the inner membrane, some protein may be localized in the outer membrane, and some protein may be present in the periplasm without localizing to either membrane. When these cells are converted to spheroplasts by lysozyme-EDTA treatment, the outer membrane is disrupted, resulting in the removal of protein localized in the outer membrane as well as protein present in the periplasm. This results in only inner membrane sorted protein remaining in the spheroplast cells. These cells can then be selected by flow cytometry after being labeled with fluorescent ligand probe. From these sorted cells, the sequences useful for tethering proteins on the inner membranes can be obtained.

Figure 17:
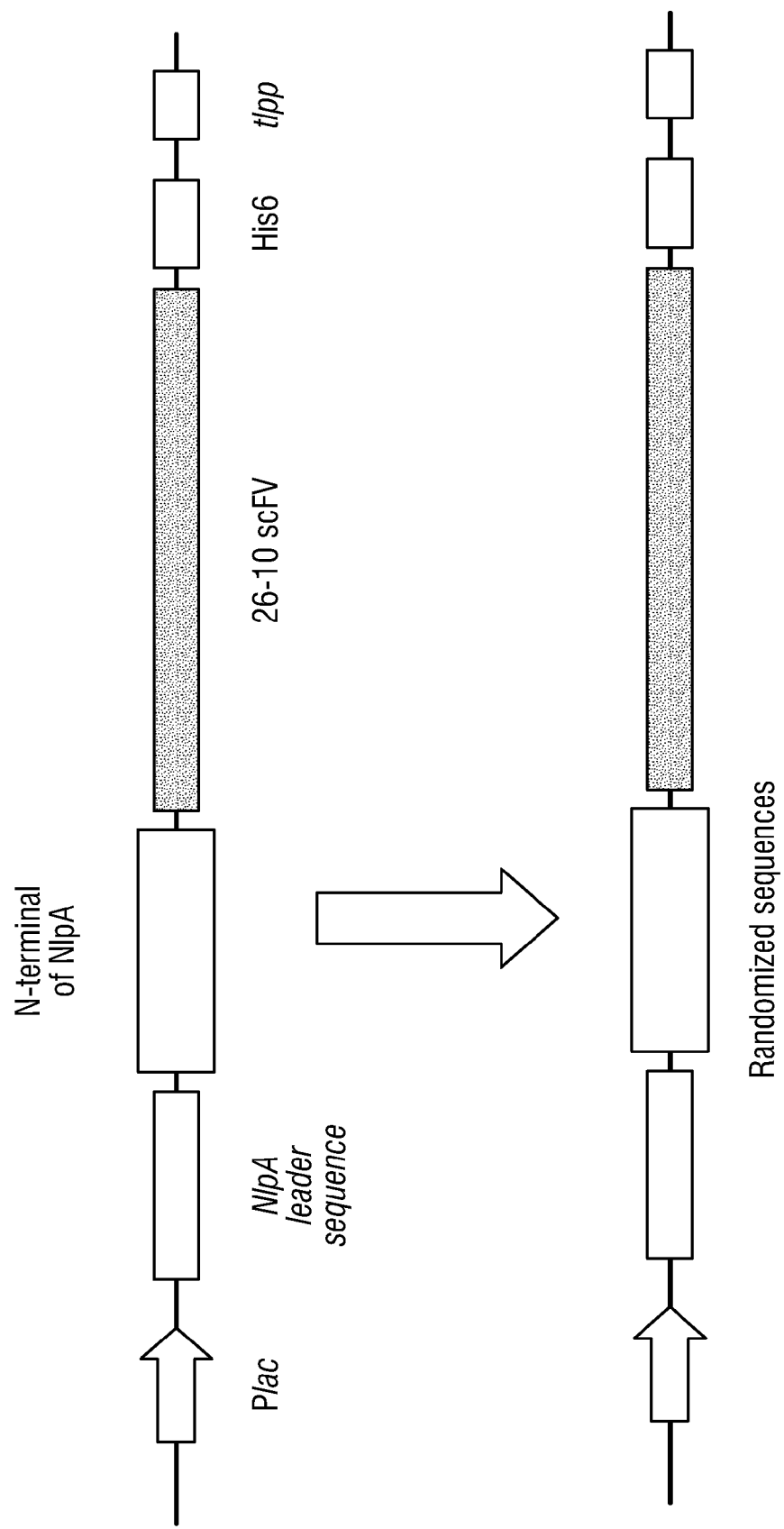
FIG. 17: Simple structure of the randomized NlpA library vector.

For library construction, 26-10 scFv was used as the anchored protein in APEx. This protein could be labeled with the Bodipy-Digoxigenin probe. For the randomization of NlpA, three primers, NlpA-Ran-F1 (CGAATTCTGCTG-GCAGGTTGCNNSNNSNNSNNSNNSGAG-GCCCAGCCGGC)(SEQ ID NO:45), NlpA-Ran-F3 (GGACTGATGGATGGCTGGCCGG AATTCTGCTGGCAGGTTGC) (SEQ ID NO:46), and NlpA-Ran-R2 (GGACTGATGGATGGTCGACTGC GGCCGCGAATTC) (SEQ ID NO:47) were synthesized. Plasmid p26-10 scFv APEx, which contains the native NlpA sequence (CDQSSS (SEQ ID NO:44)), was used as template DNA for the PCR reaction using the three primers named above. The PCR products were digested with the FokI restriction enzyme, which can create the EcoRI-cut cohesive end (AATT, underlined above) and NotI-cut cohesive end (GGCC, underlined above), and the digested DNA was cloned into p26-10 scFv APEx digested with EcoRI and NotI restriction enzymes. The simple structure of the library vector is shown in FIG. 17. From the library (in *E. coli* Jude 1 strain), 16 clones were randomly chosen and their sequences for 5 amino acids were determined. All 16 clones showed fully randomized sequences in the 5 amino acids after the first Cys residue. This library was then used to screen for sequences useful for tethering proteins onto the inner membrane.

Example 10

Screening of Sequences for Tethering Proteins on the Membranes by Flow Cytometry Overnight cultures of the *E. coli* Jude1 library were subcultured into fresh TB medium at 37° C. After 2 hr, the flask was moved to a 25° C. shaking water bath to decrease the culture temperature. After 30 min cooling at 25° C., induction was done with 1 mM IPTG. After 4 hr, cells were collected and spheroplasts were prepared by lysozyme-EDTA treatment to remove the unbound 26-10 scFv from the periplasm as well as the outer membrane bound 26-10 scFv. Specifically, the collected cells were resuspended in a buffer (350 µL) containing 0.1 M Tris-Cl (pH 8.0) and 0.75 M sucrose, and then 700 µL of 1 mM NaEDTA was added. Lysozyme (Sigma) was added to 100 µg/mL and cells were incubated at 37° C. for 10 min. Finally, 50 µL of 0.5 M $MgCl_2$ was added and further incubated on ice for 10 min. The spheroplast cells were then pelleted by 10 min of centrifugation at 10,000 rpm and then resuspended in 1×PBS buffer (phosphate buffered saline).

For flow cytometric analysis, 0.1 mL of spheroplast cells were mixed with 100 nM of Bodipy-Digoxigenin conjugate probe (Molecular Probes, USA) in 0.9 mL of 1×PBS and after 30 min of incubation at room temperature with shaking, the cells were collected by centrifugation. The cells were resuspended in 1 mL of 1×PBS and a 5 µL aliquot was diluted into 2 mL of 1×PBS buffer prior to sorting using a Moflo flow cytometry (Darko Cytomation, USA). The desired cell population was gated by setting appropriate SSC (side-scattered light), FSC (Forward-scattered light), and FL1 windows (for Bodipy fluorescence) and cells were sorted in purify 1 and 2 drop mode.

A total of $9 \times 10^7$ bacteria were sorted using an ultra-high throughput Cytomation Inc. MoFlo droplet deflection flow cytometer selectively gated for high BODIPY™ fluorescence. Approximately 2% of the cells sorted with the highest 530 nm fluorescence (FL1) were collected and immediately resorted as above. DNA encoding scFvs was rescued by PCR amplification of the approximately $7 \times 10^4$ fluorescent events recovered by sorting. In this PCR reaction, two primers, NlpARan-Fok-F1 (GGACTGATGGATGTACGAATTT CTAGAGAAGGAG) (SEQ ID NO:48) and NLPA-RAN-R2 (GGACTGATGGATGGATTTGATCTCGAGCTTGG) (SEQ ID NO:49) were used. The PCR product was digested with FokI restriction enzyme, which can create the XbaI-cut cohesive end (CTAG, underlined above) and XhoI-cut cohesive end (TCGA, underlined above), and the digested DNA was cloned into p26-10 scFv APEx digested with the XbaI and XhoI restriction enzymes. A second round of sorting was then performed as described above, followed by the PCR reaction and cloning, also as described above. 100 clones were then randomly chosen for the analysis of their fluorescence by Flow cytometry.

As shown in Table 3, among 100 clones, 12 clones showed higher or similar fluorescence as compared to the native NlpA sequence (CDQSSS (SEQ ID NO:44)). The high fluorescence indicates the anchoring of 26-10 scFv to inner membrane. This data thus shows that the APEx system can be used to discover sequences useful for tethering proteins onto the inner membrane.

TABLE 3

The amino acid sequences in randomized region and relative fluorescence of sorted clones.

| Clone No. | Amino acid sequence in randomized region | Relative fluorescence* |
|---|---|---|
| 4 | CNGESA (SEQ ID NO:50) | +++ |
| 56 | CTHLSG (SEQ ID NO:51) | +++ |
| 67 | CSRGIL (SEQ ID NO:52) | +++ |
| 71 | CREPMS (SEQ ID NO:53) | +++ |
| 95 | CSELLR (SEQ ID NO:54) | +++ |
| 55 | CESLNA (SEQ ID NO:55) | ++ |
| 77 | CGKLMV (SEQ ID NO:56) | ++ |
| 73 | CGPGSH (SEQ ID NO:57) | ++ |
| 75 | CYKSTT (SEQ ID NO:58) | ++ |
| 80 | CLALVQ (SEQ ID NO:59) | ++ |
| 88 | CMLSST (SEQ ID NO:60) | ++ |
| 98 | CVLLYS (SEQ ID NO:61) | ++ |

*The fluorescence of native NlpA (CDQSSS (SEQ ID NO:44)) is between '+++' and '++' symbols.

All of the methods disclosed and claimed herein can be made and executed without undue experimentation in light of the present disclosure. While the compositions and methods of this invention have been described in terms of preferred embodiments, it will be apparent to those of skill in the art that variations may be applied to the methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

Abbondanzo et al., *Am J Pediatr Hematol Oncol*, 12(4):480-9, 1990.
Almendro et al., *J Immunol*. 157:5411, 1996.
Angel et al., *Cell*, 49:729, 1987b.
Angel et al., *Mol. Cell. Biod.*, 7:2256, 1987a.
Atchison and Perry, *Cell*, 46:253, 1986.
Atchison and Perry, *Cell*, 48:121, 1987.
Atherton et al., *Biol, of Reproduction*, 32:155, 1985.
Banerji etal., *Cell*, 27:299, 1981.
Banerji et al., *Cell*, 35:729, 1983.
Barbas et al., *Proc. Nati. Acad. Sci. USA*, 88:7978-7982, 1991.
Bellus, *J. Macromol. Sci. Pure Appl. Chem.*, RS3241(1): 1355-1376, 1994.
Berberian et al., *Science*, 261:1588-1591, 1993.
Berkhout et al., *Cell*, 59:273, 1989.

Berks, B., C,. (1996). A common export pathway for proteins binding complex redox cofactors?*Mol Microbiol* 22, 393-404.
Berrier et al., *J. Bacteriol.*, 182:248, 2000.
Blanaretal.,*EMBO J.*, 8:1139, 1989.
Boder and Wittrup, *Methods Enzymol.*, 328:430-444, 2000.
Boder et al., *Proc. Natl. Acad. Sci. USA*, 97:10701-10705, 2000.
Bodine and Ley, *EMBO J.*, 6:2997, 1987.
Boeke and Mol, *Proc. Natl. Acad. Sci. USA*, 79:5200-5204, 1982.
Boeke et al., *Mol. Gen. Genet.*, 186: 1982.
Boshart et al., *Cell*, 41:521, 1985.
Bosze et al., *EMBO J.*, 5:1615, 1986.
Braddock et al., *Cell*, 58:269, 1989.
Buchanan, G., Leeuw, E., Stanley, N. R., Wexler, M., Berks, B. C., Sargent, F. & Palmer, T.(2002). Functional complexity of the twin-arginine translocase TatC component revealedby site-directed mutagenesis. *Mol Microbiol* 43, 1457-1470.
Bukau et al., *J. Bacteriol.*, 163:61, 1985.
Bulla and Siddiqui, *J. Virol.*, 62:1437, 1986.
Burioni et al., *Res. Virol.*, 149:327, 1998.
Burman etal., *J. Bacteriol.*, 112:1364, 1972.
Campbell and Villarreal, *Mol. Cell. Biol.*, 8:1993, 1988.
Campere and Tilghman, *Genes and Dev.*, 3:537, 1989.
Campo et al., *Nature*, 303:77, 1983.
Carter et al., *Nucleic Acids Res* 13:4431, 1985.
Celander and Haseltine, *J. Virology*, 61:269, 1987.
Celander et al., *J. Virology*, 62:1314, 1988.
Chandler et al., *Cell*, 33 :489, 1983.
Chang et al., *Mol. Cell. Biol.*, 9:2153, 1989.
Chatterjee et al., *Proc. Nat'Acad. Sci. USA.*, 86:9114, 1989.
Chen et al., *J. Md. Biol.*, 293:865, 1999.
Chen et al., *Nat. Biotechnol.*, 19:537-542, 2001.
Chen et al., *Protein Eng.*, 12:349-356, 1999.
Chen, G., Hayhurst, A., Thomas, J. G., Harvey, B. R., Iverson, B. L. & Georgiou, G. (2001).Isolation of high-affinity ligand-binding proteins by periplasmic expression with cytometric screening(PECS). *Nat Biotechnol* 19, 537-542.
Choi et al., *Cell*, 53:519, 1988.
Chowdhury and Pastan, *Nat. Biotech.*, 17:568, 1999.
Cleary et al., *Trends Microbiol.*, 4:131-136, 1994.
Coffin, In: *Virology*, ed., New York: Raven Press, pp. 1437-1500, 1990.
Cohen et al., *Proc. Nat'l Acad. Sci. USA* 75:472, 1987.
Coia et al., *Gene* 201:203, 1997.
Corey et al., *Gene*, 128:129, 1993.
Cormack, B. P., Valdivia, R. H. & Falkow, S. (1996). FACS-optimized mutants of the greenfluorescent protein(GFP). *Gene* 173, 33-38.
Costa et al., *Mol. Cell. Biol.*, 8:81, 1988.
Cripe et al., *EMBO J.*, 6:3745, 1987.
Culotta and Hamer, *Mol. Cell. Biol.*, 9:1376, 1989.
Dall'Acqua and Carter, *Curr. Opin. Struct. Biol.*, 8:443, 1998.
Dandolo et al., *J. Virology*, 47:55, 1983.
Daugherty et al., *J Immunol. Methods.* 243:211, 2000.
Daugherty et al., *Proc. Natl. Acad. Sci. USA*, 97:2029-2034, 2000.
Daugherty et al., *Prot. Eng.*, 11:825, 1998.
Daugherty et al., *Protein Eng.*, 12:613-621, 1999.
De Haard et al., *J. Biol. Chem.*, 274:18218, 1999.
De Jager Ret al.,*Semin Nucl Med* 23:165, 1993.
De Villiers et al., *Nature*, 312:242, 1984.
De Wildt et al., *Nat. Biotechnol.* 18:, 989, 2000.
Decad and Nikaido, *J. Bacteriol.*, 128:325, 1976.
Deng et al., *J. Biol. Chem.*, 269:9533, 1994.
Deng et al., *Proc. Natl. Acad. Sci. USA*. 92:4992, 1995.
Deschamps et al., *Science*, 230:1174, 1985.
Dholakia et al., *J. Biol. Chem.*, 264, 20638-20642, 1989.
Doolittle MH and Ben-Zeev O, *Methods Mol Biol.*, 109:215, 1999.
Drew, D. E., von Heijne, G., Nordlund, P. & de Gier, J. W. (2001). Green fluorescent protein asan indicator to monitor membrane protein overexpression in *Escherichia coli*. *FEBS Lett* 507, 220-224.
Duenas and Borrebaeck, *Biotechnology*, 12:999, 1994.
Edbrooke et al., *Mol. Cell. Biol.*, 9:1908, 1989.
Edlund et al., *Science*, 230:912, 1985.
Ehrmann, M., Boyd, D. & Beckwith, J. (1990). Genetic analysis of membrane protein topolog by a sandwich gene fusion approach. *Proc Natl Acad Sci USA* 87, 7574-7578.
Farmer et al., *FEMS Microbiol. Lett.*, 176:11, 1999.
Feldhaus et al., *Nat. Biotechnol.*, 21:163-170, 2003.
Feng and Holland, *Nature*, 334:6 178, 1988.
Firak and Subramanian, *Mol. Cell. Biol.*, 6:3667, 1986.
Frohman, In. *PCR PROTOCOLS. A GUIDE TO METHODS AND APPLICATIONS*, AcademicPress, N.Y., 1990.
Fromant et al., *Anal. Biochem.*, 224:347-353, 1995.
Fujita et al., *Cell*, 49:357, 1987.
Gennity and Inouye *J. Bacteriol* 174(7):2095, 1992
Georgiou et al., *Nat. Biotechnol.* 15:29, 1997.
Georgiou, *Adv. Protein Chem.*, 55:293-315, 2000.
Gilles et al., *Cell*, 33:717, 1983.
Gloss et al., *EMBO J.*, 6:3735, 1987.
Godbout et al., *Mol. Cell. Biol.*, 8:1169, 1988.
Goodbourn and Maniatis, *Proc. Nat'l Acad. Sci. USA*, 85:1447, 1988.
Goodbourn et al., *Cell*, 45:601, 1986.
Gouffi, K., Santini, C. L. & Wu, L. F. (2002). Topology determination and functional analysis ofthe *Escherichia coli* TatC protein. *FEBS Lett* 525, 65-70.
Gough et al., *J. Immunol. Met.*, 228:97, 1999.
Greene et al., *Immunology Today*, 10:272, 1989.
Griep et al., *Prot. Exp. Purif,* 16:63, 1999.
Griffiths et al., *EMBO J.*, 13: 3245, 1994.
Grossohedl and Baltimore, *Cell*, 41:885, 1985.
Gulbis and Galand, *Hum Pathol* 24:1271, 1993.
Hanes and Pluckthun, *Proc. Natl. Acad. Sci. USA*, 94:4937-4942, 1997.
Haslinger and Karin, *Proc. Nat'l Acad. Sci. USA.*, 82:8572, 1985.
Hauber and Cullen, *J. Virology*, 62:673, 1988.
Hawkins et al., *J. Mol. Biol.*, 226:889, 1992.
Hayhurst and Georgiou, *Curr. Opin. Chem. Biol.*, 5:683-689, 2001.
Hayhurst and Harris, *Protein Expr. Purif,* 15:336-343, 1999.
Hayhurst et al., *J. Immunol. Methods*, 276:185-196, 2003.
Hayhurst, *Protein Expr. Purif,* 18:1-10, 2000.
Hearing et al., *J. Virol.*, 67:2555-2558, 1987.
Hen et al., *Nature*, 321:249, 1986.
Hensel et al., *Lymphokine Res.*, 8:347, 1989.
Herr and Clarke, *Cell*, 45:461, 1986.
Hirochika et al., *J. Virol.*, 61:2599, 1987.
Hirsch et al., *Mol. Cell. Biol.*, 10:1959, 1990.
Hobot et al., *J. Bacteriol.* 160:143, 1984.
Hoess, *Chem. Rev.*, 101:3205-3218, 2001.
Holbrook et al., *Virology*, 157:211, 1987.
Hoogenboom et al., *Adv. Drug. Deliv. Rev.*, 31:5, 1998.
Horlick and Benfield, *Mol. Cell. Biol.*, 9:2396, 1989.
Hsiung et al, *Biotechnology*, 4:991, 1994.
Huang et al., *Cell*, 27:245, 1981.
Hudson and Souriau, *Nat. Med.* 9:129-134, 2003.
Hudson, *Curr. Opin. Biotechnol.*, 9:395, 1998.

Hultgren et al., *Bacterial Adhesins Assembly*, Vol. 2., 1996.
Hwang et al., *Mol. Cell. Biol.*, 10:585, 1990.
Imagawa et al., *Cell*, 51:251, 1987.
Imbra and Karin, *Nature*, 323:555, 1986.
Imler et al., *Mol. Cell. Biol.*, 7:2558, 1987.
Imperiale and Nevins, *Mol. Cell. Biol.*, 4:875, 1984.
Innis et al., *Proc Natl Acad Sci USA*. 85:9436, 1988.
Irvin etal., *J. Bacteriol.*, 145:1397, 1981.
Jakobovits et al., *Mol. Cell. Biol.*, 8:2555, 1988.
Jameel and Siddiqui, *Mol. Cell. Biol.*, 6:710, 1986.
Jaynes et al., *Mol. Cell. Biol.*, 8:62, 1988.
Jeffrey et al., *Proc. Natl. Acad. Sci. USA*. 90:10310, 1993.
Johns et al., *J. Immunol. Methods*, 239:137, 2000.
Johnson et al., *Mol. Cell. Biol.*, 9:3393, 1989.
Jouenne and Junter, FEMS *Microbiol. Lett.*, 56:313, 1990.
Kadesch and Berg, *Mol. Cell. Biol.*, 6:2593, 1986.
Kang et al., *Science*, 240:1034-1036, 1988.
Karin et al., *Mol. Cell. Biol.*, 7:606, 1987.
Katinka et al., *Cell*, 20:393, 1980.
Katinka et at., *Nature*, 290:720, 1981.
Kawamoto et at., *Mol. Cell. Biol.*, 8:267, 1988.
Khatoon et at., Ann. of Neurology, 26, 210-219, 1989.
Kiledjian et at., *Mol. Cell. Biol.*, 8:145, 1988.
King et at., *J. Biol. Chem.*, 269:10218, 1989.
Kjaer et at., FEBS *Lett.*, 43 1:448, 1998.
Kiamut et at., *Mol. Cell. Biol.*, 10:193, 1990.
Knappick et at., *J. Mol. Biol.*, 296:57, 2000.
Koch et at., *Mol. Cell. Biol.*, 9:303, 1989.
Kohier et at., *Methods Enzymol.*, 178:3, 1989.
Kraus et at., *FEBS Lett.*, 428:165, 1998.
Krebber et at., *Gene*, 178:71, 1996.
Krebberetal., *J. Immunol. Methods*, 201:35-55, 1997.
Kreier et at., Infection, Resistance and Immunity, Harper & Row, New York, (1991)).
Kriegler and Botchan, In: *Eukaryotic Viral Vectors*, Y. Gluzman, ed., Cold Spring Harbor: ColdSpring Harbor Laboratory, NY, 1982.
Kriegler et at., *Cell*, 38:483, 1984a.
Kriegler et at., *Cell*, 53:45, 1988.
Kriegler et at., In: Cancer Cells 2/*Oncogenes and Viral Genes*, Van de Woude et at. eds, ColdSpring Harbor, Cold Spring Harbor Laboratory, 1984*b*.
Kriegler et at., In: *Gene Expression*, D. Hamer and M. Rosenberg, eds., New York: Alan R. Liss, 1983.
Kuhi etal., *Cell*, 50:1057, 1987.
Kunzetal., *Nucl.Acids Res.*, 17:1121, 1989.
Kwoh et at, *Proc Natl Acad Sci USA*. 86:1173, 1989.
Labischinski et at., J. Bacteriot., 162:9, 1985.
Lareyre et at., *J Biol Chem.*, 274:8282, 1999.
Larsen et at., *Proc. Nat'l Acad. Sci. USA.*, 83:8283, 1986.
Laspia et at., *Cell*, 59:283, 1989.
Latimer et at., *Mol. Cell. Biol.*, 10:760, 1990.
Lee et at., *J Auton Nerv Syst.* 74:86, 1997
Lee et at., *Nature*, 294:228, 1981.
Lenert et at., *Science*, 248:1639-1643, 1990.
Levinson et at., *Nature*, 295:79, 1982.
Levitan, *J. Mol. Biol.*, 277:893, 1998.
Li et a!., *Nat. Struct. Biol.*, 10:482-488, 2003.
Lin et al., *Mol. Cell. Biol.*, 10:850, 1990.
Luriaetal., *EMBO J.*, 6:3307, 1987.
Lusky and Botchan, *Proc. Nat'l Acad. Sci. USA.*, 83:3609, 1986.
Lusky et at., *Mol. Cell. Biol.*, 3:1108, 1983.
Lutz, S., Ostermejer, M. & Benkovic, S. J. (2001). Rapid generation of incremental truncation libraries for protein engineering using alpha-phosphothioate nucleotides. *Nucleic AcidsRes* 29, E16.

MacKenzie and To, *J. Immunol. Methods*, 220:39, 1998.
MacKenzie et at., *J. Biol. Chem.*, 271:1527, 1996.
Maenaka et at., *Biochem Biophys Res Commun.*, 2 18:682, 1996.
Majors and Varmus, *Proc. Nat'l Acad. Sci. USA.*, 80:5866, 1983.
Malmborg et at., *J. Immunol. Methods*, 198:51, 1996.
Marciano et at., *Science* 284:1516, 1999.
Marks et at., *Bio/Technol.* 10:779, 1992.
Marks et at., *J. Mol. Biol.*, 222:581, 1991.
Martinez et at., *Biochemistry*, 35:1179, 1996.
Martinez et at., *J. Biotechnol.*, 71:59, 1999.
Masuda K et at. *PNAS* 99(11):7390, 2002.
Maynard et at., *Nat. Biotechnol.*, 20:597-601, 2002.
McNeall et at., *Gene*, 76:81, 1989.
Miksicek et at., *Cell*, 46:203, 1986.
Mingarro et at., *Trends Biotechnol.*, 15:432-437, 1997.
Miroux and Walker, *J. Mol. Biol.*, 260:289-298, 1996.
Mitchell et at., Ann. *N.Y Acad. Sci.*, 690:153, 1993.
Mordacq and Linzer, *Genes and Dev.*, 3:760, 1989.
Moreau et at., *Nucl. Acids Res.*, 9:6047, 1981.
Morrison, et al., *Proc. Nat'l. Acad. Sci USA*. 81:6851, 1984.
Muesing et at., *Cell*, 48:691, 1987.
Munson & Pollard, Anal. Biochem. 107:220, 1980.
Mutuberria et al., *J. Immunol. Methods*, 231:65, 1999.
Nakae,J. Blot. Chem., 251:2176, 1976.
Neu and Heppel, *J. Biol. Chem.*, 240:3685-3692, 1965.
Nikaido and Nakae, *Adv. Microb. Physiol.*, 20:163, 1979.
Nikaido and Vaara, *Microbiol. Rev.* 49:1, 1985.
Nissim et at., *EMBO J.*, 13:692, 1994.
Nomoto et at., *Gene*, 236:259, 1999.
Ohara et at., "One-sided polymerase chain reaction: the amplification of cDNA,"
Oka et at, Proc. Natl. Acad. Sd. U.S.A., Vol 82, pp 7212-7216, November 1985
Olsen et at., *Nat. Biotechnot*, 18:1071-1074, 2000.
O'Shannessy et at., *J. Immun. Meth.*, 99, 153-161, 1987.
Owens & Haley, *J. Biol. Chem.*, 259:14843-14848, 1987.
Painbeni et at., *Proc Natl. Acad. Sci. USA*, 94:6712, 1997.
Palrniter et at., *Nature*, 300:611, 1982.
Pech et at., *Mol. Cell. Biol.*, 9:396, 1989.
Perez-Stable and Constantini, *Mol. Cell. Biol.*, 10:1116, 1990.
Picard and Schaffner, *Nature*, 307:83, 1984.
Pini et at., *J. Biol. Chem.*, 273:21769, 1998.
Pinkert et at., *Genes and Dev.*, 1:268, 1987.
Ponta et at., *Proc. Nat'l Acad. Sci. USA.*, 82:1020, 1985.
Porton et at., *Mol. Cell. Biol.*, 10:1076, 1990.
Potter & Haley, Meth. in Enzymol., 91, 613-633, 1983.
Pugsley, *Microbiol. Rev.*, 57:50-108, 1993.
Queen and Baltimore, *Cell*, 35:741, 1983.
Quinn et at., *Mol. Cell. Biol.*, 9:4713, 1989.
Rakonjac and Model, *J. Mol. Biol.*, 282:25, 1998.
Rakonjac et at., *J Mol. Biol.*, 289:1253, 1999.
Rao and Torriani, *J. Bacteriol.*, 170, 5216, 1988.
Redondo et al., *Science*, 247:1225, 1990.
Reisman and Rotter, *Mol. Cell. Biol.*, 9:3571, 1989.
Resendez Jr. et al., *Mol. Cell. Biol.*, 8:4579, 1988.
Ripe et at., *Mol. Cell. Biol.*, 9:2224, 1989.
Rittling et al., *Nucl. Acids Res.*, 17:16 19, 1989.
Rodi and Makowski, *Curr. Opin. Biotechnol.*, 10:87-93, 1999.
Rosen etal., *Cell*, 41:813, 1988.
Sagt et al., *Appl. Environ. Microbiol.*, 68:2155-2160, 2002.
Sakai et al., *Genes and Dev.*, 2:1144, 1988.

Sambrook et al., In: *Molecular Cloning: A Laboratory Manual*, Vol. 1, Cold Spring Harbor Laboratory Press, Cold Spring Harbor, NY, Ch. 7, 7.19-17.29, 1989.
Samuelson et at., *Nature*, 406:637-641, 2000.
Sasso et al., *J. Immunol.*, 142:2778-2783, 1989.
Satake et at., *J. Virology*, 62:970, 1988.
Sblattero and Bradbury, *Nat. Biotechnol.*, 18:75, 2000.
Schaffner et al., *J. Mol. Biol.*, 201:81, 1988.
Searle et al., *Mol. Cell. Biol.*, 5:1480, 1985.
Seydel et at., *Mol. Microbiol.*, 34:810-821, 1999.
Sharp and Marciniak, *Cell*, 59:229, 1989.
Shaul and Ben-Levy, *EMBO J.*, 6:1913, 1987.
Sheets et at., *Proc. Natl. Acad. Sci. USA.*, 95:6157, 1998.
Sherman et at., *Mol. Cell. Biol.*, 9:50, 1989.
Shorki et at., *J. Immunol.*, 146:936-940, 1991.
Shusta et at., *J. Mol. Biol.*, 292:949, 1999.
Silvermann et at., *J. Clin. Invest.*, 96:417-426, 1995.
Sleigh and Lockett, *J. EMBO*, 4:3831, 1985.
Smith, *Science*, 228:1315-1317, 1985.
Somerville et at., *Appl. Microbiol. Biotechnol.*, 42:595-603, 1994.
Spalholz et at., Cell, 42:183, 1985.
Spandau and Lee, *J. Virology*, 62427, 1988.
Spandidos and Willcie, *EMBO J.*, 2:1193, 1983.
Stathopoulos et al., *Appl. Microbiol. Biotechnol.*, 45:112-119, 1996.
Stephens and Hentschel, *Biochem. J.*, 248:1, 1987.
Stuart et al., *Nature*, 317:828, 1985.
Sullivan and Peterlin, *Mol. Cell. Biol.*, 7:3315, 1987.
Swartzendruber and Lehman, *J. Cell. Physiology*, 85:179, 1975.
T. J. Gibson, PhD thesis, University of Cambridge (1984).
Takebe et al., *Mol. Cell. Biol.*, 8:466, 1988.
Tavemier et al., *Nature*, 301:634, 1983.
Taylor and Kingston, *Mol. Cell. Biol.*, 10:165, 1990a.
Taylor et al., *J. Biol. Chem.*, 264:15160, 1989.
Thiesen et al., *J. Virology*, 62:614, 1988.
Thompson et al., *J. Mol. Biol.* 256, 77, 1999????.
Thorstenson et al., *J. Bacteriol.*, 179:5333, 1997.
Tomlinson et al., *J. Mol. Biol.* 227:776, 1992.
Tronche et al., *Mol. Biol. Med.*, 7:173, 1990.
Tronche et al., *Mol. Cell. Biol.*, 9:4759, 1989.
Trudel and Constantini, *Genes and Dev.*, 6:954, 1987.
Tsumaki et al., *J Biol Chem.* 273:22861, 1998.
Van Wielink and Duine, *Trends Biochem Sci.*, 15:136, 1990.
Vannice and Levinson, *J. Virology*, 62:1305, 1988.
Vasseur et al., *Proc. Natl. Acad. Sci. USA.*, 77:1068, 1980.
Vaughan et al., *Nat. Biotechnol.*, 14:309, 1996.
Walker et al., *Nucleic Acids Res.* 20:1691, 1992
Wang and Calame, *Cell*, 47:241, 1986.
Waterhouse et al., *Nucl. Acids Res.* 21, 2265-2266 (1993)
Watson, M. Nucleic Acids Research, Vol 12, No. 13, 1984, pp. 5145-5164),
Weber et al., *Cell*, 36:983, 1984.
Weinberger et al. *Mol. Cell. Biol.*, 8:988, 1984.
Winoto and Baltimore, *Cell*, 59:649, 1989.
Winter et al, *Ann. Rev. Immunol.* 12: 433, 1994.
Wittrup, *Nat. Biotechnol.*, 18:1039-1040, 2000.
Wu et al., *Biochem Biophys Res Commun.* 233:221, 1997.
Yakushi et al., *Nat. Cell. Biol.*, 2:212-218, 2000.
Yakushi T. et al. *Journal of Bacteriology* 179(9):2857, 1997.
Yamaguchi and Jnouye., *Journal of Bacteriology* 170 no.8: 3747, 1988.
Yamaguchi et al., *Cell*, 53:423-432, 1988.
Yu et al., *J. Biol. Chem.*, 261:2284-2288, 1986.
Yutzey et al. *Mol. Cell. Biol.*, 9:1397, 1989.
Zhao-Emonet et al., *Gene Ther.* 6:1638, 1999.

What is claimed is:

1. A method of obtaining a bacterium comprising a nucleic acid sequence encoding an inner membrane anchor polypeptide that anchors a heterologous polypeptide to the outer side of the inner membrane of a Gram negative bacterium comprising the steps of:
   (a) providing a Gram negative bacterium comprising an inner membrane, an outer membrane and a periplasm; said bacterium comprising a nucleic acid sequence encoding a fusion between a heterologous polypeptide and a candidate inner membrane anchor sequence;
   (b) removing the outer membrane; and
   (c) selecting the bacterium based on the presence of the heterologous polypeptide anchored to the outer side of the inner membrane to identify an inner membrane anchor polypeptide that anchors a heterologous polypeptide to the outer side of the inner membrane of said bacterium.

2. The method of claim 1, further defined as a method of obtaining a nucleic acid sequence encoding an inner membrane anchor sequence that anchors a heterologous polypeptide to the outer side of the inner membrane, the method further comprising the step of:
   (d) cloning a nucleic acid sequence encoding the inner membrane anchor polypeptide.

3. The method of claim 1, wherein selecting said bacterium comprises detecting the heterologous polypeptide with a binding polypeptide having specific affinity for the heterologous polypeptide.

4. The method of claim 3, further comprising use of at least a second binding polypeptide having affinity for the heterologous polypeptide and/or the binding polypeptide having specific affinity for the heterologous polypeptide.

5. The method of claim 3, wherein the second binding polypeptide is an antibody or fragment thereof.

6. The method of claim 5, wherein the antibody or fragment thereof is fluorescently labeled.

7. The method of claim 3, wherein selecting said bacterium comprises use of at least a third binding polypeptide having specific affinity for the heterologous polypeptide and/or said second binding polypeptide to label said bacterium.

8. The method of claim 1, wherein the heterologous polypeptide comprises a detectable label.

9. The method of claim 8, wherein the detectable label is an antigen.

10. The method of claim 8, wherein the detectable label is GFP.

11. The method of claim 1, wherein said heterologous polypeptide comprises an antibody or fragment thereof.

12. The method of claim 11, wherein selecting the bacterium comprises detecting the antibody or fragment thereof with a labeled ligand having specific affinity for the antibody or fragment thereof.

13. The method of claim 1, wherein said Gram negative bacterium is an *E. coli* bacterium.

14. The method of claim 1, wherein step (a) is further defined as comprising providing a population of Gram negative bacteria.

15. The method of claim 14, wherein said population of bacteria is further defined as collectively expressing a plurality of candidate inner membrane anchor sequences.

16. The method of claim 14, wherein from about two to six rounds of selecting are carried out to obtain said bacterium from said population.

17. The method of claim 2, wherein the bacterium is non-viable.

18. The method of claim 2, wherein the bacterium is viable.

19. The method of claim 2, wherein cloning comprises amplification of the nucleic acid sequence.

20. The method of claim 1, wherein selecting is carried out by flow-cytometry or magnetic separation.

21. The method of claim 1, wherein said nucleic acid encoding a candidate inner membrane anchor polypeptide is flanked by known PCR primer sites.

22. The method of claim 1, wherein the candidate inner membrane anchor polypeptide is anchored to the outer side of the inner membrane with a transmembrane protein comprising the first six amino acids of NlpA.

23. The method of claim 22, wherein the candidate inner membrane anchor polypeptide is anchored via an N- or C-terminus of the polypeptide.

\* \* \* \* \*